(12) United States Patent
Graham

(10) Patent No.: US 9,387,246 B2
(45) Date of Patent: Jul. 12, 2016

(54) TREATMENT METHODS FOR RHEUMATOID ARTHRITIS

(71) Applicant: L. Douglas Graham, Chicago, IL (US)

(72) Inventor: L. Douglas Graham, Chicago, IL (US)

(*) Notice: Subject to any disclaimer, the term of this patent is extended or adjusted under 35 U.S.C. 154(b) by 0 days.

(21) Appl. No.: 14/476,659

(22) Filed: Sep. 3, 2014

(65) Prior Publication Data

US 2015/0064132 A1 Mar. 5, 2015

Related U.S. Application Data

(60) Provisional application No. 61/873,312, filed on Sep. 3, 2013.

(51) Int. Cl.
| | |
|---|---|
| G01N 33/564 | (2006.01) |
| C07K 16/24 | (2006.01) |
| A61K 39/395 | (2006.01) |
| A61K 31/519 | (2006.01) |
| A61K 31/42 | (2006.01) |
| C07K 16/28 | (2006.01) |
| A61K 31/573 | (2006.01) |
| A61K 31/5377 | (2006.01) |
| A61K 31/52 | (2006.01) |
| A61K 38/19 | (2006.01) |
| A61K 31/4706 | (2006.01) |
| C07K 14/705 | (2006.01) |

(52) U.S. Cl.
CPC ............. *A61K 39/3955* (2013.01); *A61K 31/42* (2013.01); *A61K 31/4706* (2013.01); *A61K 31/519* (2013.01); *A61K 31/52* (2013.01); *A61K 31/5377* (2013.01); *A61K 31/573* (2013.01); *A61K 38/191* (2013.01); *C07K 14/70521* (2013.01); *C07K 16/241* (2013.01); *C07K 16/248* (2013.01); *C07K 16/2827* (2013.01); *G01N 33/564* (2013.01); *C07K 2319/00* (2013.01); *G01N 2800/102* (2013.01); *G01N 2800/52* (2013.01)

(58) Field of Classification Search
None
See application file for complete search history.

(56) References Cited

U.S. PATENT DOCUMENTS

| 8,092,998 | B2 | 1/2012 | Stuhlmüller et al. |
| 8,168,568 | B1 | 5/2012 | Mehta et al. |
| 2008/0026485 | A1 | 1/2008 | Hueber et al. |
| 2009/0017472 | A1 | 1/2009 | Stuhlmüller et al. |
| 2010/0029007 | A1 | 2/2010 | Baumruken et al. |
| 2010/0145901 | A1 | 6/2010 | Han et al. |
| 2011/0212470 | A1 | 9/2011 | Somers et al. |
| 2011/0263451 | A1 | 10/2011 | Grogan et al. |
| 2012/0039900 | A1 | 2/2012 | Stuhlmüller et al. |

FOREIGN PATENT DOCUMENTS

EP 2 527 841 A1 11/2012

OTHER PUBLICATIONS

Zhao et al. (2012), J. of Imm. methods, vol. 38, pp. 72-80.*
Johansen et al. (2001), Scans J Rheumatol., vol. 30, pp. 297-304.*
Mullan et al. (2006), Arthritis & Rheumatism, vol. 54, No. 1, pp. 105-114.*
"ACR RA Clinical Trials Task Force: Request for Comments," *American College of Rheumatology*, available at www.rheumatology.org/about/clinical_trials.asp, last visited Dec. 23, 2104.
Centola, M., et al., "Development of a Multi-Biomarker Disease Activity Test for Rheumatoid Arthritis," *PLOS ONE* 8(4): 1-13, PLOS, United States (Apr. 9, 2013).
Chambers, R.E., et al., "Serum amyloid-A protein concentration in rheumatoid arthritis and its role in monitoring disease activity," *Annals of the Rheumatic Disease* 42: 665-667, BMJ, United Kingdom (1983).
Keenan, R.T., et al., "Erythrocyte sedimentation rate and C-reactive protein levels are poorly correlated with clinical measures of disease activity in rheumatoid arthritis, systemic lupus erythematosus and osteoarthritis patients," *Clinical and Experimental Rheumatology* 26: 814-819, Clinical and Experimental Rheumatology, Italy (2008).
"Notification of Transmittal of the International Search Report and The Written Opinion of the International Searching Authority, or The Declaration" mailed on Dec. 4, 2014 for International Application No. PCT/US2014/053905.
O'Hara, R., et al., "Acute-phase serum amyloid A production by rheumatoid arthritis synocial tissue," *Arthritis Res* 2: 142-144, Current Science Ltd, United Kingdom (2000).
Ribbens, C., et al., "Matrix Metalloproteinase-3 Serum Levels Are Correlated with Disease Activity and Predicted Clinical Response in Rheumatoid Arthritis," *J Rheumatol* 27(4): 888-893, Journal of Rheumatology Publishing Company, United States (2000).
Van Den Broek, T., et al., "The evolution of biomarkers in rheumatoid arthritis: From clinical research to clinical care," *Informa Healthcare* 8(11): 1773-1785, Informa Plc, United Kingdom (2008) (Abstract—1 page).
Van Den Broek, M., et al., "Personalized medicine: predicting responses to therapy in patients with RA," *Current Opinion in Pharmacology* 13(3): 463-469, Elsevier, United States (Apr. 8, 2013).
Visvanathan, S., et al., "E-section, Interleukin 18, Serum Amyloid A, and Matrix Metalloproteinase 9 Are Associated with Clinical Response to Golimumab plus Methotrexate in Patients with Active Rheumatoid Arthritis Despite Methotrexate Therapy," *J of Rheumatol* 36(7): 1371-1379, Journal of Rheumatology Publishing Company, United States (2009).
Alamanosa, Y., and Drosos, A. A., "Epidemiology of adult rheumatoid arthritis," *Autoimmunity Reviews* 4(3): 130-136, Elsevier B.V., Netherlands (2005).
Allart, C.F., and Huizinga, T.W., "Treatment strategies in recent onset rheumatoid arthritis," *Curr Opin Rheumatol.* 23(3): 241-244, Lippincott Williams & Wilkins, Inc., United States (2011).
Amos, R.S., et al., "Rheumatoid arthritis: relation of serum C-reactive protein and erythrocyte sedimentation rates to radiographic changes," *Br. Med. J.* 1(6055): 195-197, BMJ Publishing Group, United Kingdom (1977).

(Continued)

*Primary Examiner* — Christine J Saoud
*Assistant Examiner* — Jegatheesan Seharaseyon
(74) *Attorney, Agent, or Firm* — Sterne, Kessler, Goldstein & Fox P.L.L.C.

(57) ABSTRACT

The present invention provides methods for selecting treatment methods for rheumatoid arthritis based on an objective selection process (algorithm). The present invention also provides methods for treating rheumatoid arthritis with treatment methods selected based on the algorithm disclosed herein. The methods of the present invention provide a more effective means for treating patients with rheumatoid arthritis.

28 Claims, 8 Drawing Sheets

(56) References Cited

OTHER PUBLICATIONS

Cannella, A.C., and O'Dell, J.R., "Early Rheumatoid Arthritis: Pitfalls in Diagnosis and Review of Recent Clinical Trials," *Drugs* 66(10): 1319-1337, Adis Data Information BV, New Zealand (2006).

Charles-Schoeman, C., "Cardiovascular Disease and Rheumatoid Arthritis: An Update," *Curr Rheumatol Rep* 14(5): 455-462, Springer Science and Business Media, LLC, Germany (2012).

Dale, J., and Porter, D., "Optimizing the strategy of care in early rheumatoid arthritis," *Best Pract Res Clin Rheumatol* 24(4) 443-455, Elsevier Inc., United States 2010.

Dawes, P.T., et al., "Rheumatoid Arthritis: Treatment Which Controls the C-Reactive Protein and Erythrocyte Sedimentation Rate Reduces Radiological Progression," *British Journal of Rheumatology* 25: 44-49, Oxford University Press, United Kingdom (1986).

Feely, M., et al., "Therapeutic options for rheumatoid arthritis," *Expert Opin. Pharmacother.* 10( 13): 2095-2106, Informa, UK (2009).

Fries, J.F., "Reevaluating the Therapeutic Approach to Rheumatoid Arthritis: the "Sawtooth" Strategy," *Journal of Rheumatology* 17(22): 12-15, The Journal of Rheumatology Publishing Company Limited, Canada (1990).

Gabriel, S.E., "Who do people with rheumatoid arthritis still die prematurely?" *Ann Rheum Dis* 67(III): iii30-iii34, BMJ, United Kingdom (2008).

Gabriel, S.E., "Cardiovascular Morbidity and Mortality in Rheumatoid Arthritis," *Am. J. Med.* 121(10A): S9-S14, Elsevier Inc., United States (2008).

Keystone, E.C., "B cell in rheumatoid arthritis: from hypothesis to the clinic," *Rheumatology* 44(Suppl 2): ii8-ii12, Oxford University Press, United Kingdom (2005).

Llorca, J., et al., "Persistent Chronic Inflammation Contributes to the Development of Cancer in Patients with Rheumatoid Arthritis from a Define Population of Northestern Spain," *Semin. Arthritis Rheum.* 37(1): 31-38, Elsevier Inc., United States (2007).

Ma, X., and Xu, S., "TNF inhibitor therapy for rheumatoid arthritis (Review)," *Biomedical Reports* 1: 177-184, Spandidos Publication, Greece (2013).

Naz, S. M., and Symmons, D., "Mortality in established rheumatoid arthritis," *Best Practice & Research Clinical Rheumatology* 21(5): 871-883, Elseview Ltd., United States (2007).

Pincus, T., "Rheumatoid Arthritis: Disappointing Long-Term Outcomes Despite Successful Short-Term Clinical Trials," *J. Clin Epidemiol* 41(11): 1037-1041, Pergamon Press, United Kingdom (1988).

Rubbert-Roth, A., and Kinckh, A., "Treatment options in patients with rheumatoid arthritis failing initial TNF inhibitor therapy: a critical review," *Arthritis Research & Therapy* 11(Suppl 1): 1-12, BioMed Central Ltd., United Kingdom (2009).

Sokka, T., et al., "Mortality in rheumatoid arthritis: 2008 update," *Clinical Exp Rheumatol* 26(Suppl 51): S35-S61, Clinical and Experimental Rheumatology, (2008).

Ten Cate, D.F., et al., "Role of ultrasonography in diagnosing early rheumatoid arthritis and remission of rheumatoid arthritis—a systematic review of the literature," *Arthritis Research & Therapy* 15(R4): 1-9, BioMed Central Ltd., United Kingdom (2013).

Wilske, K., and Healey, L., "Remodeling the Pyramid-a Concept Whose Time Has Come," *The Journal of Rheumatology* 16(5): 565-567, The Journal of Rheumatology Publishing Company Limited, Canada (1989).

Wolfe, F., et al., "The Disease Activity Score Is Not Suitable as the Sole Criterion for Initiation and Evaluation of Anti-Tumor Necrosis Factor Therapy in the Clinic," *Arthritis & Rheumatism* 52(12): 3873-3879, American College of Rheumatology, United States (2005).

Young, A., et al., "The Clinical Assessment of Joint Inflammatory Activity in Rheumatoid Arthritis Related to Radiological Progression," *Rheumatology and Rehabilitation* 19: 14-19, Oxford University Press, United Kingdom (1980).

Simsek, I., "Predictors of Responses to TNF Inhibitors in Rheumatoid Arthritis, Do We Have New Tools for Personalized Medicine?" *Bulletin of the NYU Hospital for Joint Diseases* 70 (3): 187-190, Michael Ryan Pub., United States (2012).

Halilova, K., et al., "Markers of Treatment Response to Methotrexate in Rheumatoid Arthritis: Where Do We Stand?" *International Journal of Rheumatology* 1-7, Hindawi Publishing Corporation, Egypt (2012).

Li, W., et al., "Impact of a Multi-Biomarker Disease Activity Test on Rheumatoid Arthritis Treatment Decisions and Therapy Use," *Current Medical Research & Opinion* 29(1): 85-92, Informa UK Ltd, United Kingdom (2013).

Curtis, J.R., et al., "Validation of a Novel Multibiomaker Test to Assess Rheumatoid Arthritis Disease Activity," *Arthritis Care &Research* 64(12): 1794-1803, American College of Rheumatology, United States (2012).

Hirata, S., et al., "A Multi-Biomarker Score Measures Rheumatoid Arthritis Disease Activity in the BeSt Study," *Rheumatology* 52: 1202-1207, Oxford University Press, United Kingdom (2013).

Bakker, M.F., et al., "Performance of a Multi-Biomarker Score Measuring Rheumatoid Arthritis Disease Activity in the CAMERA Tight Control Study," *Ann Rheum Dis* 71: 1692-7, BJM, United Kingdom (2012).

Lekpa, F.K. et al., "Is IL-6 an Appropriate Target to Treat Spondyloarthritis Patients Refractory to Anti-TNF Therapy? A Multicentre Retrospective Observational Study," *Arthritis Research & Therapy* 14(2)R53:1-9, BioMed Central, United Kingdom (2012).

Meyer, P.W., et al., "Biomarkers and Genes Predictive of Disease Predisposition and Prognosis in Rheumatoid Arthritis," *Continuing Medical Education* 30 (8): 286-290, Health and Medical Publishing Group, South Africa (2012).

Cannella, A.C., et al., "Early Rheumatoid Arthritis, Pitfalls in Diagnosis and Review of Recent Clinical Trials" *Drugs* 66 (10): 1319-1337, Adis Data Information BV, New Zealand (2006).

Smolen, J.S. and Steiner, G., "Therapeutic Strategies for Rheumatoid Arthritis," *Nature Reviews Drug Discovery* 2:473-488, Macmillan Publishers Limited, England (2003).

Vilček, J., and Feldmann, M., "Historical Review: Cytokines as Therapeutics and Targets of Therapeutics," *TRENDS in Pharmacological Sciences* 25(4): 201-209, Elsevier Ltd., England (2004).

Hanami, K. et al., "Behavior of the Multi-Biomarker Disease Activity (Vectra DA Algorithm) Score and Components in Patients with Rheumatoid Arthritis Treated with Tocilizumab," *Annual European Congress of Rheumatology EULAR Abstracts*, Jun. 12-15, 2013, Spain (available as *Ann Rheum Dis* 72(Suppl3): 391 (2013) (Abstract—1 page).

Ma, M. H., et al., "A Multi-Biomarker Disease Activity (Vectra™ DA Algorithm) Score and Components are Associated with Sustained Clinical Remission in Rheumatoid Arthritis: The Remira Study," *Annual European Congress of Rheumatology EULAR Abstracts*, Jun. 12-15, 2013, Spain (available as *Ann Rheum Dis* 72(Suppl3): 394 (2013) (Abstract—1 page).

Ma, M.H., et al., "Remission in Early Rheumatoid Arthritis," *The Journal of Rheumatology* 37(7):1444-1453, Journal of Rheumatology, Canada (2010).

Jurgens, M.S., et al., "Response to MTX Plus Prednisone in Camera II Using a Multi-Biomarker Disease Activity Test (Vectra™ DA) and DAS28-ESR," *Annual Eurpoean Congress of Rheumatology EULAR Abstracts*, Jun. 12-15, 2013, Spain, (available as *Ann Rheum Dis* 72(Suppl3): 395 (2013) (Abstract—1 page).

Li, W., et al., "Characterization of the Multi-Biomarker Disease Activity (Vectra DA™ Algorithm) Score in a Subgroup of Patients from the Epidemiological Investigation of Rheumatoid Arthritis (EIRA) Cohort Receiving Methotrexate," *Annual European Congress of Rheumatology EULAR Abstracts*, Jun. 12-15, 2013, Spain (available as *Ann Rheum Dis* 72(Suppl3): 591 (2013) (Abstract—1 page).

Pedersen, S.J., et al., "ASDAS, BASDAI and Different Treatment Responses and their Relation to Biomarkers of Inflammation, Cartilage and Bone Turnover in Patients with Axial Spondyloarthritis Treated with TNFα Inhibitors," *Ann Rheum Dis.* 70 (8): 1375-1381, BMJ, United Kingdom (2011) (Abstract—2 pages ).

Pedersen, S.J., et al., "Circulating Levels of Interleukin-6, Vascular Endothelial Growth Factor, YKL-40, Matrix Metalloproteinase-3,

(56) References Cited

OTHER PUBLICATIONS and Total Aggrecan in Spondyloarthritis Patients During 3 Years of Treatment with TNFα Inhibitors," *Clin Rheumatol.* 29 (11): 1301-1309, Springer, Germany (2010) (Abstract—1 page).

Maksymowch, W.P., et al., "Etanercept Exerts Beneficial effects on Articular Cartilage Biomarkers of Degradation and Turnover in Patients with Ankylosing Spondylitis," *J. Rheumatol.* 32 (10): 1911-7, Journal of Rheumatology Publishing Co. (2005) (Abstract—2 pages).

McGeough, C.M., and Bjourson, A. J., "Diagnostic, Prognostic and Theranostic Genetic Biomarkers for Rheumatoid Arthritis," *J Clin Cell Immunol.* S6: 1-5, OMICS Group, United Kingdom (2012).

Park, M.C., et al., "Serum Leptin Levels Correlate with Interleukin-6 Levels and Disease Activity in Patients with Ankylosing Spondylitis," *Scand. J. Rheumatol.* 36: 101-106 (2010) (Abstract—1 page).

Chandran, V., et al., "Soluble Biomarkers Associated with Response to Treatment with Tumor Necrosis Factor Inhibitors in Psoriatic Arthritis," *J. Rheumatol*, 40 (6): 866-871, Journal of Rheumatology Publishing Co., Canada ( 2013) (Abstract 2 pages).

Fitzgerlad, O., and Chandran, V., "Update on Biomarkers in Psoriatic Arthritis: A Report from the GRAPPA 2010 Annual Meeting.," *J. Rheumatol.* 39 (2): 427-430, Journal of Rheumatology Publishing Co., Canada ( 2013) (Abstract—1 page).

Anderson, J., et al., "Rheumatoid Arthritis Disease Activity Measures: American College of Rheumatology Recommendations for Use in Clinical Practice," *Arthritis Care & Research* 64 (5):640-647, American College of Rheumatology, United States (2012).

"Vectra™ DA Disease Activity Test, RA at the Molecular Level," Crescendo Bioscience, United States (2011).

Narvaez, J., et al., "Predictors of Response to Rituximab in Patients with Active Rheumatoid Arthritis and Inadequate Response to Anti-TNF Agents or Traditional DMARDs," *Clin Exp Rheumatol* 29 (6): 991-997, Clinical and Experimental Rheumatology S.A.S, Italy (2011) (Abstract—2 pages).

Felson, D., et al., "American College of Rheumatology Preliminary Definition of Improvement in Rheumatoid Arthrisit," *Arthritis &Rheumatism* 38(6);727-735, American College of Rheumatology, United States (1995).

Prevoo, M.L.L., et al., "Modified Disease Activity Scores That Include Twenty-Eight-Joint Counts," *Arthritis &Rheumatism* 38(1):44-48, American College of Rheumatology, United States (1995).

Fransen, J., and Van Riel, P.L.C.M., "The Disease Activity Score and the EULAR Response Criteria," *Clin. Exp. Rheumatol.* 23 (Suppl. 39):S93-S99, W.B. Saunders Co., Philadelphia (2005).

Felson, D., et al., "American College of Rheumatology/European League Against Rheumatism Provisional Definition of Remission in Rheumatoid Arthritis for Clinical Trials," *Arthritis & Rheumatism* 63(3):573-586, American College or Rheumatology, United States (2011).

Singh, J., et al., "2012 Update of the 2008 American College of Rheumatology Recommendations for the Use of Disease-Modifying Antirheumatic Drugs and Biologic Agents in the Treatment of Rheumatoid Arthritis," *Arthritis Care & Research* 64(5):625-639, American College of Rheumatology, United States (2012).

Furst, D., "You Just Made the Diagnosis of RA: What Do You Do Now?," *5th Annual Perspectives iin Rheumatic Diseases™ Conference Highlights*, 1-2,7-8 (2012).

Crilly, A., et al., "The Effect of Azathioprinne on Serum Levels of Interleukin 6 and Soluble Interleukin 2 Receptor," *Scand J Rheumatol.* 23 (2): 87-91, Almqvist & Wiksell, United Kingdom (1994) (Abstract—1 page).

Barrera, P., "Effects of Antirheumatic Agents on Cytokines," *Semin Arthritis Rheum.* 245 (4): 234-253, Elsevier Science B.V., Netherlands (1996) (Abstract—1 page).

Upchurch, K., and Kay, J., "Evolution of Treatment for Rheumatoid Arthritis," *Rheumatology* 51: vi28-vi36, Oxford University Press, United Kingdom (2012).

Emery, P., "Optimizing Outcomes in Patients with Rheumatoid Arthritis and an Inadequate Response to Anti-TNF Treatment," *Rheumatology* 51:v22-v30, Oxford University Press, United Kingdom (2012).

Villeneuve, E., and Haraoui, B., "To Switch or to Change Class—the Biologic Dilemma in Rheumatoid Arthritis," *Nature Reviews Rheumatology* 6: 301-305, Macmillan Publishers Limited, United Kingdom (2010).

Ramiro, S., et al., "Applying Science in Practice: The Optimization of Biological Therapy in Rheumatoid Arthritis," *Arthritis Research & Therapy* 12(6):220 (1-8), Biomed Central, United Kingdom (2010).

Ward, M., et al., "RA Treatment Study Group: Improvement in RA Management," *Joint Bone Spine* 76(4):435-437, National Institute of Health, United States (2009).

Tak, P.P., "A Personalized Medicine Approach to Biologic Treatment of Rheumatoid Arthritis: A Preliminary Treatment Algorithm," *Rheumatology* 51:600-609, Oxford University Press, United Kingdom (2012).

Smolen, J., et al., "Treating Rheumatoid Arthritis to Target: Recommendations of an International Task Force," *Ann Rheum Dis.* 69:631-637, BMJ Journals, United Kingdom (2010).

Gibofsky, A., and Yazici, Y., "Treatment of Rheumatoid Arthritis: Strategies for Achieving Optimal Outcomes," *Ann Rheum Dis* 69 (6): 941-942, BMJ Journals, United Kingdom (2010).

Saag, K., et al., "American College of Rheumatology 2008 Recommendations for the Use of Nonbiologic and Biologic Disease-Modifying Antirheumatic Drugs in Rheumatoid Arthritis," *Arthritis & Rheumatism* 59(6):762-784, American College of Rheumatology, United States (2008).

Wolfe, F., "Comparative Usefulness of C-Reactive Protein and Erythorcyte Sedimentation Rate in Patients with Rheumatoid Arthritis," *J. Rheumatology* 24(8): 1477-85, Journal of Rheumatology Publishing Co, Canada, (1997) (Abstract—2 Pages).

Pincus, T. and Sokka T., "Laboratory Tests to Assess Patients with Rheumatoid Arthritis: Advantages and Limitations," *Rheum. Dis. Clin. North A,m.* 35(4): 731-734, W.B. Saunders Co., United States (2013) (Abstract—1 Page).

Cutolo, M., et al., "Serum Cytokines and Steroidal Hormones in Polymyalgia Rheumatica and Elderly-Onset Rheumatoid Arthritis," *Ann Rheum Dis* 65: 1438-1443, BMJ, United Kingdom (2006).

Mandell, B.F., "Polymyalgia Rheumatica: Clinical Presentation is Key to Diagnosis and Treatment," *Cleveland Clinic Journal of Medicine* 71(6):489-495, Cleveland Clinic Educational Foundation (2004).

Venables, P.J.W., and Maini, R.N., "Diagnosis and Differential Diagnosis of Rheumatoid Arthritis," available at www.uptodate.com, pp. 1-19, accessed on Jul. 27, 2013.

"Am. College of Rheumatology 2011 Recommendations for the Treatment of Juvenile Idiopathic Arthritis, Initiation and Safety Monitoring of Therapeutic Agents for the Treatment of Arthritis and Systemic Features; Clinician Guide," *American College of Rheumatology*: 1-7, United States (2011).

Beukelman, T., et al., "2011 American College of Rheumatology Recommendations for the Treatment of Juvenile Idiopathic Arthritis: Initiation and Safety Monitoring of Therapeutic Agents for the Treatment of Arthritis and Systemic Features," *Arthritis Case &Research* 63(4):465-482, American College of Rheumatology, United States (2011).

Schneider, R., and Laxer, R., "Systemic Juvenile Idiopathic Arthritis," *The Rheumatologist* (2012) , available at www.the-rheumatologist.org pp. 1-10, accessed on Jul. 27, 2013.

Punzi, L., et al., "Laboratory Findings in Psoriatic Arthritis," *Reumatismo.* 59 (Suppl. 1): 52-55, PagePress, Italy (2007) (Abstract—1 page).

Wolfe, F., "The Many Myths of Erythrocyte Sedimentation Rate and C-Reactive Protein," *The Journal of Rheumatology* 36(8):1568-1569, Journal of Rheumatology Publishing Co, Canada (2009).

Smolen, J., and Aletaha, D., "Monitoring Rheumatoid Arthritis," *Current Opinion in Rheumatology* 23:252-258, Wolters Kluwer, Holland (2011).

Pincus, T., "Advantages and Limitations of Quantitative Measures to Assess Rheumatoid Arthritis: Joint Counts, Radiographs, Laboratory

(56) References Cited

OTHER PUBLICATIONS

Tests, and Patient Questionnaires," *Bulleting of the NYU Hospital for Joint Diseases* 64(1&2): 32-39, Michael Ryan Pub., United States (2006).

Pincus, T., and Yazici, Y., "Complexities in Assessment of Rheumatoid Arthritis: Absence of a Single Gold Standard Measure," *Rheum Dis Clin N Am* 35: 687-697, W.B. Saunders Co., United States (2009).

Lindqvist, E., et al., "Prognostic Laboratory Markers of Joint Damage in Rheumatoid Arthritis," *Ann Rheum Dis* 64:196-201, H.K. Lewis, United Kingdom (2005).

Kaplan, M.J., "Cardiovascular Complication of Rheumatoid Arthritis—Assessment, Prevention and Treatment," *Rheum Dis Clin North Am.* 36(2):405-426, National Institutes of Health, United States (2010).

Smolen, J. and Aletaha, D., "Developments in Clinical Understanding of Rheumatoid Arthritis," *Arthritis Research & Therapy* 11:204 (1-9), BioMed Central, United Kingdom (2009).

"EULAR Issues Updated Rheumatoid Arthritis (RA) Managment Recommendations," *EULAR Press Release*, pp. 1-3 (2013).

"EULAR Backs MTX, DMARDs as First-Line for Early RA," *Rheumatology Network* (2013), available at http://www.rheumatologynetwork.com/news/eular-backs-mtx-dmards-first-line-early-ra, pp. 1-2, accessed on Oct. 28, 2014.

Smolen, J., et al., "EULAR Recommendation for the Management of Rheumatoid Arthritis with Synthetic and Biological Disease—Modifying Antirheumatic Drugs," *Ann Rheum Dis* 69:964-975, Lewis, England (2010).

Nam, J.L., et al., "Current Evidence for the Management of Rheumatoid Arthritis with Biological Disease-Modifying Antirheumatic Drugs: A Systematic Literature Review Informing the EULAR Recommendations for the Management of RA," *Ann Rheum Dis* 69:976-986, Lewis, England (2010).

Bykerk, V., et al., "Canadian Rheumatology Association Recommendations for Pharmacological Management of Rheumatoid Arthritis with Traditional and Biologic Disease-Modifying Antirheumatic Drugs," *J Rheumatol* 39:1559-1582, Journal of Rheumatology Publishing Co, Canada (2012).

Gibofsky, A., "Combination Therapy for Rheumatoid Arthritis in the Era of Biologicals," *Hospital for Special Surgery Journal* 2:30-41, Hospital for Special Surgery, United States (2006).

Kuriya, B., et al., "Efficacy of Initial Methotrexate Monotherapy Versus Combination Therapy with a Biological Agent in Early Rheumatoid: A Meta-Analysis of Clinical and Radiographic Remission," *Ann Rheum Dis* 69(7): 1298-1304, Lewis, England (2010) (Abstract—2 pages).

Scott, D.L., "Evidence for Early Disease-Modifying in Rheumatoid Arthritis," *Arthritis Res Ther* 6:15-18, BioMed Central Ltd, United Kingdom (2004).

Breedveld, F., and Combe, B., "Understanding Emerging Treatment Paradigms in Rheumatoid Arthritis," *Arthritis Research & Therapy* 13(Suppl 1):S3: 1-10, BioMed Central Ltd, United Kingdom (2011).

Orme, M., et al., "Systematic Review and Network Meta-Analysis of Combination and Monotherapy Treatments in Disease-Modifying Antirheumatic Drug-Experienced Patients with Rheumatoid Arthritis: Analysis of American College of Rheumatology Criteria Scores 20, 50, and 70," *Biologics: Targets and Therapy* 6:429-464, Dove Medical Press Ltd, United States (2012).

Donahue, K., et al., "Drug Therapy for Rheumatoid Arthritis in Adults: An Update," *Comparative Effectiveness Reviews* 55: (2012) (Abstract—3 pages).

Zhang, B., et al., "Validation of ACR/EULAR Definition of Remission in Rheumatoid Arthritis from RA Practice: The ESPOIR Cohort," *Arthritis Research & Therapy* 14: R156, 6 pages, BioMed Central Ltd., United States (2012).

"Biomarker 14-3-3eta Reflects RA Disease Activity, Treatment Response," *Rheumatology Network* Jul. 2, 2013, available at http://www.rheumatologynetwork.com/eular-2013/biomarker--14-3-3eta-reflects-ra-disease-activity-treatment-response, pp. 1-2, accessed on Oct. 28, 2014.

"The 2010 ACR-EULAR Classification Criteria for Rheumatoid Arthritis," American College of Rheumatology (2910), available at http://rheumatology.org/ACR/practice/clinical/classigication/ra/ra_2010.asp, pp. 1-2, accessed on Jul. 30, 2013.

"2010 RA Classification—Tree," (figure found in *Arthritis Rheum* 62: 2569-81 (2010)), *American College of Rheumatology*, available at https://www.rheumatology.org/practice/clinical/classification/ra/ratree_2010.asp, p. 1, accessed on Oct. 28, 2014.

Aletaha, D., et al., "2010 Rheumatoid Arthritis Classification Criteria," *Arthritis & Rheumatism* 62(9):2569-2581, American College of Rheumatology, United States (2010).

Aletaha, D., et al., "2010 Rheumatoid Arthritis Classification Criteria: an American College of Rheumatology/European League Against Rheumatism Collaborative Initiative," *Ann Rheum Dis* 69:1580-1588, Lewis, England (2010).

Berglin, E. and Dahlqvist, S.R., "Comparison of the 1987 ACR and 2010 ACR/EULAR Classification Criteria for Rheumatoid Arthritis in Clinical Practice: A Prospective Cohort Study," *Scandinavian Journal of Rheumatology* 42(5):362-368, (2013) (Abstract—2 pages).

Vonkeman, H.E., and Van De Laar, M., "The New European League Against Rheumatism/American College of Rheumatology Diagnostic Criteria for Rheumatoid Arthritis: How are they Performing?" *Current Opinion in Rheumatology* 25(3): 354-359, Lippincott Williams & Wilkins, United States (2013) (Abstract—1 page).

Cader, M.Z., et al., "Performance of the 2010 ACR/EULAR Criteria for Rheumatoid Arthritis," *Ann Rheum Dis* 70(6):949-955, Lewis, England (2011).

Rituxan (rituximab) FDA Product Label, 1 page (2013).

Orencia (abatacept) FDA Product Label, 1page (2011).

Actemra® (tocilizumab) FDA Product Label, 3 pages, (2013).

Remicade (infliximab) FDA Product Label, 1 page (2013).

Humira (adalimumab) FDA Product Label, 1 page (2013).

Enbrel® (etanercept) FDA Product Label, 1 page (2013).

Simponi (golimumab) FDA Product Label, 1 page (2013).

Cimzia (certolizumab pegol) FDA Product Label, 1 page (2012).

Azulfidine En-tabs®, sulfasalazine delayed release tablets, Label, 1 page.

Arava™ (leftunomide) Tablets Label, 2 pages.

Methotrexate Sodium Tablets Label, 2 pages.

Xeljanz® (tofacitinib) FDA Product Label, 6 pages (2012).

Kavanaugh, A., "Guidelines in Rheumatology: quo vadis?" *Nat Rev Rheum* 5:423-424, Nature Publishing Group, United States (2009).

Bridges, S.L., "Personalized Medicine in Rheumatoid Arthritis, Hopes and Challenges," *Bull NYU Hosp Jt Dis.* 65(3):174-177, J. Michael Ryan Publishing Co., United States (2007).

Burgos, P.I., et al., "Understanding Personalized Medicine in Rheumatoid Arthritis: A Clinician's Guide to the Future," *Ther Adv Musculoskel Dis* 1(2):97-105, Sage Publications, England (2009).

Cchandrashekara, S., and Sachin, S., "Measures in Rheumatoid Arthritis: Are We Measuring Too Many Parameters," *International Journal of Rheumatic Diseases* 15:239-248, Blackwell Publishing, England (2012).

Eastman, P.S., et al., "Characterization of a Multiplex 12-Biomarker Test for Rheumatoid Arthritis," *Journal of Pharmaceutical and Biomedical Analysis* 70: 415-424, Elsevier B.V., Netherlands (2012).

Emery, P., and Dörner, T., "Optimizing Treatment in Rheumatoid Arthritis: A Review of Potential Biological Markers of Response," *Ann Rheum Dis* 70(12):2063-2070, Lewis, England (2011) (Abstract—1 page).

Endler, G., et al., "Laboratory Diagnostics for Early Detection of Rheumatic Autoimmune Diseases: A Guide for the General Practitioner," *Wien Med Wochenschr* 162(21-22):454-463, Springer Verlag, Austria (2012) (Abstract—1 page).

Feist, E., and Dörner, T., "Personalized Medicine for Rheumatoid Arthritis: Serological and Clinical Patients Profiles to Optimize B and T Cell Targeted Therapy," *Z Rheumatol.* 72(1):49-58, Springer, Germany (2013) (Abstract—1 page).

Hamburg, M.A., and Collins, F.S., "The Path to Personalized Medicine," *The New England Journal of Medicine* 363(4):301-304, Massachusetts Medical Society, United States (2010).

(56) References Cited

OTHER PUBLICATIONS

Ibrahim, I., et al., "Genetics and the Impact on Treatment Protocols in Patients with Rheumatoid Arthritis" *Expert Rev. Clin. Immunol.* 8(6):509-511, Expert Reviews, Ltd., United Kingdom (2012).

Sokka, T., and Pincus, T., "Erythrocyte sedimentation rate, C-reactive protein, or rheumatoid factor are normal at presentation in 35%-45% of patients with rheumatoid arthritis seen between 1980 and 2004: analyses from Finland and the United States," *J. Rheumatology* 36(7): 1387-1390, Journal of Rheumatology, Canada (2009) (Abstract—1 Page).

Hoffmeister, E., "Rheumatoid Arthritis Treatment Algorithm Proposed," *Lippincott's Bone and Joint Newsletter* 19(2):13, 16-17, Lippincott Williams & Wilkins, United States (2013).

Plenge, R.M., Bridges, S.L., "Personalized Medicine in Rheumatoid Arthritis: Miles to Go Before We Sleep," *Arthritis & Rheumatism* 63(3):590-593, American College of Rheumatology, United States (2011).

Sanayama, Y., et al., "Prediction of Therapeutic Responses to Tocilizumab in Patients With Rheumatoid Arthritis," *Arthritis & Rheumatology* 66(6):1421-1431, American College of Rheumatology, United States (2014).

Sizova, L., "Approaches to the treatment of early rheumatoid arthritis with disease-modifying antirheumatic drugs," *Br J Clin Pharmacol* 62(2):173-178, Blackwell Publishing Ltd., England (2008).

Szekanecz, Z., et al., "A7.20 Response to Infliximab Therapy can be Predicted using Distinct, Non-Overlapping Gene Panels of Peripheral Blood Gene Expression in Rheumatoid Arthritis and Crohn's Disease," *Ann Rheum Dis* 72:A55 (2013) (Abstract—2 pages).

Schoels, M., et al., "Evidence for treating rheumatoid arthritis to target: results of a systematic literature search," *Ann Rheum Dis* 69:638-643, BMJ Publishing Group Ltd (2010).

Van Schaardenburg, D., "Gauging rheumatoid arthritis," *The Netherlands Journal of Medicine* 70(9):389-391, Van Zuiden Communications B.V., Netherlands (2012).

Willemze, A., et al., "New biomarkers in rheumatoid arthritis," *The Netherlands Journal of Medicine* 70(9):392-399, Van Zuiden Communications B.V., Netherlands (2012).

Donahue, K.E., et al., "Systemic review: comparative effectiveness and harms of disease-modifying medications for rheumatoid arthritis," *Annals of Int. Medicine* 148(2):125-134, American College of Physicians (2008).

Kasperkovitz, P.V., et al., Rheumatoid arthritis: a heterogeneous disease evaluated by DNA-microarray technology, *Arthritis Res Ther* 6(Suppl 3): 5, BioMed Central Ltd (2004).

Wolfe, F., et al., "The disease activity score is not suitable as the sole criterion for initiation and evolution of anti-tumor necrosis factor therapy in the clinic," *Arthritis & Rheumatism* 52(2): 3873-3879, American College of Rheumatology, United States (2005).

\* cited by examiner

TREATMENT METHODS FOR RHEUMATOID ARTHRITIS

CROSS-REFERENCE TO RELATED APPLICATION

This application claims the benefit of U.S. Provisional Application No. 61/873,312, filed Sep. 3, 2013, the contents of which are fully incorporated by reference herein.

FIELD OF THE INVENTION

The present invention provides methods for the treatment of rheumatoid arthritis based on an objective selection process (algorithm).

BACKGROUND OF THE INVENTION

Rheumatoid arthritis (RA) is an autoimmune disease and is characterized by chronic inflammation and progressive destruction of joint tissue. Li et al., *Current Medical Research & Opinion* 29(1): 85-92 (2013). The presentation of the disease and its course over time are highly variable within and between individuals. The symptoms of rheumatoid arthritis may vary from joint complaints such as pain, stiffness, swelling and functional impairment to complaints such as fatigue and loss of general health.

The majority of patients also experience progressive deterioration of cartilage and bone in the affected joints, which may eventually lead to permanent disability. The long-term prognosis of rheumatoid arthritis is poor, with approximately 50% of patients experiencing significant functional disability within 10 years from the time of diagnosis. Keystone, *Rheumatology*, 44 (Suppl. 2): ii8-ii12 (2005). Life expectancy is reduced by an average of 3-10 years in rheumatoid arthritis patients. Alamanosa et al., *Autoimmun. Rev.*, 4(3): 130-136 (2005). There is also an increase in cardiovascular disease and malignancy associated with poorly controlled rheumatoid arthritis. Kaplan, *Rheum. Dis. Clin. North Am.*, 36(2): 405-426 (2010); Llorca et al., *Semin. Arthritis Rheum.*, 37(1): 31-38 (2007). See also Charles-Schoeman, *Curr. Rheum. Rep.*, 14(5): 455-462 (2012); Smolen et al., *Arthritis Res. & Therapy*, 11: 204 (2009); Gabriel, *Ann. Rheum. Dis.*, 67(Suppl 3): iii30-iii34 (2008); Gabriel, *Am. J. Med.*, 121(10 Suppl 1): S9-14 (2008); Sokka et al., *Clin. Exp. Rheumatol.*, 26(5 Suppl 51): S35-61 (2008); Naz et al., 21(5): 871-883 (2007).

Clinical management of rheumatoid arthritis requires accurate assessment of disease activity and appropriate therapeutic intervention to maintain or reduce disease. Physicians rely on a variety of indices of rheumatoid arthritis disease activity to assist in management of the disease and to guide treatment decisions to improve patient outcomes Li et al., *Current Medical Research & Opinion* 29(1): 85-92 (2013). Current treatment guidelines recommend regular assessment of disease activity. Id.

Swollen and tender joints counts are the historical standard that are used to assess and monitor patients. Id. Joint counts alone, however, are tedious, time-consuming, poorly reproducible and dependent on the skill and interpretation of the examiner. In an attempt to provide an overall clinical picture that integrates the heterogeneous manifestations of rheumatoid arthritis, additional indices have been developed that combine multiple measures into composite scores reflecting disease activity. Id. Some composite indices may include indirect markers of inflammation, such as erythrocyte sedimentation rate (ESR) and C-reactive protein (CRP), in addition to joint counts. Although these indices are informative, routine clinical practice requires a quantitative measure of disease activity that is rapid, reproducible and easily performed.

The two commonly utilized laboratory indices for inflammation, ESR and CRP, are inconsistently elevated in rheumatoid arthritis. Pincus et al., *Rheum. Dis. Clinic North Am.*, 35(4): 687-697 (November 2009). Some rheumatologists have observed that ESR and CRP level could be used guide to treatment changes, with the goal of normalization of these markers, to preserve the patient's function and prevent additional joint damage. Ten Cate et al., *Arthritis Res. Ther.* 15(1): R4 (2013); Young et al., *Rheumatol. Rehab.* 19: 14-19 (1980); Amos et al., *BMJ* 1: 195-197 (1977). Two other commonly available laboratory tests that are used as indices for rheumatoid arthritis disease activity are hemoglobin count and platelet count.

Other indices for rheumatoid arthritis disease activity include multiple continuous assessment indices, such as Disease Score Activity (DAS), Simplified Disease Activity Index (SDAI), and Clinical Disease Activity Index (CDAI). At present, 63 assessment tools have been described. Anderson et al., *Arthritis Care & Res.* 64(5): 640-647 (2012). These tools, however, have variable accuracy and precision. Wolfe et al., *Arthritis & Rheumatism* 52(12): 3873-3879 (2005).

The traditional treatment of rheumatoid arthritis follows a regimented pattern, based on historical clinical trials. In recent years, the treatment philosophy has shifted to a "treat to target" approach, which reflects the awareness of the importance of biochemically neutralizing or suppressing the inflammatory processes to prevent joint damage and disability. In the last decade, there have been studies on individual biomarkers in small populations of patients with rheumatoid arthritis (e.g., measuring proteins or chemicals that contribute to inflammation) that measure the impact of treatment on individual biomarkers. Several biomarkers have also been used as an index for rheumatoid arthritis disease activity. However, the use of these biomarkers to measure rheumatoid disease activity was not applicable in a clinical setting until VECTRA® DA test by Crescendo Bioscience, Inc. became commercially available in 2010.

The VECTRA® DA test has made it possible to commercially use biomarkers to assess rheumatoid disease activity in each patient. The VECTRA® DA test measures various biomarkers that are known to play a role in rheumatoid arthritis, such as cytokines, receptors, adhesion molecules, growth factors, matrix metalloproteinases, skeletal-related proteins, hormones, and acute-phase proteins, and provides quantitative scores that correspond to disease activity. Eastman et al., *J. Pharma. & Biomedical Analysis* 70: 414-424 (2012).

The current "treat to target" philosophy (attempting to treat to reduce the inflammation) is blind. The practicing clinician often arbitrarily picks and changes treatments to achieve the desired goal or follows prescribed regimens that do not take into account the unique biochemical and pathophysiological characteristics of an individual patient. For example, the American College of Rheumatology has developed guidelines for the treatment of rheumatoid and juvenile chronic arthritis based on the outcomes of clinical trials. Singh et al., *Arthritis Care & Research* 64(4): 625-639 (2012); Beukelman et al., *Arthritis Care & Research* 63(4): 465-482. None of the guidelines utilize the unique biochemical physiology (disturbance) of each patient to select a treatment, and remissions have been difficult to achieve. See Zhang et al., *Arthritis Res. & Therapy*, 14: R156 (2012); Felson et al., *Arthritis & Rheumatism*, 63(3): 573-586 (2011); Ma et al., *The J. of Rheum.*, 37(7): 1444-1453 (2010).

Additionally, with an increasingly higher number of new drugs in development, it will be progressively more difficult to select initial and subsequent treatments without an objective insight into the unique biochemical and pathophysiological characteristics of each patient. At present, one cannot predict which patient is likely to respond to a particular treatment, thus leading to a considerable trial and error, usually at considerable risk, expense, and discomfort of the patient.

It has been previously speculated that targeted therapies against newly identified biomarkers would lead to improved outcomes. Vilcek et al., *Trends Pharm. Sci.* 25(4): 201-209 (2004); Canella et al., *Drugs* 66(10): 1319-1337 (2006); Feely et al., *Expert Opin. Pharmacother.* 10(13): 2095-2106 (2009); Dale et al., *Best Prac. Res. Clin. Rhematol.* 24(4): 443-455 (2010); Allart et al., *Curr. Opin. Rheu.* 23(3): 421-244 (2011); Smolen et al., *Nat. Rev. Drug Discov* 2(6): 473-488 (2003). But, many of the targets, direct or indirect, were not commercially available until the VECTRA® DA test became available in the market.

Accordingly, there is an unmet need for a method for an objective selection of a treatment method for rheumatoid arthritis that is personalized for each patient and is based on individual patient's biochemical and pathophysiological characteristics. There is a need for more effective means for determining which patients will respond to which treatment and for incorporating such determinations into more effective treatment regimens for rheumatoid arthritis patients. Gibofsky et al., *Ann. Rheum. Dis.,* 69(6): 941-942 (2010); Kavanaugh, *Rheumatology,* 5: 423-424 (2009).

The entire contents of all references cited herein are hereby incorporated by reference.

BRIEF SUMMARY OF THE INVENTION

The present invention provides an objective selection of treatment methods for rheumatoid arthritis (e.g. an algorithm), and methods for treatment of rheumatoid arthritis by applying the selected treatment methods. The selected treatment methods of the invention focus on an individual patient's unique biochemical and pathophysiological characteristics reflected by a unique biomarker pattern.

After conducting a thorough analyses of the previous approaches for treatment of rheumatoid arthritis and conducting lengthy research on treatment outcomes, the inventor recognized the importance of providing an objective methodology for the selection of treatment methods. The invention arose out of an understanding that there is a correlation between response of certain biochemical and pathophysiological markers (biomarkers) to a treatment method and ultimate outcome of treatment using the treatment method.

When a patient presents with symptoms or complaints indicative of rheumatoid arthritis, the method of the invention comprises determining levels of biomarkers in a sample taken from the patient and comparing the biomarker levels in the patient sample with their corresponding levels in a control sample. If the level of a biomarker in the patient sample is altered (increased or decreased) by at least 40% compared to its level in the control sample, then the biomarker is identified as a biomarker that can be used to select a treatment method for the patient. If the level of a biomarker in the patient sample is not altered by at least 40% compared to its level in the control sample, then the biomarker is not used to select a treatment method for the patient.

After the biomarkers with at least 40% altered level are identified, at least two biomarkers (each one of which has its level in the patient sample altered by at least 40% compared to the control sample) are selected and used to select a treatment method that is known to affect the selected biomarkers. The selected treatment method is then administered to the patient.

In some aspects, the present invention provides an algorithm that determines levels of biomarkers that are known to be affected or altered (increased or decreased) in rheumatoid arthritis, identifies the biomarkers with altered (increased or decreased) levels in a patient sample compared to a control sample, and selects a treatment method that affects the biomarkers with the altered levels.

In other aspects, the present invention provides methods for treating a patient with rheumatoid arthritis, wherein the method comprises determining levels of at least two biomarkers that are known to be affected or altered (increased or decreased) in rheumatoid arthritis in a patient sample, selecting a treatment method based on the levels of at least two biomarkers in the sample, and administering the selected treatment method to the patient with rheumatoid arthritis.

In one aspect, the present invention provides a method for treating a patient with rheumatoid arthritis, wherein the method comprises: (i) determining serum levels in the patient of at least two biomarkers selected from the group consisting of Vascular Cell Adhesion Molecule-1 (VCAM-1), Vascular Endothelial Growth Factor-A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP); (ii) identifying at least two biomarkers each one with at least 40% elevated serum level over control serum level; (iii) selecting at least one treatment method that is known to affect the at least two biomarkers identified in step (ii); and (iv) administering the treatment method selected in step (iii) to the patient.

In a second aspect, the present invention provides a method for treating a patient with rheumatoid arthritis, wherein the method comprises: (i) determining serum levels in the patient of at least two biomarkers selected from the group consisting of Vascular Cell Adhesion Molecule-1 (VCAM-1), Vascular Endothelial Growth Factor-A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP); (ii) identifying at least two biomarkers each one with at least 40% elevated serum level over control serum level; (iii) selecting at least one treatment method that is known to affect the at least two biomarkers identified in step (ii), wherein the treatment method is selected from the group consisting of PLAQUENIL (or Hydroxychloroquine), Sulfasalazine, Methotrexate, ARAVA (or Leflunomide), Tumor Necrosis Factor-α inhibitors, Atabacept (or ORENCIA), Tocilizumab (or ACTEMRA), RITUXAN (or Rituximab), and Tofacitinib (or XELJANZ); and (iv) administering the treatment method selected in step (iii) to the patient.

In a third aspect, the present invention provides a method for treating a patient with rheumatoid arthritis, wherein the method comprises: (i) determining serum levels in the patient of at least two biomarkers selected from the group consisting of Vascular Cell Adhesion Molecule-1 (VCAM-1), Vascular Endothelial Growth Factor-A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP); (ii) identifying at least two biomarkers each one with at least 40% elevated serum level over control serum level; (iii) selecting a first treatment method that is known to affect the at least two biomarkers identified in step (ii), wherein the treatment method is selected from the group consisting of PLAQUENIL (or Hydroxychloroquine), Sulfasalazine, Methotrexate, ARAVA (or Leflunomide), Tumor Necrosis Factor-α inhibitors, Atabacept (or ORENCIA), Tocilizumab (or ACTEMRA), RITUXAN (or Rituximab), and Tofacitinib (or XELJANZ); (iv) administering the first treatment method selected in step (iii) to the patient; and (v) determining effectiveness or ineffectiveness of the first treatment method administered in step (iv) to the patient.

In a fourth aspect, the present invention provides a method for treating a patient with rheumatoid arthritis, wherein the method comprises: (i) determining serum levels in the patient of at least two biomarkers selected from the group consisting of Vascular Cell Adhesion Molecule-1 (VCAM-1), Vascular Endothelial Growth Factor-A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP); (ii) identifying at least two biomarkers each one with at least 40% elevated serum level over control serum level; (iii) selecting a first treatment method that is known to affect the at least two biomarkers identified in step (ii), wherein the treatment method is selected from the group consisting of PLAQUENIL (or Hydroxychloroquine), Sulfasalazine, Methotrexate, ARAVA (or Leflunomide), Tumor Necrosis Factor-α inhibitors, Atabacept (or ORENCIA), Tocilizumab (or ACTEMRA), RITUXAN (or Rituximab), and Tofacitinib (or XELJANZ); (iv) administering the first treatment method selected in step (iii) to the patient; and (v) determining effectiveness or ineffectiveness of the first treatment method administered in step (iv) to the patient; (vi) selecting a second treatment method, and (vii) administering the second treatment method selected in step (vi) to the patient.

In some aspects, the determining in (v) comprises: (i) determining VECTRA DA Score, C-Reactive Protein (CRP) level, and Erythrocyte Sedimentation Rate (ESR) in the patient before and after the first treatment method; and (ii) comparing the VECTRA DA Score, CRP level, and ESR in the patient before and after the first treatment method. In other aspects, the determining in (v) comprises: (i) determining one or more selected from the group consisting of VECTRA DA Score, CRP level, and Sedimentation Rate in the patient before and after the first treatment method; and (ii) comparing the one or more selected from the group consisting of VECTRA DA Score, CRP level, and Erythrocyte Sedimentation Rate in the patient before and after the first treatment method. In some aspects, the selecting the second treatment method in (vi) comprises (i) identifying at least two biomarkers selected from the group consisting of Vascular Cell Adhesion Molecule-1 (VCAM-1), Vascular Endothelial Growth Factor-A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP), each one with at least 40% elevated serum level over control serum level; and (ii) selecting a second treatment method that is known to affect the at least two biomarkers identified in step (ii) in [0024], wherein the treatment method is selected from the group consisting of PLAQUENIL (or Hydroxychloroquine), Sulfasalazine, Methotrexate, ARAVA (or Leflunomide), Tumor Necrosis Factor-α inhibitors, Atabacept (or ORENCIA), Tocilizumab (or ACTEMRA), RITUXAN (or Rituximab), and Tofacitinib (or XELJANZ).

In some aspects, the selecting in step (iii) further comprises selecting a treatment method that is known to affect the maximum number of biomarkers identified in step (ii). In other aspects, the selecting in step (iii) further comprises selecting a treatment method that is known to affect the maximum number of the highest elevated biomarkers.

In other aspects, the selecting in step (iii) further comprises avoiding a treatment method that is contraindicated or causes an allergic response in the patient. In some aspects, the selecting in step (iii) further comprises selecting a treatment method that is administered via a route selected from the group consisting of intravenous, intraarterial, enteral (oral or rectal), intramuscular, subcutaneous, transdermal, intradermal, nasal, intramuscular, intraperitoneal, intracardiac, epidural, intrathecal, and transmucosal. In other aspects, the selected route is preferred by the patient. In some aspects, the selecting in step (iii) comprises selecting a treatment method that is required under the patient's medical plan. In other aspects, the selecting in step (iii) comprises selecting a treatment method that fits with the patient's social and work circumstances. In another aspect, the selecting in step (iii) comprises selecting a treatment method based on the patient's preference for older or newer treatment methods. In other aspects, the selecting in step (iii) comprises using any combination of the selection options in any order.

DETAILED DESCRIPTION OF THE INVENTION

Figure 1:
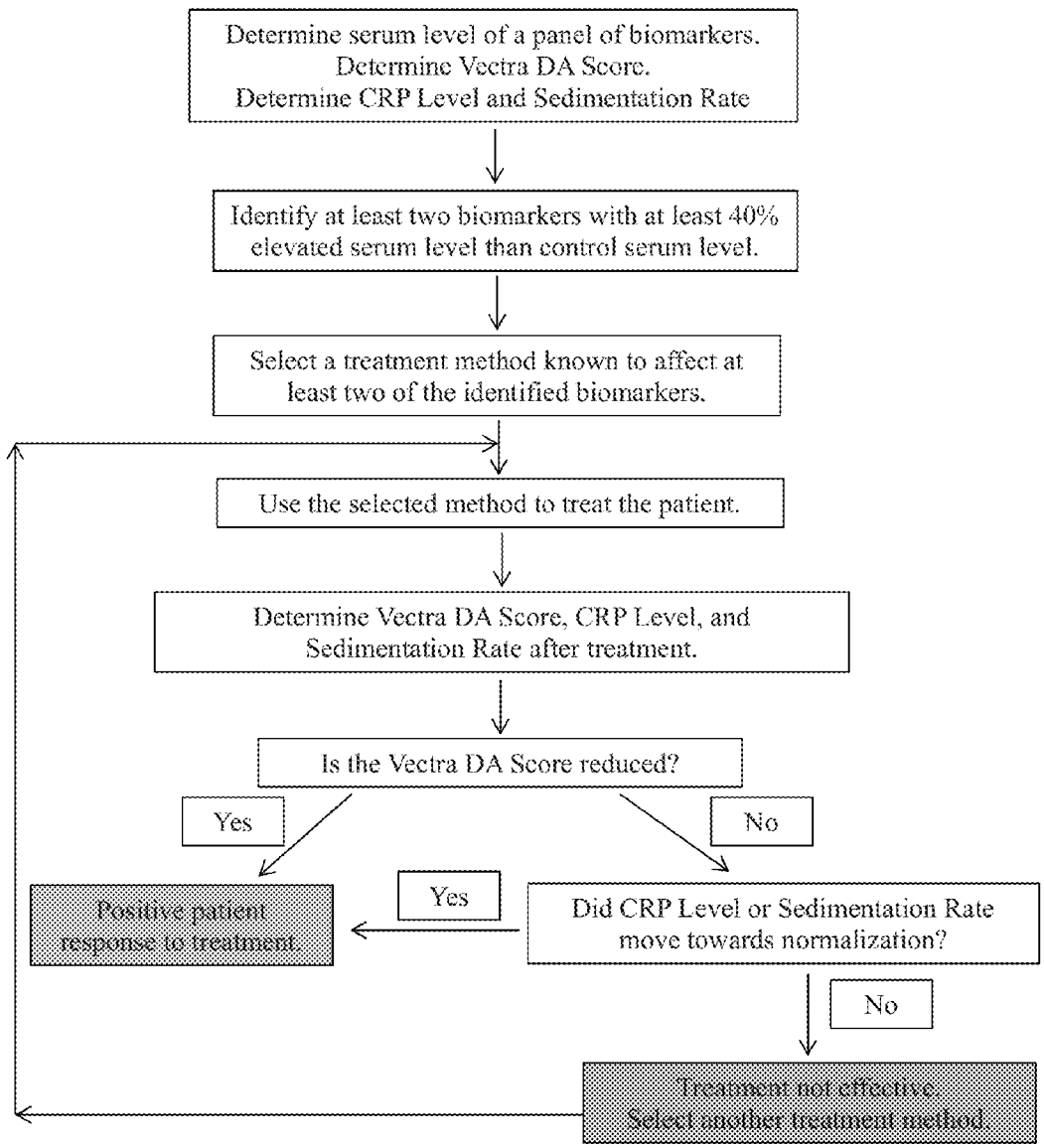
FIG. 1 shows an embodiment of a method for treating rheumatoid arthritis by a treatment method selected based on an objective selection method (algorithm).
Figure 2:
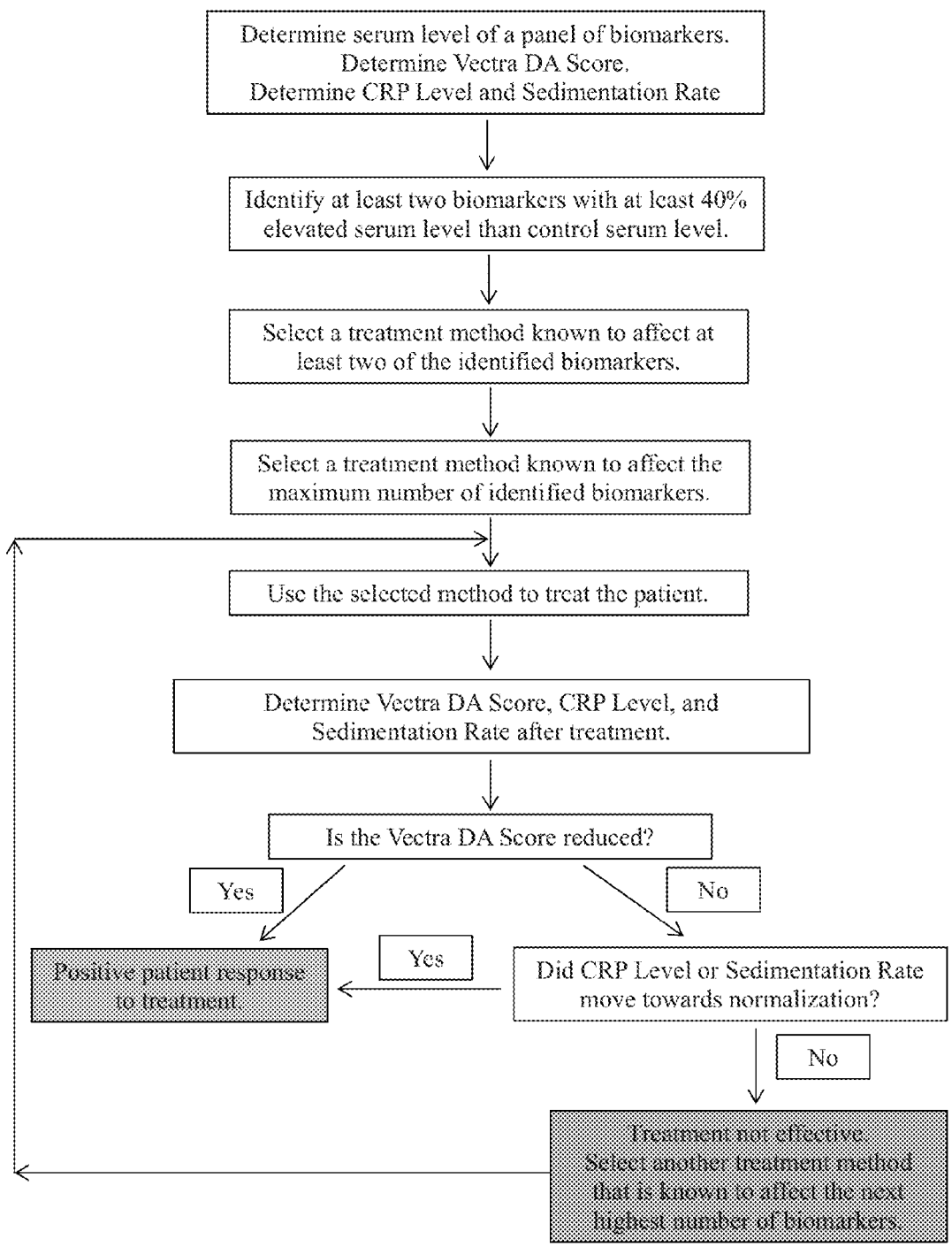
FIG. 2 shows a second embodiment of a method for treating rheumatoid arthritis by a treatment method selected based on an objective selection method (algorithm).
Figure 3:
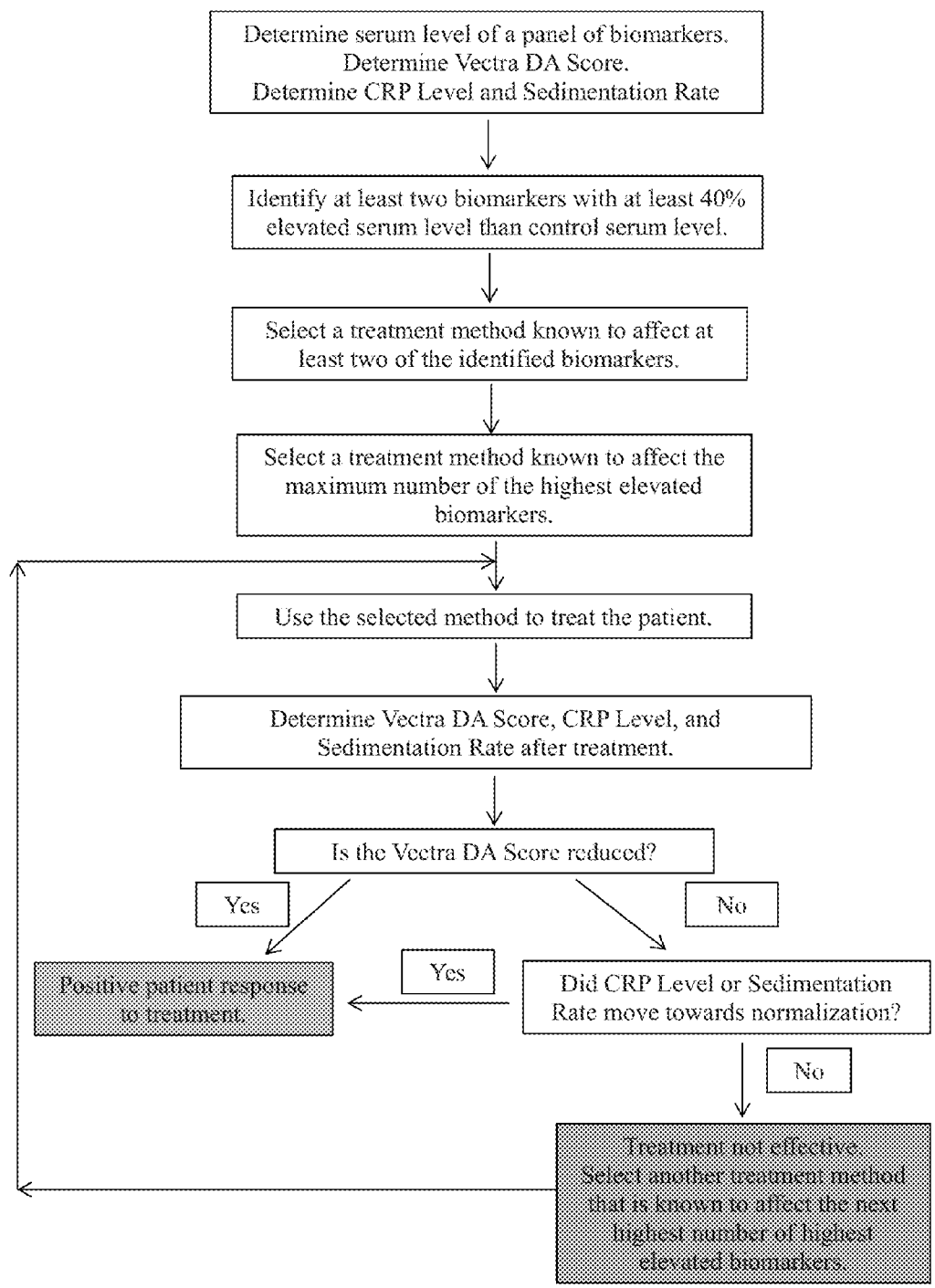
FIG. 3 shows a third embodiment of a method for treating rheumatoid arthritis by a treatment method selected based on an objective selection method (algorithm).
Figure 4:
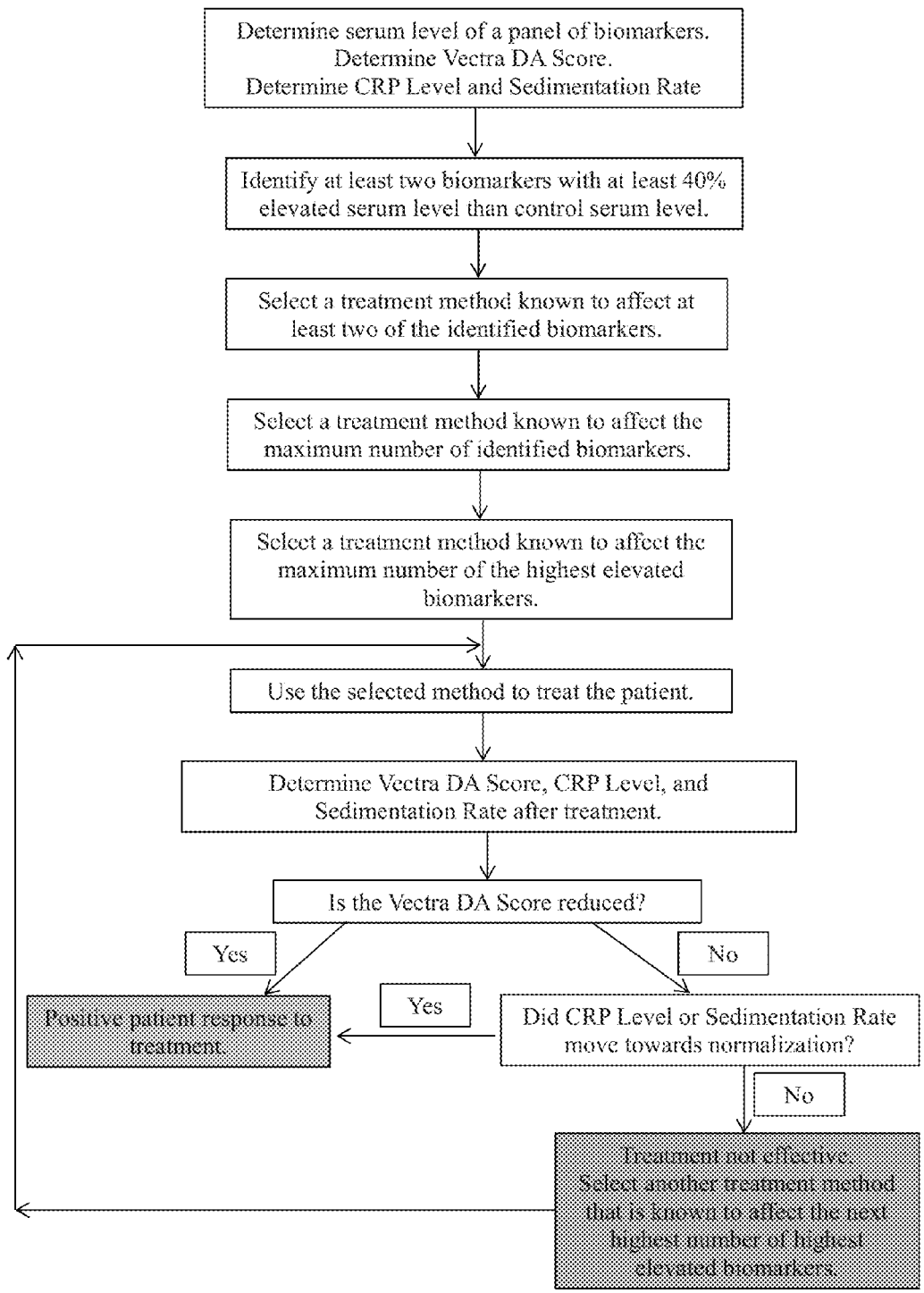
FIG. 4 shows a fourth embodiment of a method for treating rheumatoid arthritis by a treatment method selected based on an objective selection method (algorithm).
Figure 5:
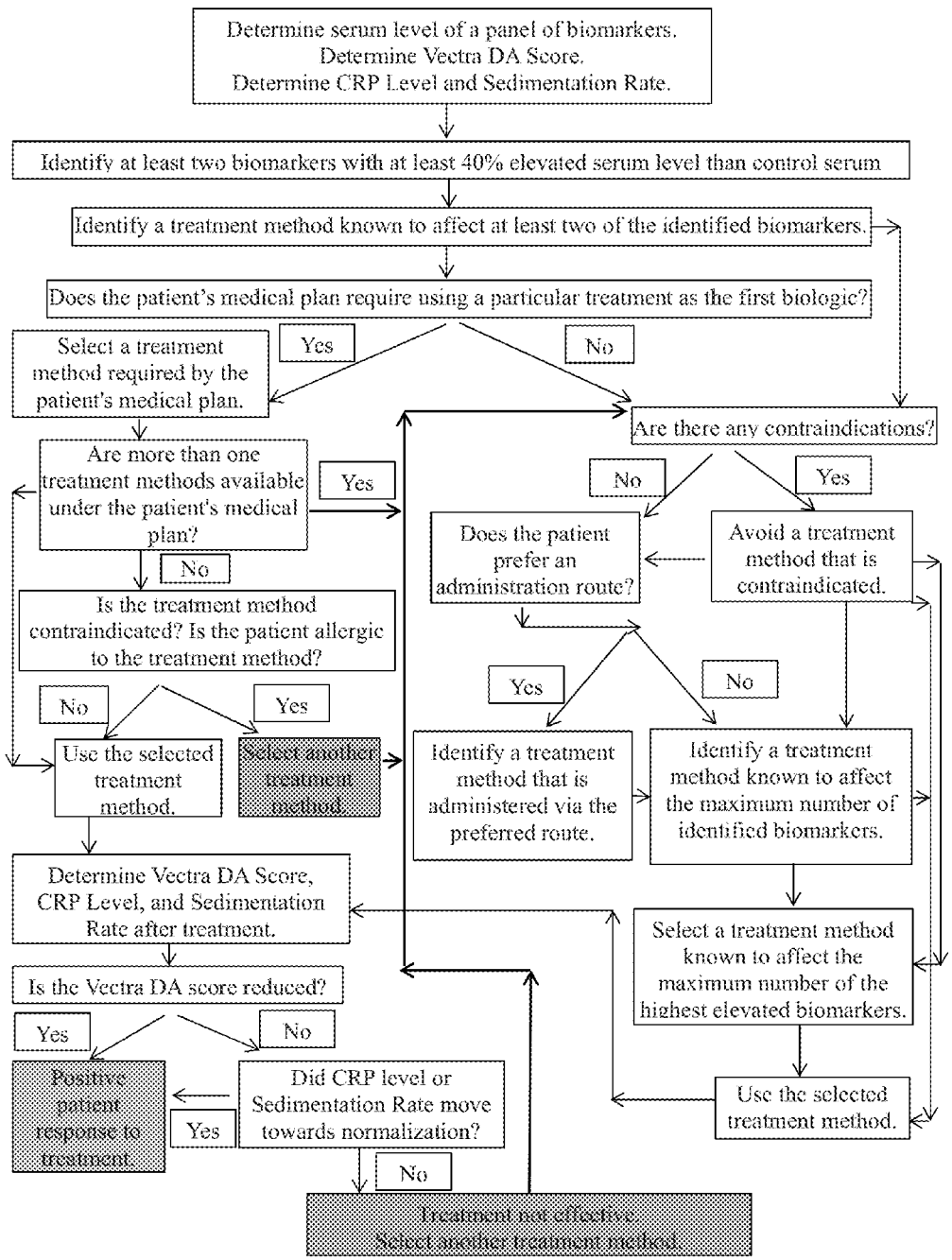
FIG. 5 shows various embodiments of a method for treating rheumatoid arthritis by a treatment method selected based on an objective selection method (algorithm).

The present invention provides methods for selecting treatment methods for rheumatoid arthritis based on an objective selection method (algorithm) and provides methods for treatment of rheumatoid arthritis using the selected treatment method.

It must be noted that, as used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Unless defined otherwise, numeric ranges are inclusive of the numbers defining the range. The headings provided herein are not limitations of the various aspects or embodiments of the invention, which can be had by reference to the specification as a whole. One skilled in the art will recognize many methods and materials similar or equivalent to those described herein, which could be used in the practice of the present invention. Indeed, the present invention is in no way limited to the methods and materials described. For purposes of the present invention, the following terms are defined below. The terms defined immediately below are more fully defined by reference to the specification in its entirety.

DEFINITIONS

The terms "rheumatoid arthritis" or "RA" as used herein refer to a recognized disease state that may be diagnosed according to the 2000 revised American Rheumatoid Association criteria for the classification of rheumatoid arthritis, or any similar criteria. The term includes not only active and early rheumatoid arthritis, but also incipient rheumatoid arthritis, as defined below. Rheumatoid arthritis includes, for example, juvenile-onset RA, juvenile idiopathic arthritis (JIA), or juvenile RA (JRA).

A patient with "active rheumatoid arthritis" means a patient with active and not latent symptoms of rheumatoid arthritis. Subjects with "early active rheumatoid arthritis" are those subjects with active rheumatoid arthritis diagnosed for at least 8 weeks but no longer than four years, according to the revised 1987 ACR criteria for the classification of rheumatoid arthritis. Subjects with "early rheumatoid arthritis" are those subjects with rheumatoid arthritis diagnosed for at least eight weeks but no longer than four years, according to the revised 1987 ACR criteria for classification of rheumatoid arthritis.

Patients with "incipient RA" have early polyarthritis that does not fully meet ACR criteria for a diagnosis of rheumatoid arthritis, in association with the presence of RA-specific prognostic biomarkers such as anti-CCP and shared epitope. They include patients with positive anti-CCP antibodies who present with polyarthritis, but do not yet have a diagnosis of rheumatoid arthritis, and are at high risk for going on to develop bona fide ACR criteria rheumatoid arthritis (95% probability).

The terms "disease activity" or "rheumatoid arthritis disease activity" as used herein refer to severity or intensity of rheumatoid arthritis and can be determined by using various indices known in the art, such as DAS, DAS28, ESR, CRP level, various biomarker levels, and VECTRA DA Score.

The terms "treat," "treatment," "treatment of" or "treating" (e.g., in the phrase "treating a patient with rheumatoid arthritis") used herein refer to reducing the potential for rheumatoid arthritis, reducing the occurrence of the rheumatoid arthritis, and/or a reduction in the severity of rheumatoid arthritis, preferably, to an extent that the subject no longer suffers discomfort and/or altered function due to it. For example, treating can refer to the ability of a therapy, when administered to a subject, to prevent rheumatoid arthritis from occurring and/or to cure or to alleviate rheumatoid arthritis symptoms, signs, or causes. Treating also refers to mitigating or decreasing at least one disease activity index and/or clinical symptom and/or inhibition or delay in the progression of the condition and/or prevention or delay of the onset of a disease or illness. The terms "treat," "treating" or "treatment of" (or grammatically equivalent terms) refer to both prophylactic and therapeutic treatment regimes.

Those in need of treatment include those already with rheumatoid arthritis or joint damage as well as those in which rheumatoid arthritis or joint damage or the progress of rheumatoid arthritis or joint damage is to be prevented. Hence, the subject may have been diagnosed as having the rheumatoid arthritis or joint damage or may be predisposed or susceptible to the RA or joint damage, or may have rheumatoid arthritis or joint damage that is likely to progress in the absence of treatment.

The term "therapy" as used herein includes any means for curing, mitigating, or preventing rheumatoid arthritis, including, for example, therapeutic agents, instrumentation, supportive measures, and surgical or rehabilitative procedures. In this respect, the term therapy encompasses any protocol, method and/or therapeutic or diagnostic agent that can be used in prevention, management, treatment, and/or amelioration of rheumatoid arthritis. In some aspects, the term "therapy" refers to administering a therapeutically effective amount of a therapeutic agent that is capable of treating the patient.

The terms "treatment method" or "therapeutic agent" as used herein refer to any therapeutically active substance that is administered to a subject having rheumatoid arthritis to produce a desired, preferably beneficial, effect. The terms "treatment method" or "therapeutic agent" includes drugs, peptides, lipids, protein drugs, protein conjugate drugs, enzymes, oligonucleotides, ribozymes, genetic material, prions, virus, bacteria, and eukaryotic cells. A therapeutic agent can also be a pro-drug, which metabolizes into the desired therapeutically active substance when administered to a subject. In addition, a therapeutic agent can be pharmaceutically formulated. A therapeutic agent can also be a radioactive isotope or agent activated by some other form of energy such as light or ultrasonic energy, or by other circulating molecules that can be systemically administered. In some aspects, the treatment method is a single treatment method. In other aspects, the treatment method is a combination of treatment methods.

The term "first treatment method" refers to a treatment method that is initially used to treat a rheumatoid arthritis patient based on the objective selection methods disclosed herein. In one embodiment, the first treatment method is a single treatment method. In another embodiment, the first treatment method is a combination of treatment methods.

The term "second treatment method" refers to a treatment method that is selected to treat rheumatoid arthritis patient based on the selection methods disclosed herein, after the first treatment method is ineffective, and is different than the first treatment method. In one embodiment, the second treatment method is a single treatment method. In another embodiment, the second treatment method is a combination of treatment methods. In one embodiment, the combination of treatment methods used as the second treatment method comprises one or more treatment methods that were previously used to treat the patient.

A "therapeutically effective amount" or "effective amount" as used herein refers to an amount of a treatment method/therapeutic agent that is effective for treating rheumatoid arthritis or joint damage, or provides some improvement or benefit to a subject having rheumatoid arthritis. Thus, a "therapeutically effective" amount is an amount that provides some alleviation, mitigation, and/or decrease in at least one clinical symptom of rheumatoid arthritis. Clinical symptoms associated with rheumatoid arthritis that can be treated by the methods of the invention are well-known to those skilled in the art. Further, those skilled in the art will appreciate that the therapeutic effects need not be complete or curative, as long as some benefit is provided to the subject. In some aspects, the term "therapeutically effective" refers to an amount of a therapeutic agent that is capable of achieving a reduction in rheumatoid arthritis or joint damage as compared to baseline prior to administration of such amount as determined by one of the known indices of disease activity.

A "sufficient amount" or "an amount sufficient to" achieve a particular result in a patient having rheumatoid arthritis refers to an amount of a therapeutic agent that is effective to produce a desired effect, which is optionally a therapeutic effect (i.e., by administration of a therapeutically effective amount).

The terms "subject" or "patient" as used herein refer to any subject, particularly a mammalian subject, for whom diagnosis, prognosis, or therapy of rheumatoid arthritis is desired. As used herein, the terms "subject" or "patient" include any human or nonhuman animal. The term "nonhuman animal" includes all vertebrates, e.g., mammals and non-mammals, such as nonhuman primates, sheep, dogs, cats, horses, cows, bears, chickens, amphibians, reptiles, etc. As used herein, phrases such as "a patient with rheumatoid arthritis" includes subjects, such as mammalian subjects, that would benefit from the administration of a therapy, diagnostic procedure, and/or preventive treatment for rheumatoid arthritis. Most preferably, the patient is a human.

In some aspects of the present invention, a subject is a naïve subject. A naïve subject is a subject that has not been administered a therapy, for example a therapeutic agent. In some aspects, a naïve subject has not been treated with a therapeutic agent prior to being diagnosed as having rheumatoid arthritis.

In some aspect, a subject has previously received therapy and/or one or more doses of a therapeutic agent prior to being treated with a treatment selected based on the selection method (algorithm) described herein. In one aspect, the previously received therapy was not selected based on the algorithm described herein. In another aspect, the previously received therapy was selected based on the algorithm described herein.

The term "sample" as used herein includes any biological fluid or tissue, such as whole blood, serum, muscle, saliva, urine, synovial fluid, bone marrow, cerebrospinal fluid, nasal secretions, sputum, amniotic fluid, bronchoalveolar lavage fluid, peripheral blood mononuclear cells, total white blood cells, lymph node cells, spleen cells, tonsil cells, or skin. In some specific aspects, that sample is blood or a fraction thereof, muscle, skin, or a combination thereof. Samples can be obtained by any means known in the art. For example, "serum sample" as used herein is e.g., a serum sample obtained from an individual. Methods for obtaining serum from individuals are well known in the art.

The terms "patient sample," "test sample," or "samples from a patient" as used herein refer to a sample obtained from a patient. In order to apply the methods of the invention, samples from a patient can be obtained before or after the administration of a therapy to treat rheumatoid arthritis. In some cases, successive samples can be obtained from the patient after therapy has commenced or after therapy has ceased. Samples can, for example, be requested by a healthcare provider (e.g., a doctor, nurse, hospital) or healthcare benefits provider, obtained and/or processed by the same or a different healthcare provider or a clinical laboratory, and after processing, the results can be forwarded to same or yet another healthcare provider, healthcare benefits provider or the patient. Similarly, the measuring/determining of one or more scores, comparisons between scores, evaluation of the scores and treatment decisions can be performed by one or more healthcare providers, healthcare benefits providers, and/or clinical laboratories.

A "control" or "control sample" includes a sample obtained from an individual for use in determining base-line or normal level of a biomarker. Accordingly, a control may be obtained by a number of means, including from individuals not affected by a rheumatoid arthritis (as determined by standard techniques) or from an individual not suspected of being at risk for rheumatoid arthritis. A control also includes a previously established standard. For example, in VECTRA® DA test, the control is a reference set of rheumatoid arthritis patients from a study (InFoRM study). Accordingly, any test or assay conducted according to the invention may be compared with the established standard and it may not be necessary to obtain a control sample for comparison each time.

As used herein, the term "healthcare provider" refers to individuals or institutions that directly interact and administer therapy to subjects, e.g., human patients. Non-limiting examples of healthcare providers include clinicians, doctors, nurses, technicians, therapist, pharmacists, counselors, alternative medicine practitioners, medical facilities, doctor's offices, hospitals, emergency rooms, clinics, urgent care centers, alternative medicine clinics/facilities, formularies, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

In some aspects, a healthcare provider can administer or instruct another healthcare provider to administer a therapy to treat rheumatoid arthritis. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapy, commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent.

The term "healthcare benefits provider" as used herein encompasses individual parties, organizations, or groups providing, presenting, offering, paying for in whole or in part, or being otherwise associated with giving a patient access to one or more healthcare benefits, benefit plans, health insurance, and/or healthcare expense account programs.

In some aspects, a healthcare benefits provider can authorize or deny, for example, collection of a sample, processing of a sample, submission of a sample, receipt of a sample, transfer of a sample, analysis or measurement a sample, quantification a sample, provision of results obtained after analyzing/measuring/quantifying a sample, transfer of results obtained after analyzing/measuring/quantifying a sample, comparison/scoring of results obtained after analyzing/measuring/quantifying one or more samples, transfer of the comparison/score from one or more samples, administration of a therapy or therapeutic agent, commencement of the administration of a therapy or therapeutic agent, cessation of the administration of a therapy or therapeutic agent, continuation of the administration of a therapy or therapeutic agent, temporary interruption of the administration of a therapy or therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapy or therapeutic agent by at least another therapy or therapeutic agent, or combine a therapy or therapeutic agent with at least another therapy or additional therapeutic agent. In addition a healthcare benefits provides can, e.g., authorize or deny the prescription of a therapy, authorize or deny coverage for therapy, authorize or deny reimbursement for the cost of therapy, determine or deny eligibility for therapy, etc.

The terms "medical plan" or "patient's medical plan" or "benefit plan" as used herein refer to health care benefits that are available to a patient through a health care benefits provider.

The term "biomarker" as used herein refers to an indicator of pathophysiological state of a patient, which can be affected in response to therapy. Examples of biomarkers include, but are not limited to, a DNA, RNA, protein, carbohydrate, or glycolipid-based molecular marker. The expression or presence of a biomarker in a sample can be detected by standard methods (or methods disclosed herein) and can be predictive and/or prognostic of the responsiveness of an rheumatoid arthritis patient to a treatment method. In one aspect, a biomarker is a protein that is affected or altered (increased or decreased) in rheumatoid arthritis. In another aspect, a biomarker is a protein that correlates with rheumatoid arthritis disease activity. Biomarkers contemplated by the present invention are Vascular Cell Adhesion Molecule 1 (VCAM-1), Epidermal Growth Factor (EGF), Vascular Endothelial Growth Factor A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP). In some aspects, a biomarker is present in a test sample and is not present in a control or reference, or is present at a particular amount or concentration or level in the test sample that differs from its level in the control. In another aspect, the expression of such a biomarker in the test sample is determined to be higher than that observed in a control.

In some embodiments, a biomarker is detected before, during, and/or after the administration of a therapeutic agent to a patient. In some embodiments, a biomarker provides the basis for an assay that aids in determining the dosing and regimen, identifying patient subgroups or phenotypes that are responsive to the treatment method/therapeutic agent, or selecting a treatment method/therapeutic agent for treatment. In one aspect, a biomarker is used to monitor treatment in the patients. In another aspect, a biomarker is utilized to determine rheumatoid arthritis disease activity.

A biomarker is understood to be positively affected by a treatment method (i.e., a biomarker is understood to have a favorable response to a treatment method) when the biomarker level moves towards its normal level after treatment with the treatment method (normalization). A biomarker is understood to be not positively affected by treatment method (i.e., a biomarker is understood to have an unfavorable response to a treatment method) when biomarker level does not move towards its normal level after treatment with the treatment method.

The term "concentration," "amount," or "level" of a biomarker is an amount or concentration of the biomarker in a sample. These can be measured by methods known to the ordinarily skilled person in the art and also disclosed by this invention. The concentration or amount or level of a biomarker assessed can be used to determine the disease activity and response to a treatment method.

The term "serum level" as used herein refers to the amount or concentration of a biomarker in serum of a patient.

The term "control serum level" as used herein refers to the amount or concentration of a biomarker in serum of a control. Thus, the term refers to the amount or concentration of a biomarker in serum of individuals not affected by a rheumatoid arthritis or in a control group previously established as a standard. For example, in VECTRA® DA test, the control biomarker levels is the level of biomarkers in a reference set of RA patients from a study (InFoRM study).

The terms "Vascular Cell Adhesion Molecule 1" or "VCAM-1" is a protein encoded by VCAM1 gene in humans. VCAM-1 functions as a cell adhesion molecule.

The terms "Vascular Endothelial Growth Factor A" or "VEGF-A" is a protein that is encoded by VEGFA gene in humans. VEGF-A stimulates endothelial cell mitogenesis and cell migration, is involved in angiogenesis, is a vasodilator, and increases microvascular permeability.

The terms "Interleukin-6" or "IL-6" is both a pro-inflammatory and anti-inflammatory cytokine and is an important mediator of fever and acute phase response. It is encoded by IL-6 gene in humans.

The terms "Tumor necrosis factor receptor Type I" or "TNFRI" refer to cell-surface TNF receptor that is encoded by TNFRSF1A gene in humans. TNFR1 is responsible for mediation of TNF-alpha effects and is also referred to as CD120a.

The terms "Matrix Metalloproteinase-1" or "MMP-1" is a collagenase that is encoded by MMP-1 gene in humans. It is involved in breakdown of extracellular matrix in normal physiological processes and in disease processes, particularly Type I, II and III interstitial collagens. It is also known as interstitial collagenase or fibroblast collagenase.

The terms "Matrix Metalloproteinase-3" or "MMP-3" refers to an enzyme involved in breakdown of extracellular matrix during tissue remodeling in normal physiological processes or in disease processes. It is encoded by MMP3 gene in humans.

The term "YKL-40" is a glycosyl hydrolase and is an autoantigen in rheumatoid arthritis.

The term "Leptin" is an enzyme that plays a key role in regulating energy intake and expenditure including appetite and hunger, metabolism, and behavior, and functions by binding to the leptin receptor.

The term "Resistin" is a peptide hormone and is encoded by RETN gene. It is also known as adipose tissue-specific secretory factor (ADSF) or C/EBP-epsilon-regulated myeloid-specific secreted cysteine-rich protein (XCP1).

The terms "Serum Amyloid A" or "SAA" refer to a family of apolipoproteins that are associated with high density lipoprotein in plasma. Acute-phase serum amyloid A proteins (A-SAAs) are secreted during the acute phase of inflammation. A-SAAs are implicated in several chronic inflammatory diseases such as rheumatoid arthritis. Serum amyloid A (SAA) is an acute phase marker that responds rapidly to inflammatory stimuli.

The terms "C-Reactive Protein" or "CRP" refer to a protein found in blood and its levels increase in response to inflammation. It binds to phosphocholine expressed on the surface of dead or dying cells (and some types of bacteria) in order to activate the complement system.

The terms "contraindicated" or "contraindication" refer to a condition or a factor that is a reason to withhold a certain therapy or treatment method in a patient. Examples of contraindications include, but are not limited to, incompatibility of therapeutic agents; patient's allergic response to a therapeutic agent; actual contraindications, warnings and precautions listed on the FDA-mandated drug inserts; and re-activation or exacerbation of existing chronic infections.

The term "allergic response" refers to a hypersensitive immune reaction to a substance, such as a therapeutic agent, in a patient. Symptoms of an allergic response include itching, inflammation or tissue injury.

The terms "administration route" or "administered via route" or "route for administration" refer to a path by which a therapeutic agent is administered into the body.

The term "VECTRA DA Score" or "VECTRA DA MBDA Score" as used herein refers to a score obtained from an algorithm/formula that combines the concentrations of 12 serum protein biomarkers measured in VECTRA® DA test (Crescendo Bioscience, Inc.) into a single score that represents the level of rheumatoid arthritis disease activity on a scale of 1 to 100. A VECTRA DA Score of ≤29 reflects low disease activity, a VECTRA DA Score of >29 and ≤44 reflects moderate disease activity, and a VECTRA DA Score of >44 reflects high disease activity. VECTRA DA Score is provided in VECTRA DA test report.

"Clinical improvement" refers to prevention of further progress of rheumatoid arthritis or joint damage or any improvement in RA or joint damage as a result of treatment, as determined by various testing methods, the number of tender or swollen joints, a global clinical assessment of the subject, Erythrocyte Sedimentation Rate, or C-Reactive Protein level.

A subject is in "remission" if he/she has no symptoms of rheumatoid arthritis or active joint damage and has had no progression of rheumatoid arthritis or joint damage as assessed at baseline or at a certain point of time during treatment. Those who are not in remission include, for example, those experiencing a worsening or progression of rheumatoid arthritis or joint damage. Remission, as defined by American College of Rheumatology (ACR)/European League Against Rheumatism (EULAR), is obtained when a patient satisfies all of the following at any time point: tender joint count ≤1, swollen joint count ≤1, C-Reactive Protein ≤1 mg/dl, and patient global assessment ≤1 (on a 0-10 scale), or when the patient has Simplified Disease Activity Index score ≤3.3 at any time point. Felson et al., *Arthritis & Rheumatism* 63(3): 573-586 (2011). Subjects experiencing a return of symptoms, including active rheumatoid arthritis or joint damage, are those who have "relapsed" or had a "recurrence."

An "effective response" in a patient, "effectiveness" of a treatment method, or a patient's "responsiveness" to a treatment method and similar wording refer to the clinical or therapeutic benefit imparted to a patient at risk for or suffering from rheumatoid arthritis by treatment method. Such benefit includes cellular or biological responses, a complete response, a partial response, or a stable disease (without progression or relapse).

The present invention provides treatment methods that provide therapeutic benefit in the treatment of rheumatoid arthritis. A therapeutic benefit is not necessarily a cure for rheumatoid arthritis, but rather encompasses a result which most typically includes alleviation of rheumatoid arthritis, remission of rheumatoid arthritis, elimination of rheumatoid arthritis, reduction of a symptom associated with rheumatoid arthritis, prevention or alleviation of a secondary disease, prevention of rheumatoid arthritis and/or increased patient survival. A therapeutic benefit or effective response includes a reduction in disease activity as reflected by various indices, such as CRP level, ESR, biomarker levels, or VECTRA DA Score.

The terms "not responsive" patient or "ineffective response" in a patient and similar wording refer to those patients who are resistant and/or refractory to the treatment method, and includes the situations in which a patient has progressed while receiving the therapeutic method, and in which a patient has progressed within 12 months after completing a regimen involving the treatment method to which he or she is no longer responsive. Thus, not responsive patients continue to have active disease following previous or current treatment.

The terms "algorithm" or "selection method" or "selection process" as used herein is a set of instructions for carrying out a procedure, optionally proceeding through a well-defined series of successive states, and eventually terminating in an end-state. The algorithm provides an objective selection of a treatment method for rheumatoid arthritis.

General Description of the Invention

The present invention provides methods for selecting treatment methods for rheumatoid arthritis based on an objective selection process (algorithm). The present invention also provides methods for treating rheumatoid arthritis with treatment methods selected based on the algorithm disclosed herein. The methods of the present invention provide a more effective means for treating patients with rheumatoid arthritis.

Measurement of Disease Activity

Measurement of rheumatoid arthritis disease activity is an important component of rheumatoid arthritis management. Curtis et al., *Arthritis Care & Res.* 64(12): 1794-1803 (2012). Several disease activity indices based on different clinical, laboratory, and physical measures have been used in the field. Id. The indices for disease activity are useful in monitoring disease activity in patients. Examples of physical disease activity indices include the Disease Activity Score (DAS), the modified DAS in 28 joints (DAS28), the Simplified Disease Activity Index (SDAI), the Clinical Disease Activity Index (CDAI), and the Routine Assessment of Patient Index Data 3 (RAPID3), patient reported outcomes (PRO). Id. Examples of laboratory disease activity indices include Erythrocyte Sedimentation Rate (ESR), C-Reactive Protein (CRP) level, Hemoglobin count, and Platelet count. Both ESR and CRP level are nonspecific markers of inflammation and can be increased in aging, anemia, infection, and injury.

The Disease Activity Score (DAS) is based on an external standard of rheumatoid arthritis disease activity, and combines information from swollen joints, tender joints, the acute phase response and general health into one continuous measure of rheumatoid inflammation. Fransen, *Clin. Exp. Rheumatol.* 23(Suppl. 39): S93-S99 (2005). DAS as originally developed is an index containing the Ritchie articular index (RAI, range 0-78), a 44 swollen joint count (range 0-44), the erythrocyte sedimentation rate, and an optional general health assessment on a visual analogue scale (range 0-100). Id.; Prevoo et al., *Arthritis & Rheumatism* 38(1): 44-48 (1995). A specially programmed DAS calculator, as well as a computer program which can be downloaded from the internet, are available to calculate DAS. DAS has a continuous scale ranging from 0-10, and usually shows a Gaussian distribution in rheumatoid arthritis populations. The level of disease activity can be interpreted as low (DAS$\leq$2.4), moderate (2.4<DAS$\leq$3.7), or high (DAS>3.7). A DAS<1.6 corresponds to a state of remission according to the American College of Rheumatology (previously, American Rheumatism Association (ARA)) criteria. Fransen, *Clin. Exp. Rheumatol.* 23(Suppl. 39): S93-S99 (2005).

Modified DAS (DAS28) includes measurement of 28 tender joint count (range 0-28), 28 swollen joint count (range 0-28), ESR, and an optional general health assessment on a visual analogue scale (range 0-100). The DAS28 has a continuous scale ranging from 0 to 9.4, and usually shows a Gaussian distribution in rheumatoid arthritis populations. DAS and DAS28 values cannot be directly compared, but a formula to transform DAS28 into DAS values is available. The level of disease activity can be interpreted as low (DAS28$\leq$3.2), moderate (3.2<DAS28$\leq$5.1), or high (DAS28>5.1). A DAS28<2.6 corresponds to a patient being in remission according to the ARA criteria, meaning that nearly all RA patients in remission have a DAS28<2.6, but not all patients with DAS28<2.6 are in remission. A change of 1.2 (i.e., 2 times the measurement error) of the DAS28 in an individual patient is considered a significant change. Id.

Another index for disease activity is Simplified Disease Activity Index (SDAI) that measures tender and swollen joint count, patient's global assessment, physician's global assessment, and C-Reactive Protein (CRP) level, Erythrocyte Sedimentation Rate (ESR), hemoglobin count, or platelet count.

Another index for disease activity is C-Reactive Protein (CRP) level and Erythrocyte Sedimentation Rate (ESR) with or without hemoglobin count or platelet count. In one aspect, ESR, CRP level, hemoglobin count, and platelet count are used to determine RA disease activity. The normal ranges for CRP level, ESR, hemoglobin count, and platelet count can be determined by a physician of ordinary skill in the treatment of RA working in his or her region, with his or her patient population or his or her clinical laboratories. For example, it is known that normal ranges for these markers may depend on the laboratory where the tests are performed. For example, for the tests conducted at locations of Laboratory Corporation of America (LabCorp), headquartered in 358 South Main Street, Burlington, N.C., the normal ranges for CRP level, ESR, hemoglobin count, and platelet count are 0.0-4.9 mg/L, 0-40 mm/hr, 11.1-15.9 g/dL, and 140-415×10 E3/µl, respectively. Generally, the greater the change in these indices from the normal range, the worse the disease prognosis.

In recent years, assays to measure biochemical and pathophysiological characteristics of rheumatoid arthritis based on the concentration of proteins in the blood, such as enzymes, cytokines, and bone metabolites, have been investigated as indices to understand RA biology and to monitor disease activity and disease progression. Li et al., *Curr. Med. Res. & Opin.* 29(1): 85-92 (2013).

A biomarker for rheumatoid arthritis disease activity can be any indicator of pathophysiological state of a patient, which can be affected in response to therapy. Examples of biomarkers include, but are not limited to, a DNA, RNA, protein, carbohydrate, or glycolipid-based molecular marker. The expression or presence of in a biological sample can be detected by standard methods (or methods disclosed herein). A biomarker can be predictive and/or prognostic of the responsiveness of an rheumatoid arthritis patient to a treatment method.

In some aspects, a biomarker is present in a patient sample, and is not present in a control or reference, or is present at an amount or concentration or level in the patient sample that differs from its amount in control or reference. In another aspect, the expression of a biomarker in the patient sample is determined to be higher than its level in the control. In another aspect, the expression of a biomarker in the patient sample is determined to be lower than its level in the control.

In some aspects, a biomarker is detected before, during, and/or after the administration of a therapeutic agent to a patient. In some aspects, a biomarker provides the basis for an assay that aids in determining the dosing and regimen, identifying patient subgroups or phenotypes that are responsive to the treatment method/therapeutic agent, or selecting a treatment method/therapeutic agent for treatment. In one aspect, a biomarker is used to monitor treatment in the patients. In another aspect, a biomarker is used to determine rheumatoid arthritis disease activity.

Biomarkers contemplated by the present invention are Vascular Cell Adhesion Molecule 1 (VCAM-1), Epidermal Growth Factor (EGF), Vascular Endothelial Growth Factor A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP).

The use of an individual biomarker to determine disease activity is limited as a single biomarker does not adequately reflect disease activity or response to rheumatoid arthritis therapy. Id. Multiplex assays that measure concentration of multiple biomarkers simultaneously are suggested to be better at capturing the complexity of rheumatoid arthritis disease and aid in the evaluation and categorization of patients with rheumatoid arthritis. Id. Recently efforts to develop multiplex biomarker assays for rheumatoid arthritis have been made. Id. One such assay that uses protein biomarkers to measure disease activity is commercially available VECTRA® DA test.

VECTRA® DA test is a multi-biomarker disease activity (MBDA) blood test sold by Crescendo Bioscience. The test provides a quantitative assessment of rheumatoid arthritis disease activity in patients by using twelve protein biomarkers—Vascular Cell Adhesion Molecule 1 (VCAM-1), Epidermal Growth Factor (EGF), Vascular Endothelial Growth Factor A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP). The twelve biomarkers in VECTRA® DA test are relevant to key aspects of the pathophysiology of RA. Li et al., *Curr. Med. Res. & Opin.* 29(1): 85-92 (2013). The test measures the concentrations of the biomarkers and provides the concentrations and percentile (RA percentile) value for each biomarker. The percentile value shows a comparison of the tested patient's biomarker levels relative to biomarker levels of a reference set of RA patients from a study (InFoRM study) and reflects the fraction of reference patients who have lower concentrations of the biomarker than the tested patient.

The VECTRA DA MBDA test uses Meso Scale Discovery (MSD, Gaithersburg, Md., USA) sandwich immunoassay electrochemiluminescent technology to measure biomarker levels. Eastman et al., *J. of Pharmaceutical and Biomedical Analysis* 70: 415-424 (2012). In the immunoassay, capture antibodies are spotted on carbon electrodes in a planar array and detection antibodies are labeled with an electrochemiluminescent ruthenium reporter. Id. Upon electrical stimulation, light is produced from reporter molecules bound to the electrode to determine biomarker concentration.

The test also provides a VECTRA DA MBDA Score (VECTRA DA Score that is obtained from an algorithm/formula that combines the measured concentrations of twelve serum protein biomarkers into a single score. Hirata et al., *Rheumatology Advance Access* (Feb. 7, 2013). The score represents the level of rheumatoid arthritis disease activity on a scale of 1 to 100. Id. The VECTRA® DA test significantly correlates with conventional clinical disease activity indices, such as the 28-joint count Disease Activity Score (DAS28) or 28-joint count Disease Activity Score using the C-Reactive (DAS28CRP). Id.

The VECTRA DA MBDA Score of ≤29 correlates with low rheumatoid arthritis disease activity, the Score of ≤44 but >29 correlates with moderate rheumatoid arthritis disease activity, and the Score of >44 correlates with high rheumatoid arthritis disease activity.

In some aspects, the effectiveness of treatment methods used in the methods herein is determined by using VECTRA® DA test and by using VECTRA DA Score (or multi-biomarker disease activity score) to determine rheumatoid arthritis disease activity.

Treatment Methods or Therapeutic Agents

Rheumatoid arthritis treatment aims to minimize disease activity, thereby preventing or controlling joint damage and reducing the risk of other serious co-morbidities, such as heart disease or stroke. Early intervention is vital in patients with confirmed rheumatoid arthritis to preserve joint function.

The treatment methods utilized in the methods disclosed herein are known in the art for treatment of rheumatoid arthritis. In some aspects, the treatment methods are disease-modifying antirheumatic drugs (DMARDs). In other aspects, the treatment methods are biologic agents that are known to treat rheumatoid arthritis. In other aspects, the treatment methods are pain relievers, non-steroidal anti-inflammatory drugs (NSAIDs), and glucocorticoids.

Disease-modifying antirheumatic drugs (DMARDs) are the mainstay of treatment for rheumatoid arthritis. DMARDs are a group of therapeutic agents that are commonly used in patients with rheumatoid arthritis. They decrease pain and inflammation, reduce or prevent joint damage, and preserve the structure and function of the joints. Common DMARDs are methotrexate (MTX), sulfasalazine (S), hydroxychloroquine (P), and leflunomide (ARA). Less frequently used DMARDs include gold salts, azathioprine (AZA), and cyclosporine.

Methotrexate (MTX) is the most commonly used DMARD. It is cost effective and comparatively well tolerated. Methotrexate may be combined with other DMARDs or with a biologic agent if methotrexate alone does not adequately control a patient's disease. Methotrexate can be administered via oral, intravenous, intramuscular, subcutaneous or intrathecal routes.

Sulfasalazine (S) may be used alone or combined with other DMARDs if a person does not respond adequately to one medication. It is administered via oral route.

Hydroxychloroquine or PLAQUENIL (P) can be used early in the course of rheumatoid arthritis and is often used in combination with other DMARDs. It is administered via oral route.

Leflunomide or ARAVA (ARA) inhibits production of inflammatory cells to reduce inflammation. It is often used alone but may be used in combination with methotrexate for people who have not responded adequately to methotrexate alone or together with a biologic agent. It is administered via oral route.

Azathioprine or Imuran (AZA) is an immunosuppressive antimetabolite that is an imidazolyl derivative of 6-mercaptopurine. It is administered via oral route.

While a number of rheumatoid arthritis patients respond to DMARDs, a large proportion of patients are still not responsive to DMARDs. Ma et al., *Biomedical Reports* 1: 177-184 (2013). Biologic agents is another class of therapeutic agents that are used to treat rheumatoid arthritis. They are also sometimes called biologic DMARDs and include a class of drugs called tumor necrosis factor inhibitors (TNF) (Etanercept, Adalimumab, Infliximab, Certolizumab pegol, and Golimumab) and a variety of other agents with different targets, including Anakinra, Abatacept (ATAB), Rituximab (RITUX), and tocilizumab (TOCL). Id. The targets of biologic agents are interactions between the immune effector cells (T lymphocytes, B lymphocytes and macrophages), which are responsible for inflammation and structural damage in affected joints, and the signaling molecules involved in their activation. These medications are often combined with methotrexate or other DMARDs to improve efficacy of treatment.

Tumor necrosis factor inhibitors (TNF) include Etanercept (ENBREL), Adalimumab (HUMIRA), Certolizumab pegol (CIMZIA), Golimumab (SIMPONI), Infliximab (REMICADE). Switching from one TNF inhibitor to another has become an established treatment approach for patients who failed or were intolerant of treatment with an initial TNF inhibitor. Rubbert-Roth et al., *Arthritis Research & Therapy* 11(1): 1-9 (2009). Despite having a similar mode of action, the rationale behind switching the TNF inhibitors is the variations in bioavailability, differences in the stability of the TNF-inhibitor complex or the potential occurrence of drug-neutralizing antibodies. Id.

Abatacept or ORENCIA (ATAB) is a soluble fusion protein that consists of the extracellular domain of human cytotoxic T-lymphocyte-associated antigen 4 (CTLA-4) linked to the modified Fc (hinge, CH2, and CH3 domains) portion of human immunoglobulin G1 (IgG1). The apparent molecular weight of abatacept is 92 kilodaltons. Abatacept is a second-line drug that is often used when DMARDs, such as methotrexate, and/or other biologic drugs have failed to control rheumatoid arthritis. Abatacept attaches to the surface of inflammatory cells and blocks communication between the cells, resulting in reduced inflammation. Abatacept is administered as an intravenous infusion.

Tocilizumab or ACTEMRA (TOCL) is a recombinant humanized anti-human interleukin 6 (IL-6) receptor monoclonal antibody of the immunoglobulin IgG1κ (gamma 1, kappa) subclass with a typical H2L2 polypeptide structure. It binds to interleukin-6 receptor and blocks interleukin-6 activity. As a result, the cells are unable to drive inflammation in rheumatoid arthritis. ACTEMRA has a molecular weight of approximately 148 kDa. Tocilizumab is administered as an intravenous infusion.

Rituximab or RITUXAN (or Rituximab) (RITUX) is a genetically engineered chimeric murine/human monoclonal IgG1 kappa antibody directed against the CD20 antigen. Rituximab has an approximate molecular weight of 145 kD. It targets a protein on B cells (CD20 antigen), which are a part of the immune system, and prevents autoimmune response in rheumatoid arthritis. Rituximab is administered as an intravenous infusion.

Tofacitinib or XELJANZ (TOFAC) is a drug and is a Janus Kinase 3 (JAK3) inhibitor and interferes with the JAK-STAT signaling pathway, which transmits extracellular information into the cell nucleus, influencing DNA transcription. It is administered via oral route.

DMARDS and biological agents can be used alone or in combination.

Other medicines, such as pain relievers, non-steroidal anti-inflammatory drugs (NSAIDS) (e.g., ibuprofen or naproxen), and glucocorticoids (e.g., prednisone) are given to provide faster relief of ongoing symptoms. DMARDs and biological agents are often used in combination with these medications to reduce the total amount of medication needed and to prevent damage to joints.

The treatment methods or therapeutic agents are administered to a patient or a subject in accordance with suitable methods, such as those known to medical practitioners, depending on many factors, including whether the dosing is acute or chronic. These routes include, for example, enteral (oral or rectal), parenteral, intravenous (bolus or continuous infusion over a period of time), subcutaneous, intramuscular, intra-arterial, intraperitoneal, transdermal, intradermal, intrapulmonary, transmucosal, intra-cerebrospinal, intra-articular, intra-synovial, intrathecal, intra-lesional, intracardiac, epidural or inhalation routes (e.g., intranasal or nasal). Parenteral administration includes intramuscular, intravenous, intra-arterial, intra-peritoneal, or subcutaneous administration.

Determination of Effectiveness of Treatment Methods

The goal of treatment is low disease activity or remission of rheumatoid arthritis. In one aspect, the goal of treatment is alleviation of rheumatoid arthritis, remission of rheumatoid arthritis, elimination of rheumatoid arthritis, reduction of a symptom associated with rheumatoid arthritis, prevention or alleviation of a secondary disease, prevention of rheumatoid arthritis, increased patient survival and/or reduction in disease activity as reflected by various indices, such as CRP level, ESR, biomarker levels, or VECTRA DA Score.

In another aspect, the goal of the treatment is the persistence of low rheumatoid arthritis disease activity for a minimum of six months, or a change in RA disease activity from high to medium activity or a change in rheumatoid arthritis disease activity from medium to low activity, without adverse effects or increase in patient's medications or treatments. In some aspects, the goal of treatment includes elimination of supplemental steroids, no morning stiffness, and a return to normal function of the affected joints for a period of no less than 6 months. Steroids have both anti-inflammatory and immunosuppressive effects and are often utilized at the onset of inflammatory arthritis. However, long term steroid use, even with moderate doses can be associated with undesirable side effects such as hypertension, diabetes, cataracts, and osteoporosis. So, most patients and clinicians are motivated to reduce steroids to the lowest possible dose or adjust treatment with other agents to allow the complete elimination of steroids.

The effectiveness of the treatment method is determined by measuring rheumatoid arthritis disease activity before and after treatment. Several approaches to monitor rheumatoid arthritis disease activity are known in the art. Some approaches to determine RA disease activity are exemplified below, but any approach known in the art may be used to monitor disease activity and determine effectiveness of a treatment method. It will be readily understood by the ordinarily skilled artisan that essentially any index known in the art to measure disease activity can be used herein.

In one aspect, a treatment method is determined to have an effective response in the patient when the rheumatoid arthritis disease activity after treatment is less than the rheumatoid arthritis disease activity before treatment. In another aspect, a treatment method is determined to have an effective response in a patient when the rheumatoid arthritis disease activity is reduced after treatment.

In one aspect, the disease activity before and after treatment is measured by measuring an index for disease activity before and after treatment. In one aspect, the disease activity before and after treatment is measured by measuring VECTRA DA Score, Erythrocyte Sedimentation Rate (ESR) and C-Reactive Protein (CRP) level before and after treatment. In another aspect, the disease activity before and after treatment is measured by measuring hemoglobin count and/or platelet count before and after treatment. In another aspect, the disease activity before and after treatment is measured by measuring VECTRA DA Score before and after treatment.

In one aspect, a reduction in rheumatoid arthritis disease activity after treatment is reflected by reduction in the level of ESR, CRP level, hemoglobin count, and/or platelet count after treatment. In another aspect, a reduction in rheumatoid arthritis disease activity after treatment is reflected by movement of ESR, CRP level, hemoglobin count and/or platelet count towards normalization. Some patients may have one or more of these indices move, while others may have all of them move, while yet others may have none of them move. A reduction in rheumatoid arthritis disease activity may thus show itself by other indicators than movement of indices alone, as is well known to those skilled in the art.

In one aspect, a reduction in rheumatoid arthritis disease activity after treatment is reflected by reduction or normalization of the elevated biomarkers measured in VECTRA® DA test.

In one aspect, a reduction in rheumatoid arthritis disease activity after treatment is reflected by reduction in VECTRA DA Score after treatment. In another aspect, a reduction in rheumatoid arthritis disease activity after treatment is reflected by movement of VECTRA DA Score after treatment from high disease activity to moderate or low disease activity, or from moderate disease activity to low disease activity. In another aspect, a reduction in rheumatoid arthritis disease activity after treatment is reflected by reduction in VECTRA DA Score after treatment to ≤29. In another aspect, a reduction in rheumatoid arthritis disease activity after treatment is reflected by reduction in VECTRA DA Score after treatment to ≤44 but >29. In another aspect, a reduction in rheumatoid arthritis disease activity after the treatment is reflected by at least 10%, at least 15%, at least 20%, at least 25%, at least 30%, at least 35%, at least 40%, at least 45%, at least 50%, at least 55%, at least 60%, at least 65%, at least 70%, or at least 75% reduction in VECTRA DA Score. In another aspect, a reduction in rheumatoid arthritis disease activity after treatment is reflected by at least 20% reduction in the VECTRA DA Score, or the movement of the VECTRA DA Score to a lower disease activity level after the treatment (i.e., from high to moderate, or high to low, or moderate to low).

In another aspect, a reduction in rheumatoid arthritis disease activity after treatment is reflected by a VECTRA DA Score of ≤29 in addition to normalization of the markers of inflammation—ESR, CRP level, hemoglobin count, and platelet count.

In another aspect, a reduction in disease activity after treatment is reflected by a reduction or elimination of the patient's use of steroids (e.g., prednisone).

In another aspect, a reduction in disease activity after treatment is reflected by a reduction of morning stiffness to less than 30 minutes; restoration of normal function of the affected joints; reduction in ESR, CRP level, hemoglobin count, and platelet count; and change in VECTRA DA Score by at least one activity level (e.g. from high activity to moderate activity or from moderate activity to low activity), with the ultimate goal of achieving VECTRA DA Score of less than 29.

In another aspect, a reduction in rheumatoid arthritis disease activity after treatment is reflected by a response in at least 4 of 6 measures: 20% improvement in morning stiffness, Erythrocyte Sedimentation Rate (ESR), joint tenderness score, and joint swelling score and improvement by at least 2 grades on a 5-grade scale (or from grade 2 to grade 1) for patient and physician global assessments of current disease severity. Felson et al., *Arthritis & Rheumatism* 38(6): 727-735 (1995).

In another aspect, a reduction in rheumatoid arthritis disease activity after treatment is defined as ≥20% improvement in tender and swollen joint counts and ≥20% improvement in at least 3 of the following 5 American College of Rheumatology core set measures: pain, patient global assessment, physician global assessment, self-assessed physical disability, and acute phase reactant. Id.

In another aspect, a reduction in rheumatoid arthritis disease activity after treatment is reflected by a reduction of at least 1.2 (i.e., 2 times the measurement error) in DAS28 of a patient. Fransen, *Clin. Exp. Rheumatol.* 23(Suppl. 39): S93-S99 (2005). In another aspect, a reduction in rheumatoid arthritis disease activity after treatment is reflected by a reduction in DAS28 to ≤3.2.

In one aspect, a treatment method is determined to have an effective response in a patient when VECTRA DA Score after treatment is lower than VECTRA DA Score before treatment. In another aspect, a treatment method is determined to have an effective response in a patient when VECTRA DA Score is decreased to a lower disease activity level after treatment. In one aspect, a treatment method is determined to have an effective response in a patient when VECTRA DA Score is decreased from a high disease activity level before treatment to a moderate or low disease activity level after treatment. In another aspect, a treatment method is determined to have an effective response in a patient when VECTRA DA Score is decreased from a moderate disease activity level before treatment to a low disease activity level after treatment. In another aspect, a treatment method is determined to have an effective response in a patient when VECTRA DA Score is decreased to ≤29 after treatment. In another aspect, a treatment method is determined to have an effective response in a patient when VECTRA DA Score is decreased to ≤44 but >29 after treatment. In another aspect, a treatment method is determined to have an effective response in a patient when the VECTRA DA Score is reduced by at least 10%, at least 15%, at least 20%, at least 25%, at least 30%, at least 35%, at least 40%, at least 45%, at least 50%, at least 55%, at least 60%, at least 65%, at least 70%, or at least 75% after the treatment. In another aspect, a treatment method is determined to have an effective response in a patient when the VECTRA DA Score is reduced by at least 20%, or when the VECTRA DA Score is decreased to a lower disease activity level (i.e., from high to moderate, or high to low, or moderate to low) after the treatment.

In one aspect, a treatment method is determined to have an effective response in a patient when VECTRA DA Score, ESR and CRP level after treatment is lower than VECTRA DA Score, ESR and CRP level before treatment.

In one aspect, a treatment method is determined to have an effective response in a patient when ESR and/or CRP level after treatment is lower than ESR and/or CRP level before treatment, unless the reduction is due to another cause, e.g. infection or surgery. In another aspect, a treatment method is determined to have effective response in a patient when ESR and/or CRP level after treatment move towards normal levels, unless the reduction is due to another cause, e.g. infection or surgery. The ESR and CRP level are measured by methods known in the art.

In one aspect, a treatment method is determined to have an effective response in a patient when ESR, CRP level, hemoglobin count, and/or platelet count after treatment is lower than ESR, CRP level, hemoglobin count, and/or platelet count before treatment, unless the reduction is due to another cause, e.g. infection or surgery. In another aspect, a treatment method is determined to have an effective response in a patient by movement of ESR, CRP level, hemoglobin count and/or platelet count towards normalization.

In another aspect, a treatment method is determined to have an effective response in a patient when VECTRA DA Score is ≤29 in addition to normalization of the markers of inflammation—ESR, CRP level, hemoglobin count, and platelet count.

In another aspect, a treatment method is determined to have an effective response in a patient when the patient's use of steroids (e.g., prednisone) after treatment is a reduced or eliminated.

In another aspect, a treatment method is determined to have an effective response in a patient when morning stiffness is reduced to less than 30 minutes; normal function of the affected joints is restored; ESR, CRP level, hemoglobin count, and platelet count are reduced; and VECTRA DA Score is reduced by at least one activity level (e.g. from high activity to moderate activity or from moderate activity to low activity), with the ultimate goal of achieving VECTRA DA Score of less than 29.

In another aspect, a treatment method is determined to have an effective response in a patient when at least 4 of 6 selected measures are obtained: 20% improvement in morning stiffness, erythrocyte sedimentation rate (ESR), joint tenderness score, and joint swelling score and improvement by at least 2 grades on a 5-grade scale (or from grade 2 to grade 1) for patient and physician global assessments of current disease severity. Felson et al., *Arthritis & Rheumatism* 38(6): 727-735 (1995).

In another aspect, a treatment method is determined to have an effective response in a patient when there is ≥20% improvement in tender and swollen joint counts and ≥20% improvement in at least 3 of the following 5 American College of Rheumatology core set measures: pain, patient global assessment, physician global assessment, self-assessed physical disability, and acute phase reactant. Id.

In another aspect, a treatment method is determined to have an effective response in a patient when DAS28 of the patient is reduced by at least 1.2 (i.e., 2 times the measurement error). Fransen, Clin. Exp. Rheumatol. 23(Suppl. 39): S93-S99 (2005). In another aspect, a treatment method is determined to have an effective response in a patient when DAS28 is reduced to ≤3.2.

Remission, as defined by American College of Rheumatology (ACR)/European League Against Rheumatism (EULAR), is obtained when a patient satisfies all of the following at any time point: tender joint count ≤1, swollen joint count ≤1, C-Reactive Protein ≤1 mg/dl, and patient global assessment ≤1 (on a 0-10 scale), or when the patient has Simplified Disease Activity Index score ≤3.3 at any time point. Felson et al., *Arthritis & Rheumatism* 63(3): 573-586 (2011). In one aspect, a treatment method is determined to have an effective response in the patient when remission is achieved. In another aspect, a treatment method is determined to have an effective response in the patient when at any time point: tender joint count ≤1, swollen joint count ≤1, C-Reactive Protein ≤1 mg/dl, and patient global assessment ≤1 (on a 0-10 scale), or when the patient has Simplified Disease Activity Index score ≤3.3 at any time point.

Algorithm to Select a Treatment Method

The present invention provides a selection method (algorithm) that utilizes levels of biomarkers that are known to be affected or altered (increased or decreased) in rheumatoid arthritis to select and guide treatment of patients with rheumatoid arthritis. The present invention provides an algorithm that determines levels of biomarkers that are known to be affected or altered (increased or decreased) in rheumatoid arthritis, identifies the biomarkers with altered (increased or decreased) levels in a patient sample compared to a control sample, and selects a treatment method that affects the biomarkers with the altered levels.

In one aspect, the biomarker utilized herein is any biomarker that is known to be affected or altered (increased or decreased) in rheumatoid arthritis. In one aspect, a biomarker is a protein that is affected or altered (increased or decreased) in rheumatoid arthritis and correlates with rheumatoid arthritis disease activity.

Biomarkers contemplated by the present invention are Vascular Cell Adhesion Molecule 1 (VCAM-1), Epidermal Growth Factor (EGF), Vascular Endothelial Growth Factor A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP).

It will be readily understood by the ordinarily skilled artisan that essentially any technical means established in the art for detecting biomarkers, either at nucleic acid or protein level, can be adapted to detect known biomarkers and applied in the methods of the invention.

In one aspect, at least two biomarkers are utilized in the algorithm to select a treatment method and to guide treatment. In another aspect, at least three, at least four, at least five, at least six, at least seven, at least eight, at least nine, at least ten, at least eleven, or at least twelve biomarkers are utilized in the algorithm to select a treatment method and to guide treatment. In another aspect, the maximum number of biomarkers are utilized in the algorithm to select a treatment method and to guide treatment. In another aspect, the maximum number of the highest elevated biomarkers are utilized in the algorithm to select a treatment method and to guide treatment.

In one aspect, the biomarker utilized in the algorithm has at least 40%, at least 45%, at least 50%, at least 55%, at least 60%, at least 65%, at least 70%, at least 75%, at least 80%, at least 85%, at least 90%, or at least 95% altered serum level than control serum level. In another aspect, the biomarker utilized in the algorithm has at least 40%, at least 45%, at least 50%, at least 55%, at least 60%, at least 65%, at least 70%, at least 75%, at least 80%, at least 85%, at least 90%, or at least 95% elevated serum level than control serum level. In a preferred aspect, the biomarker utilized in the algorithm has at least 40% elevated serum level than control serum level. In another aspect, the biomarker utilized in the algorithm has at least 40%, at least 45%, at least 50%, at least 55%, at least 60%, at least 65%, at least 70%, at least 75%, at least 80%, at least 85%, at least 90%, or at least 95% reduced serum level than control serum level.

In a preferred aspect, at least two biomarkers each one with at least 40% elevated serum level than control serum level are utilized in the algorithm.

In one aspect, the invention provides a method for selecting a treatment method for rheumatoid arthritis comprising: (i) determining serum levels in the patient of at least two biomarkers selected from the group consisting of Vascular Cell Adhesion Molecule-1 (VCAM-1), Vascular Endothelial Growth Factor-A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP); (ii) identifying at least two biomarkers each one with at least 40% elevated serum level over control serum level; (iii) selecting at least one treatment method that is known to affect the at least two biomarkers identified in step (ii).

In another aspect, the invention provides a method for selecting a treatment method for rheumatoid arthritis comprising: (i) determining serum levels in the patient of at least two biomarkers selected from the group consisting of Vascular Cell Adhesion Molecule-1 (VCAM-1), Vascular Endothelial Growth Factor-A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP); (ii) identifying at least two biomarkers each one with at least 40% elevated serum level over control serum level; (iii) selecting at least one treatment method that is known to affect the at least two biomarkers identified in step (ii), wherein the treatment method is selected from the group consisting of PLAQUENIL (or Hydroxychloroquine), Sulfasalazine, Methotrexate, ARAVA (or Leflunomide), Tumor Necrosis Factor-α inhibitors, Atabacept (or ORENCIA), Tocilizumab (or ACTEMRA), RITUXAN (or Rituximab), and Tofacitinib (or XELJANZ).

In some aspects, the determining in step (i) comprises determining serum levels of at least three biomarker. In other aspects, the determining in step (i) comprises determining serum levels of at least four biomarkers. In some aspects, the determining in step (i) comprises determining serum levels of at least five biomarkers. In some aspects, the determining in step (i) comprises determining serum levels of at least six biomarkers. In some aspects, the determining in step (i) comprises determining serum levels of at least seven biomarkers. In some aspects, the determining in step (i) comprises determining serum levels of at least eight biomarkers. In some aspects, the determining in step (i) comprises determining serum levels of at least nine biomarkers. In some aspects, the determining in step (i) comprises determining serum levels of at least ten biomarkers. In some aspects, the determining in step (i) comprises determining serum levels of at least eleven biomarkers. In some aspects, the determining in step (i) comprises determining serum levels of at least twelve biomarkers.

In some aspects, the identifying in step (ii) comprises identifying a biomarker with at least 40%, at least 45%, at least 50%, at least 55%, at least 60%, at least 65%, at least 70%, at least 75%, at least 80%, at least 85%, at least 90%, or at least 95% elevated serum level over control serum level.

In some aspects, the identifying in step (ii) comprises identifying at least two biomarkers each one with at least 40%, at least 45%, at least 50%, at least 55%, at least 60%, at least 65%, at least 70%, at least 75%, at least 80%, at least 85%, at least 90%, or at least 95% elevated serum level over control serum level.

In some aspects, the identifying in step (ii) comprises identifying at least three biomarkers each one with at least 40%, at least 45%, at least 50%, at least 55%, at least 60%, at least 65%, at least 70%, at least 75%, at least 80%, at least 85%, at least 90%, or at least 95% elevated serum level over control serum level.

In some aspects, the identifying in step (ii) comprises identifying at least four biomarkers each one with at least 40%, at least 45%, at least 50%, at least 55%, at least 60%, at least 65%, at least 70%, at least 75%, at least 80%, at least 85%, at least 90%, or at least 95% elevated serum level over control serum level.

In some aspects, the identifying in step (ii) comprises identifying at least five biomarkers each one with at least 40%, at least 45%, at least 50%, at least 55%, at least 60%, at least 65%, at least 70%, at least 75%, at least 80%, at least 85%, at least 90%, or at least 95% elevated serum level over control serum level.

In some aspects, the identifying in step (ii) comprises identifying at least six biomarkers each one with at least 40%, at least 45%, at least 50%, at least 55%, at least 60%, at least 65%, at least 70%, at least 75%, at least 80%, at least 85%, at least 90%, or at least 95% elevated serum level over control serum level.

In some aspects, the identifying in step (ii) comprises identifying at least seven biomarkers each one with at least 40%, at least 45%, at least 50%, at least 55%, at least 60%, at least 65%, at least 70%, at least 75%, at least 80%, at least 85%, at least 90%, or at least 95% elevated serum level over control serum level.

In some aspects, the identifying in step (ii) comprises identifying at least eight biomarkers each one with at least 40%, at least 45%, at least 50%, at least 55%, at least 60%, at least 65%, at least 70%, at least 75%, at least 80%, at least 85%, at least 90%, or at least 95% elevated serum level over control serum level.

In some aspects, the identifying in step (ii) comprises identifying at least nine biomarkers each one with at least 40%, at least 45%, at least 50%, at least 55%, at least 60%, at least 65%, at least 70%, at least 75%, at least 80%, at least 85%, at least 90%, or at least 95% elevated serum level over control serum level.

In some aspects, the identifying in step (ii) comprises identifying at least ten biomarkers each one with at least 40%, at least 45%, at least 50%, at least 55%, at least 60%, at least 65%, at least 70%, at least 75%, at least 80%, at least 85%, at least 90%, or at least 95% elevated serum level over control serum level.

In some aspects, the identifying in step (ii) comprises identifying at least eleven biomarkers each one with at least 40%, at least 45%, at least 50%, at least 55%, at least 60%, at least 65%, at least 70%, at least 75%, at least 80%, at least 85%, at least 90%, or at least 95% elevated serum level over control serum level.

In some aspects, the identifying in step (ii) comprises identifying at least twelve biomarkers each one with at least 40%, at least 45%, at least 50%, at least 55%, at least 60%, at least 65%, at least 70%, at least 75%, at least 80%, at least 85%, at least 90%, or at least 95% elevated serum level over control serum level.

In one aspect, the algorithm utilizes VECTRA® DA test to determine serum levels in step (i) and to identify at least two biomarkers each one with at least 40% elevated serum level in step (ii).

In some aspects, the selecting in step (iii) further comprises selecting a treatment method that is known to affect the maximum number of biomarkers identified in step (ii). In other aspects, the selecting in step (iii) further comprises selecting a treatment method that is known to affect the maximum number of the highest elevated biomarkers. In some aspects, the selecting in step (iii) further comprises avoiding a treatment method that is contraindicated (e.g., patient's body weight, lipid or cholesterol levels, positive or negative rheumatoid factor, duration of disease) or causes an allergic response in the patient. In some aspects, the selecting in step (iii) further comprises selecting a treatment method that is administered via a route selected from the group consisting of intravenous, intraarterial, enteral (oral or rectal), intramuscular, subcutaneous, transdermal, intradermal, nasal, intramuscular, intraperitoneal, intracardiac, epidural, intrathecal, and transmucosal. In other aspects, the selected route is preferred by the patient. In some aspects, the selecting in step (iii) comprises selecting a treatment method that fits with the patient's social (e.g., expense) and work circumstances. In other aspects, the selecting in step (iii) comprises selecting a treatment method based on the patient's preference for older or newer treatment methods. In some aspects, the selecting in step (iii) comprises selecting a treatment method that is required under the patient's medical plan. In some aspects, the selecting in step (iii) comprises selecting a treatment method that has less known side effects than other methods.

In some aspects, the selecting in step (iii) comprises using any combination of the selection options in any order.

In some aspects, the selecting comprises selecting a treatment method that is known to affect at least three biomarkers identified in step (ii). In other aspects, the selecting comprises selecting a treatment method that is known to affect at least four biomarkers identified in step (ii). In other aspects, the selecting comprises selecting a treatment method that is known to affect at least five biomarkers identified in step (ii). In other aspects, the selecting comprises selecting a treatment method that is known to affect at least six biomarkers identified in step (ii). In other aspects, the selecting comprises selecting a treatment method that is known to affect at least seven biomarkers identified in step (ii). In other aspects, the selecting comprises selecting a treatment method that is known to affect at least eight biomarkers identified in step (ii). In other aspects, the selecting comprises selecting a treatment method that is known to affect at least nine biomarkers identified in step (ii). In other aspects, the selecting comprises selecting a treatment method that is known to affect at least ten biomarkers identified in step (ii). In other aspects, the selecting comprises selecting a treatment method that is known to affect at least eleven biomarkers identified in step (ii). In other aspects, the selecting comprises selecting a treatment method that is known to affect at least twelve biomarkers identified in step (ii).

In some aspects, the selecting comprises selecting a treatment method that is known to affect at least three biomarkers each one with at least 40% elevated serum level. In other aspects, the selecting comprises selecting a treatment method that is known to affect at least four biomarkers each one with at least 40% elevated serum level. In other aspects, the selecting comprises selecting a treatment method that is known to affect at least five biomarkers each one with at least 40% elevated serum level. In other aspects, the selecting comprises selecting a treatment method that is known to affect at least six biomarkers each one with at least 40% elevated serum level. In other aspects, the selecting comprises selecting a treatment method that is known to affect at least seven biomarkers each one with at least 40% elevated serum level. In other aspects, the selecting comprises selecting a treatment method that is known to affect at least eight biomarkers each one with at least 40% elevated serum level. In other aspects, the selecting comprises selecting a treatment method that is known to affect at least nine biomarkers each one with at least 40% elevated serum level. In other aspects, the selecting comprises selecting a treatment method that is known to affect at least ten biomarkers each one with at least 40% elevated serum level. In other aspects, the selecting comprises selecting a treatment method that is known to affect at least eleven biomarkers each one with at least 40% elevated serum level. In other aspects, the selecting comprises selecting a treatment method that is known to affect at least twelve biomarkers each one with at least 40% elevated serum level.

In some aspects, the selecting comprises selecting a treatment method that is known to affect at least two biomarkers each one with at least 50% elevated serum level. In other aspects, the selecting comprises selecting a treatment method that is known to affect at least three biomarkers each one with at least 50% elevated serum level. In other aspects, the selecting comprises selecting a treatment method that is known to affect at least four biomarkers each one with at least 50% elevated serum level. In other aspects, the selecting comprises selecting a treatment method that is known to affect at least five biomarkers each one with at least 50% elevated serum level. In other aspects, the selecting comprises selecting a treatment method that is known to affect at least six biomarkers each one with at least 50% elevated serum level. In other aspects, the selecting comprises selecting a treatment method that is known to affect at least seven biomarkers each one with at least 50% elevated serum level. In other aspects, the selecting comprises selecting a treatment method that is known to affect at least eight biomarkers each one with at least 50% elevated serum level. In other aspects, the selecting comprises selecting a treatment method that is known to affect at least nine biomarkers each one with at least 50% elevated serum level. In other aspects, the selecting comprises selecting a treatment method that is known to affect at least ten biomarkers each one with at least 50% elevated serum level. In other aspects, the selecting comprises selecting a treatment method that is known to affect at least eleven biomarkers each one with at least 50% elevated serum level. In other aspects, the selecting comprises selecting a treatment method that is known to affect at least twelve biomarkers each one with at least 50% elevated serum level.

In some aspects, the selecting comprises selecting a treatment method that is known to affect at least two biomarkers each one with at least 60% elevated serum level. In other aspects, the selecting comprises selecting a treatment method that is known to affect at least three biomarkers each one with at least 60% elevated serum level. In other aspects, the selecting comprises selecting a treatment method that is known to affect at least four biomarkers each one with at least 60% elevated serum level. In other aspects, the selecting comprises selecting a treatment method that is known to affect at least five biomarkers each one with at least 60% elevated serum level. In other aspects, the selecting comprises selecting a treatment method that is known to affect at least six biomarkers each one with at least 60% elevated serum level. In other aspects, the selecting comprises selecting a treatment method that is known to affect at least seven biomarkers each one with at least 60% elevated serum level. In other aspects, the selecting comprises selecting a treatment method that is known to affect at least eight biomarkers each one with at least 60% elevated serum level. In other aspects, the selecting comprises selecting a treatment method that is known to affect at least nine biomarkers each one with at least 60% elevated serum level. In other aspects, the selecting comprises selecting a treatment method that is known to affect at least ten biomarkers each one with at least 60% elevated serum level. In other aspects, the selecting comprises selecting a treatment method that is known to affect at least eleven biomarkers each one with at least 60% elevated serum level. In other aspects, the selecting comprises selecting a treatment method that is known to affect at least twelve biomarkers each one with at least 60% elevated serum level.

In some aspects, the selecting comprises selecting a treatment method that is known to affect at least two biomarkers each one with at least 70% elevated serum level. In other aspects, the selecting comprises selecting a treatment method that is known to affect at least three biomarkers each one with at least 70% elevated serum level. In other aspects, the selecting comprises selecting a treatment method that is known to affect at least four biomarkers each one with at least 70% elevated serum level. In other aspects, the selecting comprises selecting a treatment method that is known to affect at least five biomarkers each one with at least 70% elevated serum level. In other aspects, the selecting comprises selecting a treatment method that is known to affect at least six biomarkers each one with at least 70% elevated serum level. In other aspects, the selecting comprises selecting a treatment method that is known to affect at least seven biomarkers each one with at least 70% elevated serum level. In other aspects, the selecting comprises selecting a treatment method that is known to affect at least eight biomarkers each one with at least 70% elevated serum level. In other aspects, the selecting comprises selecting a treatment method that is known to affect at least nine biomarkers each one with at least 70% elevated serum level. In other aspects, the selecting comprises selecting a treatment method that is known to affect at least ten biomarkers each one with at least 70% elevated serum level. In other aspects, the selecting comprises selecting a treatment method that is known to affect at least eleven biomarkers each one with at least 70% elevated serum level. In other aspects, the selecting comprises selecting a treatment method that is known to affect at least twelve biomarkers each one with at least 70% elevated serum level.

In some aspects, the selecting comprises selecting a treatment method that is known to affect at least two biomarkers each one with at least 80% elevated serum level. In other aspects, the selecting comprises selecting a treatment method that is known to affect at least three biomarkers each one with at least 80% elevated serum level. In other aspects, the selecting comprises selecting a treatment method that is known to affect at least four biomarkers each one with at least 80% elevated serum level. In other aspects, the selecting comprises selecting a treatment method that is known to affect at least five biomarkers each one with at least 80% elevated serum level. In other aspects, the selecting comprises selecting a treatment method that is known to affect at least six biomarkers each one with at least 80% elevated serum level. In other aspects, the selecting comprises selecting a treatment method that is known to affect at least seven biomarkers each one with at least 80% elevated serum level. In other aspects, the selecting comprises selecting a treatment method that is known to affect at least eight biomarkers each one with at least 80% elevated serum level. In other aspects, the selecting comprises selecting a treatment method that is known to affect at least nine biomarkers each one with at least 80% elevated serum level. In other aspects, the selecting comprises selecting a treatment method that is known to affect at least ten biomarkers each one with at least 80% elevated serum level. In other aspects, the selecting comprises selecting a treatment method that is known to affect at least eleven biomarkers each one with at least 80% elevated serum level. In other aspects, the selecting comprises selecting a treatment method that is known to affect at least twelve biomarkers each one with at least 80% elevated serum level.

In some aspects, the selecting comprises selecting a treatment method that is known to affect at least two biomarkers each one with at least 90% elevated serum level. In other aspects, the selecting comprises selecting a treatment method that is known to affect at least three biomarkers each one with at least 90% elevated serum level. In other aspects, the selecting comprises selecting a treatment method that is known to affect at least four biomarkers each one with at least 90% elevated serum level. In other aspects, the selecting comprises selecting a treatment method that is known to affect at least five biomarkers each one with at least 90% elevated serum level. In other aspects, the selecting comprises selecting a treatment method that is known to affect at least six biomarkers each one with at least 90% elevated serum level. In other aspects, the selecting comprises selecting a treatment method that is known to affect at least seven biomarkers each one with at least 90% elevated serum level. In other aspects, the selecting comprises selecting a treatment method that is known to affect at least eight biomarkers each one with at least 90% elevated serum level. In other aspects, the selecting comprises selecting a treatment method that is known to affect at least nine biomarkers each one with at least 90% elevated serum level. In other aspects, the selecting comprises selecting a treatment method that is known to affect at least ten biomarkers each one with at least 90% elevated serum level. In other aspects, the selecting comprises selecting a treatment method that is known to affect at least eleven biomarkers each one with at least 90% elevated serum level. In other aspects, the selecting comprises selecting a treatment method that is known to affect at least twelve biomarkers each one with at least 90% elevated serum level.

In one aspect, the treatment method selected based on the algorithm is one treatment method. In another aspect, the treatment method selected based on the algorithm is a combination of one or more treatment methods. In one aspect, the treatment methods in the combination of treatment methods are known to affect the same biomarkers. In another aspect, the treatment methods in the combination of treatment methods are known to affect different biomarkers. In some aspects, the combination of treatment methods is known to affect the maximum number of biomarkers identified in step (ii).

In one aspect, the treatment method selected based on the algorithm was not previously administered to the patient. In another aspect, the treatment method selected based on the algorithm was previously administered to the patient, but is now administered in combination with a different treatment method or in a different form or concentration or via a different route.

Methods for Treatment of Rheumatoid Arthritis

The methods of the present invention provide a more effective means for treating patients with rheumatoid arthritis. The current philosophy of treatment of rheumatoid arthritis is "treat to target" (i.e., treatment to rapid reduction of the signs and symptoms of inflammation to a low disease activity state). With the rising costs of healthcare and with more than 50 new products in research and development for rheumatoid arthritis, a more accurate and objective method for selection and modification of treatment will be invaluable to the physicians and patients. The present invention provides a treatment selection method (algorithm) that is advantages over the conventional guidelines because it addresses the unique biochemical and pathophysiological characteristics of each rheumatoid arthritis patient.

The present invention also provides methods for treating rheumatoid arthritis by using a treatment method selected based on the algorithm disclosed herein. The present invention provides methods for treating a patient with rheumatoid arthritis, wherein the method comprises determining levels of at least two biomarkers that are known to be affected or altered (increased or decreased) in rheumatoid arthritis in a patient sample, identifying biomarkers that are altered (increased or decreased), selecting a treatment method based on at least two biomarkers, and administering the selected treatment method to the patient with rheumatoid arthritis.

The present invention also provides methods for treating a patient with rheumatoid arthritis, wherein the method comprises determining levels of at least two biomarkers that are known to be affected or altered in rheumatoid arthritis in a patient sample, selecting a first treatment method based on at least two biomarkers in the sample, administering the first treatment method to the patient with rheumatoid arthritis, and determining effectiveness or ineffectiveness of the first treatment method administered to the patient.

The present invention also provides methods for treating a patient with rheumatoid arthritis, wherein the method comprises determining levels of at least two biomarkers that are known to be affected or altered in rheumatoid arthritis in a patient sample, selecting a first treatment method based on at least two biomarkers in the sample, administering the first treatment method to the patient with rheumatoid arthritis, determining effectiveness or ineffectiveness of the first treatment method administered to the patient, selecting a second treatment method based on at least two biomarkers in the sample, and administering the second treatment method selected in step.

In one aspect, the method for treating a patient with rheumatoid arthritis includes selecting a third, a fourth, a fifth, a sixth, a seventh, an eighth, a ninth, or a tenth treatment method based on the algorithm and administering the treatment method to the patient.

In one aspect, the treatment method administered to the patient is one treatment method. In another aspect, the treatment method administered to the patient is a combination of one or more treatment methods. In one aspect, the treatment methods in the combination of treatment methods are known to affect the same biomarkers. In another aspect, the treatment methods in the combination of treatment methods are known to affect different biomarkers.

In one aspect, the treatment method administered to the patient was not earlier administered to the patient. In another aspect, the treatment method administered to the patient was administered earlier to the patient, but is subsequently administered in combination with a different treatment method or in a different form or concentration or via a different route.

In one aspect, the subsequently administered treatment method is different than the earlier administered treatment method. In another embodiment, the subsequently administered treatment method does not comprise the earlier administered treatment method. In another embodiment, the subsequently administered treatment method comprises the earlier administered treatment method, but in a different combination than the earlier administered treatment method or in a different form or concentration or via a different route.

The effectiveness of the treatment method is determined by measuring rheumatoid arthritis disease activity before and after treatment. It will be readily understood by the ordinarily skilled artisan that essentially any index known in the art to measure disease activity can be used herein. In one aspect, the disease activity before and after treatment is measured by measuring VECTRA DA Score, Erythrocyte Sedimentation Rate (ESR), and C-Reactive Protein (CRP) level before and after treatment. In another aspect, the disease activity before and after treatment is measured by measuring VECTRA DA Score, Erythrocyte Sedimentation Rate (ESR), or C-Reactive Protein (CRP) level before and after treatment. In another aspect, the disease activity before and after treatment is measured by measuring VECTRA DA Score before and after treatment.

A treatment method is determined to have an effective response in the patient when the rheumatoid arthritis disease activity after treatment is less than the rheumatoid arthritis disease activity before treatment. In one aspect, a treatment method is determined to have an effective response in a patient when VECTRA DA Score after treatment is lower than VECTRA DA Score before treatment. In another aspect, a treatment method is determined to have an effective response in a patient when VECTRA DA Score is decreased to a lower disease activity level after treatment. In one aspect, a treatment method is determined to have an effective response in a patient when VECTRA DA Score is decreased from a high disease activity level before treatment to a moderate or low disease activity level after treatment. In another aspect, a treatment method is determined to have an effective response in a patient when VECTRA DA Score is decreased from a moderate disease activity level before treatment to a low disease activity level after treatment. In another aspect, a treatment method is determined to have an effective response in a patient when VECTRA DA Score is decreased to $\leq 29$ after treatment. In another aspect, a treatment method is determined to have an effective response in a patient when VECTRA DA Score is decreased to $\leq 44$ but $>29$ after treatment. In another aspect, a treatment method is determined to have an effective response in a patient when the VECTRA DA Score is reduced by at least 10%, at least 15%, at least 20%, at least 25%, at least 30%, at least 35%, at least 40%, at least 45%, at least 50%, at least 55%, at least 60%, at least 65%, at least 70%, or at least 75% after the treatment. In another aspect, a treatment method is determined to have an effective response in a patient when the VECTRA DA Score is reduced by at least 20%, or when the VECTRA DA Score is decreased to a lower disease activity level (i.e., from high to moderate, or high to low, or moderate to low) after the treatment.

In one aspect, a treatment method is determined to have an effective response in a patient when VECTRA DA Score, ESR and CRP level after treatment is lower than VECTRA DA Score, ESR and CRP level before treatment.

In one aspect, a treatment method is determined to have an effective response in a patient when ESR and/or CRP level after treatment is lower than ESR and/or CRP level before treatment, unless the reduction is due to another cause, e.g. infection or surgery. In another aspect, a treatment method is determined to have effective response in a patient when ESR and/or CRP level after treatment move towards normal levels, unless the reduction is due to another cause, e.g. infection or surgery. The ESR and CRP level are measured by methods known in the art.

In one aspect, a treatment method is determined to have an effective response in a patient when ESR, CRP level, hemoglobin count, and/or platelet count after treatment is lower than ESR, CRP level, hemoglobin count, and/or platelet count before treatment, unless the reduction is due to another cause, e.g. infection or surgery. In another aspect, a treatment method is determined to have an effective response in a patient by movement of ESR, CRP level, hemoglobin count and/or platelet count towards normalization.

In another aspect, a treatment method is determined to have an effective response in a patient when VECTRA DA Score is $\leq 29$ in addition to normalization of the markers of inflammation—ESR, CRP level, hemoglobin count, and platelet count.

In another aspect, a treatment method is determined to have an effective response in a patient when morning stiffness is reduced to less than 30 minutes; normal function of the affected joints is restored; ESR, CRP level, hemoglobin count, and platelet count are reduced; and VECTRA DA Score is reduced by at least one activity level (e.g. from high activity to moderate activity or from moderate activity to low activity), with the ultimate goal of achieving VECTRA DA Score of less than 29.

In another aspect, a treatment method is determined to have an effective response in a patient when VECTRA DA Score is $\leq 29$ in addition to normalization of the markers of inflammation—ESR, CRP level, hemoglobin count, and platelet count.

In another aspect, a treatment method is determined to have an effective response in a patient when the patient's use of steroids (e.g., prednisone) after treatment is a reduced or eliminated.

In another aspect, a treatment method is determined to have an effective response in a patient when morning stiffness is reduced to less than 30 minutes; normal function of the affected joints is restored; ESR, CRP level, hemoglobin count, and platelet count are reduced; and VECTRA DA Score is reduced by at least one activity level (e.g. from high activity to moderate activity or from moderate activity to low activity), with the ultimate goal being the achievement of a VECTRA DA Score of less than 29.

In another aspect, a treatment method is determined to have an effective response in a patient when at least 4 of 6 selected measures are obtained: 20% improvement in morning stiffness, erythrocyte sedimentation rate (ESR), joint tenderness score, and joint swelling score and improvement by at least 2 grades on a 5-grade scale (or from grade 2 to grade 1) for patient and physician global assessments of current disease severity. Felson et al., *Arthritis & Rheumatism* 38(6): 727-735 (1995).

In another aspect, a treatment method is determined to have an effective response in a patient when there is $\geq 20\%$ improvement in tender and swollen joint counts and $\geq 20\%$ improvement in at least 3 of the following 5 American College of Rheumatology core set measures: pain, patient global assessment, physician global assessment, self-assessed physical disability, and acute phase reactant. Id.

In another aspect, a treatment method is determined to have an effective response in a patient when DAS28 of the patient is reduced by at least 1.2 (i.e., 2 times the measurement error). Fransen, *Clin. Exp. Rheumatol.* 23(Suppl. 39): S93-S99 (2005). In another aspect, a treatment method is determined to have an effective response in the patient when DAS28 is reduced to ≤3.2.

Remission, as defined by American College of Rheumatology (ACR)/European League Against Rheumatism (EULAR), is obtained when a patient satisfies all of the following at any time point: tender joint count ≤1, swollen joint count ≤1, C-Reactive Protein ≤1 mg/dl, and patient global assessment ≤1 (on a 0-10 scale), or when the patient has Simplified Disease Activity Index score ≤3.3 at any time point. Felson et al., *Arthritis & Rheumatism* 63(3): 573-586 (2011). In one aspect, a treatment method is determined to have an effective response in a patient when remission is achieved. In another aspect, In another aspect, a treatment method is determined to have an effective response in a patient when at any time point: tender joint count ≤1, swollen joint count ≤1, C-Reactive Protein ≤1 mg/dl, and patient global assessment ≤1 (on a 0-10 scale), or when the patient has Simplified Disease Activity Index score ≤3.3 at any time point.

The invention for determining levels of biomarkers and selecting treatment methods is provided above.

It will be readily understood by the ordinarily skilled artisan that essentially any treatment method known in the art for treatment of rheumatoid arthritis can utilized in the methods disclosed herein. In some aspects, the treatment methods are disease-modifying antirheumatic drugs (DMARDs). In other aspects, the treatment methods are biologic agents that are known to treat rheumatoid arthritis. In other aspects, the treatment methods are pain relievers, non-steroidal anti-inflammatory drugs (NSAIDs), and glucocorticoids.

Rheumatoid arthritis treatment methods contemplated by the present invention include, but are not limited to, Hydroxychloroquine or PLAQUENIL (P), Leflunomide or ARAVA (ARA), Azathioprine or Imuran (AZA), Tumor necrosis factor inhibitors (TNF) (such as ENBREL, HUMIRA, CIMZIA, SIMPONI, REMICADE), Abatacept or ORENCIA (ATAB), Tocilizumab or ACTEMRA (TOCL), Rituximab or RITUXAN (or Rituximab) (RITUX), Tofacitinib or XELJANZ (TOFAC), pain relievers, non-steroidal anti-inflammatory drugs (NSAIDs) (such as, ibuprofen or naproxen), and glucocorticoids (such as, prednisone).

In one aspect, the invention provides a method for treating a patient with rheumatoid arthritis, wherein the method comprises: (i) determining serum levels in the patient of at least two biomarkers selected from the group consisting of Vascular Cell Adhesion Molecule-1 (VCAM-1), Vascular Endothelial Growth Factor-A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP); (ii) identifying at least two biomarkers each one with at least 40% elevated serum level over control serum level; (iii) selecting at least one treatment method that is known to affect the at least two biomarkers identified in step (ii); and (iv) administering the treatment method selected in step (iii) to the patient.

In one aspect, the invention provides a method for treating a patient with rheumatoid arthritis, wherein the method comprises: (i) determining serum levels in the patient of at least two biomarkers selected from the group consisting of Vascular Cell Adhesion Molecule-1 (VCAM-1), Vascular Endothelial Growth Factor-A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP); (ii) identifying at least two biomarkers each one with at least 40% elevated serum level over control serum level; (iii) selecting at least one treatment method that is known to affect the at least two biomarkers identified in step (ii), wherein the treatment method is selected from the group consisting of PLAQUENIL (or Hydroxychloroquine), Sulfasalazine, Methotrexate, ARAVA (or Leflunomide), Tumor Necrosis Factor-α inhibitors, Atabacept (or ORENCIA), Tocilizumab (or ACTEMRA), RITUXAN (or Rituximab), and Tofacitinib (or XELJANZ); and (iv) administering the treatment method selected in step (iii) to the patient.

In another aspect, the invention provides a method for treating a patient with rheumatoid arthritis, wherein the method comprises: (i) determining serum levels in the patient of at least two biomarkers selected from the group consisting of Vascular Cell Adhesion Molecule-1 (VCAM-1), Vascular Endothelial Growth Factor-A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP); (ii) identifying at least two biomarkers each one with at least 40% elevated serum level over control serum level; (iii) selecting a first treatment method that is known to affect the at least two biomarkers identified in step (ii), wherein the treatment method is selected from the group consisting of PLAQUENIL (or Hydroxychloroquine), Sulfasalazine, Methotrexate, ARAVA (or Leflunomide), Tumor Necrosis Factor-α inhibitors, Atabacept (or ORENCIA), Tocilizumab (or ACTEMRA), RITUXAN (or Rituximab), and Tofacitinib (or XELJANZ); (iv) administering the first treatment method selected in step (iii) to the patient; and (v) determining effectiveness or ineffectiveness of the first treatment method administered in step (iv) to the patient.

In another aspect, the invention provides a method for treating a patient with rheumatoid arthritis, wherein the method comprises: (i) determining serum levels in the patient of at least two biomarkers selected from the group consisting of Vascular Cell Adhesion Molecule-1 (VCAM-1), Vascular Endothelial Growth Factor-A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP); (ii) identifying at least two biomarkers each one with at least 40% elevated serum level over control serum level; (iii) selecting a first treatment method that is known to affect the at least two biomarkers identified in step (ii), wherein the treatment method is selected from the group consisting of PLAQUENIL (or Hydroxychloroquine), Sulfasalazine, Methotrexate, ARAVA (or Leflunomide), Tumor Necrosis Factor-α inhibitors, Atabacept (or ORENCIA), Tocilizumab (or ACTEMRA), RITUXAN (or Rituximab), and Tofacitinib (or XELJANZ); (iv) administering the first treatment method selected in step (iii) to the patient; and (v) determining effectiveness or ineffectiveness of the first treatment method administered in step (iv) to the patient; (vi) selecting a second treatment method, and (vii) administering the second treatment method selected in step (vi) to the patient.

In some aspects, the determining in (v) comprises: (viii) determining VECTRA DA Score, C-Reactive Protein (CRP) level, and Erythrocyte Sedimentation Rate (ESR) in the patient before and after the first treatment method; and (ix) comparing the VECTRA DA Score, CRP level, and ESR in the patient before and after the first treatment method. In other aspects, the determining in (v) comprises: (i) determining VECTRA DA Score, C-Reactive Protein (CRP) level, or Erythrocyte Sedimentation Rate (ESR) in the patient before and after the first treatment method; and (ii) comparing the VECTRA DA Score, CRP level, and ESR in the patient before and after the first treatment method. In other aspects, the determining in (v) comprises: (i) determining VECTRA DA Score in the patient before and after the first treatment method; and (ii) comparing the VECTRA DA Score in the patient before and after the first treatment method. In some aspects, the determining in (v) comprises: (i) determining one or more selected from the group consisting of VECTRA DA Score, CRP level, and Sedimentation Rate in the patient before and after the first treatment method; and (ii) comparing the one or more selected from the group consisting of VECTRA DA Score, CRP level, and Erythrocyte Sedimentation Rate in the patient before and after the first treatment method.

In another aspect, the selecting for the second treatment method in (vi) comprises (x) identifying at least two biomarkers selected from the group consisting of Vascular Cell Adhesion Molecule-1 (VCAM-1), Vascular Endothelial Growth Factor-A (VEGF-A), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP), each one with at least 40% elevated serum level over control serum level; and (xi) selecting a second treatment method that is known to affect the at least two biomarkers identified in step (x), wherein the treatment method is selected from the group consisting of PLAQUENIL (or Hydroxychloroquine), Sulfasalazine, Methotrexate, ARAVA (or Leflunomide), Tumor Necrosis Factor-α inhibitors, Atabacept (or ORENCIA), Tocilizumab (or ACTEMRA), RITUXAN (or Rituximab), and Tofacitinib (or XELJANZ).

In some aspects administering comprising administering therapeutically effective amount of a treatment method or a therapeutic agent to the patient.

The algorithm and methods of treatment disclosed herein may be used by a healthcare provider. In one aspect, the healthcare provider is a physician, hospital, or formulary. The use of the disclosed algorithms is not be limited to healthcare providers, but may also find value in a more scientifically drive treatment protocol.

EXAMPLES

Example 1

Development of Reference Grid

A PubMed search was performed for articles or abstracts published in 1990-2012 on all twelve biomarkers reported in the VECTRA® DA test report, i.e., Vascular Cell Adhesion Molecule 1 (VCAM-1), Vascular Endothelial Growth Factor A (VEGF-A), Epidermal Growth Factor (EGF), Interleukin-6 (IL-6), Tumor Necrosis Factor Receptor Type 1 (TNFR1), Matrix Metalloproteinase-1 (MMP-1), Matrix Metalloproteinase-3 (MMP-3), YKL-40, Leptin, Resistin, Serum Amyloid A (SAA), and C-Reactive Protein (CRP). Scientific articles that discussed in vitro effects of the biomarkers or clinical trials that measured response of the twelve biomarkers to a treatment method were identified. Over 180 articles were identified and selected. The abstracts presented at the American College of Rheumatology annual meetings in 2006-2013 were also selected on a similar basis. The selected articles and abstracts were reviewed and a grid, shown in Table 1, was constructed to indicate which biomarkers are known to be positively affected by a Treatment method and which biomarkers are not known to be positively affected by a treatment method.

The grid in Table 1 lists 9 most commonly used treatment methods for rheumatoid arthritis (DMARDs and biological agents) along the horizontal axis (x-axis) and eleven out of twelve biomarkers reported in VECTRA DA test report along the vertical axis (y-axis). The grid shows the biomarkers that are known to be positively affected by a treatment method (i.e., biomarkers that are known to have a favorable response to a treatment method) as "Y" in the cell that corresponds to that treatment method and biomarker, biomarkers that are not known to be positively affected by a treatment method (i.e., biomarkers that are known to have an unfavorable response to a treatment method) as "N" in the cell that corresponds to that treatment method and biomarker, and biomarkers that are known to be positively affected by a ORENCIA, the brand name of Atabacept, (i.e., biomarkers that are known to have a favorable response to ORENCIA) as "O" in the cell that corresponds to ATAB and biomarker.

Thus, when a cell in the grid lists "Y," it indicates that the biomarker corresponding to that cell is known to be positively affected by the treatment method corresponding to the cell. When a cell in the grid lists "N," it indicates that the biomarker corresponding to that cell is not known to be positively affected by the treatment method corresponding to the cell. When a cell in the grid lists "O," it indicates that the biomarker corresponding to that cell (Leptin) is known to be positively affected by ORENCIA, the brand name of Atabacept. And, when a cell in the grid is left empty, it indicates that there is no statistically significant information available to reach a conclusion on the effect of the treatment method corresponding to that cell on the biomarker corresponding to the cell.

For example, the cell corresponding to TNF (along the x-axis) and VEGF-A (along the y-axis) lists "Y," indicating that VEGF-A is known to be positively affected by TNF treatment. The cell corresponding to P (along the x-axis) and TNFR1 (along the y-axis) lists "N," indicating that TNFR1 is not known to be positively affected by P treatment.

TABLE 1

Grid Showing Biomarkers Affected by Treatment Methods

|  | P | S | MTX | ARA | TNF | ATAB | TOCL | RITUX | TOFAC |
|---|---|---|---|---|---|---|---|---|---|
| VCAM-1 | N |  | N | Y | Y | Y | N | N |  |
| VEGF-A | N | Y | Y |  | Y | N | Y |  |  |
| IL-6 | Y | Y | Y | Y | N | Y | Y | Y | Y |
| TNFR1 | N | Y | N | Y | Y |  | N |  |  |
| MMP-1 | N |  | N | Y | Y | N | Y | N | Y |
| MMP-3 | N | Y | Y | Y | Y | Y | Y | N | Y |
| YKL-40 | N | N | N |  | Y | N | Y | N |  |
| Leptin* |  | N | N |  | N | O | N | N |  |

TABLE 1-continued

Grid Showing Biomarkers Affected by Treatment Methods

|  | P | S | MTX | ARA | TNF | ATAB | TOCL | RITUX | TOFAC |
|---|---|---|-----|-----|-----|------|------|-------|-------|
| Resistin | N | N | N | N | Y | N | N | N | |
| SAA | Y | Y | Y | Y | Y | N | Y | N | |
| CRP | Y | Y | Y |  | Y | Y | Y | Y | |

*In accordance with the warning provided with VECTRA ® DA test, Leptin can be used as a biomarker only in patients with 15% or less body fat.

Example 2

Treatment of Rheumatoid Arthritis by Treatment Methods Selected Using Algorithm

Patients

Figure 6:
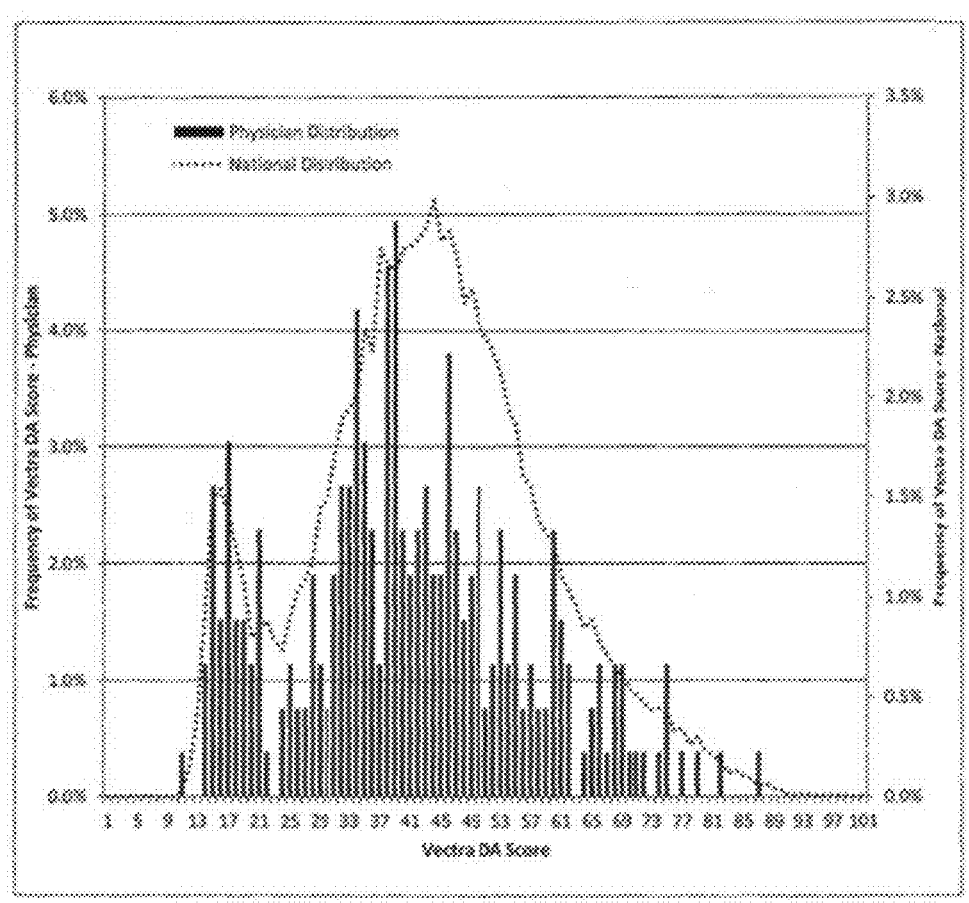
FIG. 6 shows a comparison of the distribution of pre-treatment VECTRA DA Scores in the inventor's patient population of 263 total patients with 75% patients who were started on the treatment methods that were selected based on the preliminary VECTRA DA analysis (shown as physician distribution by the bar graph) and the distribution of pre-treatment VECTRA DA Scores in a random patient population available nationwide (shown as national distribution by the dotted curve).

Rheumatoid arthritis patients were treated by treatment methods that were selected using the algorithm disclosed herein. VECTRA® DA test was conducted for each patient to determine serum levels of all the biomarkers and VECTRA DA Score in each patient before treatment. The collection of patients closely resembles the random patient population available nationwide as shown by a comparison of the distribution of VECTRA DA Scores in FIG. 6. FIG. 6 shows a comparison of the distribution of pre-treatment VECTRA DA Scores in the inventor's patient population of 263 total patients with 75% patients who were started on the treatment methods that were selected based on the preliminary VECTRA DA analysis (shown as physician distribution by the bar graph) and the distribution of pre-treatment VECTRA DA Scores in a random patient population available nationwide (shown as national distribution by the dotted curve).

Majority of patients had longstanding RA, and had failed the treatment methods delineated in the American College of Rheumatology treatment guidelines. The pre-treatment CRP level and ESR was also determined for each patient by the methods known in the art.

Selection and Administration of Treatment Methods

A group of biomarkers having each biomarker with at least 40% elevated serum level than the serum level in a control set of RA patients from the InFoRM study (that was used to establish range of biomarker level in patients) was identified. Treatment methods were identified that are known to affect at least two biomarkers from among the selected biomarkers (using the Grid). Among the identified treatment methods, the methods were selected based on the patient's history—the methods that were contraindicated, were unsuccessful in treating the patient previously, or were known to cause an allergic response in the patient were avoided, and the treatment methods that were known to affect the maximum number of biomarkers or were known to affect the maximum number of the highest elevated biomarkers and were administered via patient's preferred route were selected and were administered to the patient. PLAQUENIL (hydroxychloroquine) and sulfasalazine were not used to treat the patients due to their clinical histories—PLAQUENIL and sulfasalazine are mild drugs that work on mild cases of arthritis early in the disease process. Most patients had either longstanding disease or disease with poor prognosis, making PLAQUENIL or sulfasalazine undesirable treatment choices. Tocilizumab (or ACTEMRA) and RITUXAN (or Rituximab) were considered as the last options because both are administered intravenouosly, have highest cost, and have most serious side effects.

The patients were treated with the selected treatment methods for at least five months and the post-treatment biomarker levels and VECTRA DA Score were determined by VECTRA® DA test along with CRP level and ESR. The change is VECTRA DA Score, CRP level and ESR was determined to determine the change in disease activity and effectiveness of the selected treatment method.

The treatment method was determined to be effective when the post-treatment disease activity was lower than the pre-treatment disease activity in the patient: when VECTRA DA Score was lower than the pre-treatment VECTRA DA Score and/or when post-treatment CRP level and/or post-treatment ESR was lower than the corresponding pre-treatment values.

If the first selected treatment method was determined to be ineffective in the patient, then a second treatment method was selected based on the similar protocol as discussed before.

Table 2 shows the outcome of the treatment of ten such patients using treatment methods that were selected based on the algorithm. These patients are among the most difficult patients to manage in a typical rheumatology practice.

TABLE 2

Patient Data

| Patient No. | Selected VECTRA ® DA Biomarkers Having At Least 40% Elevated Level | Treatment Selected Based on Selected VECTRA ® DA Biomarkers | Duration of Treatment | Disease Activity Measurement (Change in Disease Activity Indices After Treatment) | Treatment Outcome |
|---|---|---|---|---|---|
| 4. 58 yr, F | | CIMZIA (TNF), Methotrexate (MTX), and Leflunomide (ARA), November 2012 | November 2012-June 2013 | VECTRA DA Score - Decreased by 24 ESR - Trended Downward CRP level - Normalized, but then increased due to upper | Effective, based on VECTRA DA Score and ESR Patient no longer reporting pain or |

TABLE 2-continued

Patient Data

| Patient No. | Selected VECTRA ® DA Biomarkers Having At Least 40% Elevated Level | Treatment Selected Based on Selected VECTRA ® DA Biomarkers | Duration of Treatment | Disease Activity Measurement (Change in Disease Activity Indices After Treatment) | Treatment Outcome |
|---|---|---|---|---|---|
| 5. 75 yr, M | | Methotrexate (MTX), March 2012 (MTX was not selected based on the algorithm) | | respiratory tract infection | swelling in the joints Not effective |
| | TNF-R1 Resistin | Methotrexate (MTX) and CIMZIA (TNF), October 2012 (CIMZIA (TNF) was added, October 2012) | October 2012-June 2013 | VECTRA DA Score - Not Available ESR - Trended Downwards CRP level - Trended Downwards | Effective, based on Sedimentation Rate and CRP Level |
| 6. 66 yr, F | | ACTEMRA (TOCL), August 2012 (after failing treatment with CIMZIA, Azathioprine, and Leflunomide, which were not selected based on the algorithm.) | August 2012-June 2013 | VECTRA DA Score, February 2013 - Decreased by 24 Sedimentation Rate - Returned to Normal CRP Level - Returned to Normal | The patient has prolonged pain and morning stiffness in joints. Not reflected by the change in any of the three disease markers Not effective |
| 8. 53 yr, F | | Methotrexate (MTX) (MTX was not selected based on the algorithm) | | | |
| | VCAM-1 VEGF-A IL-6 MMP-3 Leptin CRP | ORENCIA (ATAB), December 2012 | December 2012-June 2013 | VECTRA DA Score, March 2013 - Decreased by 20 (low disease activity state) ESR - Remained Normal CRP level - Remained Normal | Effective, based on VECTRA DA score Reflected by change in all three disease markers |
| 9. 61 yr, M | | ACTEMRA (TOCL), May 2012 (TOCL was not selected based on the algorithm.) | | | Not effective |
| | IL-6 MMP-3 CRP | Methotrexate (MTX), added October 2012 | October 2012-June 2013 | VECTRA DA Score - Not Available ESR - Returned to Normal CRP level - Returned to Normal Patient was able to wean off steroids | Effective, based on ESR and CRP level |
| 10. 64 yr, M | | Methotrexate (MTX), November 2011 | | | Not effective |
| | | ORENCIA (ATAB), August 2012-December 2012 | | | Not effective |

TABLE 2-continued

Patient Data

| Patient No. | Selected VECTRA® DA Biomarkers Having At Least 40% Elevated Level | Treatment Selected Based on Selected VECTRA® DA Biomarkers | Duration of Treatment | Disease Activity Measurement (Change in Disease Activity Indices After Treatment) | Treatment Outcome |
|---|---|---|---|---|---|
|  | VEGF-A IL-6 SAA CRP | (Treatment methods above were not selected based on the algorithm.) HUMIRA (TNF), December 2012 | December 2012-June 2013 | VECTRA DA Score, May 2013 - Decreased by 22 ESR - Remained Normal CRP level - Returned to Normal | Effective, based on VECTRA DA Score Reflected by change in Sedimentation Rate and CRP level Pain and stiffness improved but the patient remained fatigued |
| 12. 32 yr, F |  | Methotrexate (MTX), ORENCIA (ATAB), and Prednisone, July 2011 |  |  | Not effective |
|  |  | Methotrexate (MTX), ORENCIA (ATAB), Prednisone, and Mycophenylate mofetil, February 2012 Prednisone, and Mycophenylate mofetil, June 2012 (ORENCIA and Methotrexate stopped) Leflunomide (ARA) restarted, September 2012 (Treatment methods above were not selected based on the algorithm.) |  |  | Not effective |
|  | IL-6 MMP-3 VEGF CRP | Methotrexate (MTX) and ACTEMRA (TOCL) added, September 2012-October 2012 (ACTEMRA discontinued due to allergic reaction.) |  |  |  |
|  |  | ACTEMRA replace with HUMIRA (TNF), October 2012 (HUMIRA selected based on patient history - the | October 2012-June 2013 | VECTRA DA Score, December 2012 - Decreased by 44 ESR - Returned to Normal After HUMIRA CRP level - Returned to | Effective, based on the change in the VECTRA DA score Reflected by the change in ESR and |

TABLE 2-continued

Patient Data

| Patient No. | Selected VECTRA ® DA Biomarkers Having At Least 40% Elevated Level | Treatment Selected Based on Selected VECTRA ® DA Biomarkers | Duration of Treatment | Disease Activity Measurement (Change in Disease Activity Indices After Treatment) | Treatment Outcome |
|---|---|---|---|---|---|
| | | patient had been on HUMIRA before.) So, ultimately the patient is given Leflunomide, Methotrexate and HUMIRA | | Normal After HUMIRA | CRP level Final regimen of methotrexate, leflunomide, and HUMIRA has allowed patient to taper off prednisone, reduce use of narcotic analgesics. |
| 13. 85 yr, F | | Methotrexate (MTX) and ACTEMRA (TOCL), started before August 2011 (MTX and TOCL were not selected based on the algorithm.) | | | Not effective |
| | VCAM-1 IL-6 MMP-3 TNF-R1 | ACTEMRA stopped, and CIMZIA added, January 2013 Final treatment - Methotrexate and CIMZIA | January 2013-June 2013 | VECTRA DA Score, March 2013 - Reduced by 21 ESR - Remained Normal After CIMZIA CRP level - Remained Normal After CIMZIA | Effective, based on the change in the VECTRA DA Score Reflected by the change in Sedimentation Rate and CRP level |
| 14. 70 yr, F | | Leflunomide (ARA) and Azathioprine (AZA), September 2008 (ARA and AZA were not selected based on the algorithm.) | | | Not effective |
| | IL-6 SAA MMP-3 VCAM-1 | Leflunomide (ARA) and Methotrexate (MTX), October 2012 | | | Not effective |
| | IL-6 MMP-3 SAA VCAM-1 TNF-R1 CRP | Prednisone and CIMZIA (TNF), December 2012 (Prednisone was not selected based on the algorithm.) | December 2012-June 2013 | VECTRA DA Score, March 2013 - decreased by 24 Sedimentation Rate - Returned to Normal After CIMZIA CRP level - Remained Normal After CIMZIA | Effective, based on the change in VECTRA DA Score Reflected by the change in Sedimentation Rate and CRP level |
| 16. 75 yr, F | | Azathioprine (AZA), March 2012 CIMZIA (TNF), May 2012 (AZA and TNF were not selected based on the algorithm.) | | | Not effective |

TABLE 2-continued

Patient Data

| Patient No. | Selected VECTRA ® DA Biomarkers Having At Least 40% Elevated Level | Treatment Selected Based on Selected VECTRA ® DA Biomarkers | Duration of Treatment | Disease Activity Measurement (Change in Disease Activity Indices After Treatment) | Treatment Outcome |
|---|---|---|---|---|---|
| | IL-6 Leptin MMP-3 Resistin CRP SAA VEGF-A MMP-1 | Methotrexate (MTX), September 2011, Azathioprine (AZA), March 2012 and CIMZIA (TNF), May 2012 (MTX and AZA were not selected based on the algorithm.) | May 2012-June 2013 | VECTRA DA Score, March 2013 - Decreased by 26 Sedimentation Rate - Remained Normal After CIMZIA CRP Level - Remained Normal After CIMZIA | Effective, based on the change in VECTRA DA score Reflected by the change in Sedimentation Rate and CRP Level Triple therapy of Methtrexate, Azathioprine, and CIMZIA needed to be able to reduce Prednisone to 3 mg/day |

Figure 7:
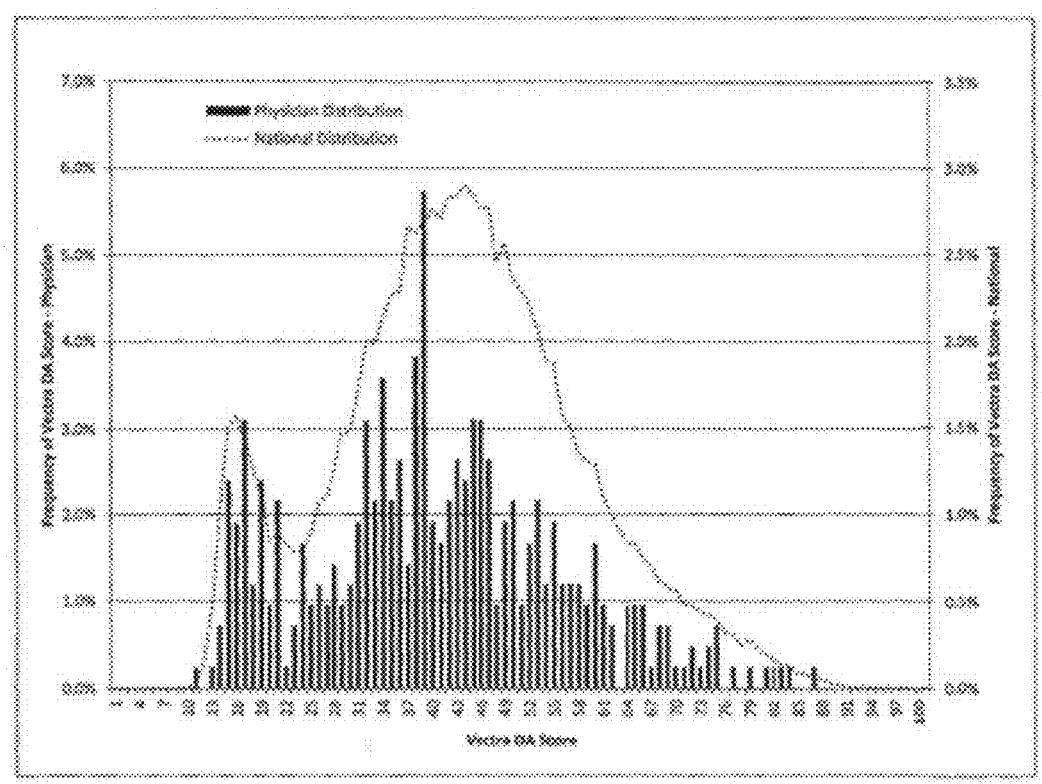
FIG. 7 shows a comparison of the distribution of post-treatment VECTRA DA Scores in the inventor's patient population of 419 total patients with 75% patients who were treated by the treatment methods that were selected based on the algorithm as described in Example 2 (shown as physician distribution by the bar graph) and the distribution of post-treatment VECTRA DA Scores a random patient population available nationwide (shown by the dotted curve) for the same duration of treatment.

A comparison of the distribution of the post-treatment VECTRA DA Scores in the inventor's patient population of 419 total patients with 75% patients who were treated with treatment methods selected based on the algorithm for 5-6 months (shown as physician distribution by the bar graph) with the distribution of post-treatment VECTRA DA Score of a control population (a random patient population available nationwide that was treated for 5-6 months with treatment methods that were not selected based on the algorithm) is shown in FIG. 7.

The comparison shows that the patients treated with methods that were selected based on the algorithm have more patients in low disease activity state and less patients in high disease activity states than the control population after treatment. Additionally, the patients treated with treatment methods selected based on the algorithm have lower disease activity than the control population.

Given the heterogeneous group of patients, it is difficult to demonstrate a single consistent feature. But a composite picture shows an improvement in both laboratory and clinical manifestations of the disease. A comparison of the distribution of VECTRA DA Scores in a collection of patients after treatment based on the algorithm and distribution of VECTRA DA Scores in a random patient population that were treated nationwide showed that there are more patients that have VECTRA DA Score corresponding to low disease activity and the patient population has lower disease activity than the nationwide population after treatment (in an objective blind comparison) (FIG. 7). Thus, the treatment methods selected based on the algorithm are more effective than treatment methods selected nationwide without the algorithm.

Example 3

Treatment of Rheumatoid Arthritis by Treatment Methods Selected Using Algorithm

Patients

Sixteen rheumatoid arthritis patients were selected for treatment by treatment methods that were selected using the algorithm disclosed herein. Some patients were the same as the patients discussed under Example 2. Example 3, however, tracks patients' responses to treatment for a longer duration and uses VECTRA DA Score to determine effectiveness of the treatment.

VECTRA® DA test was conducted for each patient to determine serum levels of the all the biomarkers and VECTRA DA Score in each patient before treatment. The collection of patients closely resembles the random patient population available nationwide as shown by a comparison of the distribution of VECTRA DA Scores in FIG. 6, as noted under Example 2.

Majority of patients had longstanding RA, and had failed the treatment methods delineated in the American College of Rheumatology treatment guidelines. Two patients have juvenile idiopathic arthritis, and had failed established recommended treatments.

Selection and Administration of Treatment Methods

A group of biomarkers having each biomarker with at least 40% elevated serum level than the serum level in a control set of RA patients from the InFoRM study (that was used to establish range of biomarker level in patients) was identified. Treatment methods were identified that are known to affect at least two biomarkers from among the selected biomarkers (using the Grid). Among the identified treatment methods, the methods were selected based on the patient's history—the methods that were contraindicated, were unsuccessful in treating the patient previously, or were known to cause an allergic response in the patient were avoided, and the treatment methods that were known to affect the maximum number of biomarkers or were known to affect the maximum number of the highest elevated biomarkers and were administered via patient's preferred route were selected and were administered to the patient. PLAQUENIL (hydroxychloroquine) and sulfasalazine were not used to treat the patients due to their clinical histories—PLAQUENIL and sulfasalazine are mild drugs that work on mild cases of arthritis early in the disease process. Most patients had either longstanding disease or disease with poor prognosis, making PLAQUENIL or sulfasalazine undesirable treatment choices. Tocilizumab (or ACTEMRA) and RITUXAN (or Rituximab) were considered as the last options because both are administered intravenously, have highest cost, and have most serious side effects.

The patients were treated with the selected treatment methods and the post-treatment biomarker levels and VECTRA DA Score were determined by VECTRA® DA test. The change is VECTRA DA Score was determined to determine the change in disease activity and effectiveness of the selected treatment method.

The treatment method (one method or a combination of methods) was determined to be effective when the post-treatment disease activity was lower than the pre-treatment disease activity in the patient: when VECTRA DA Score was lower than the pre-treatment VECTRA DA Score. Specifically, the treatment method was determined to be effective when the post-treatment disease activity was at least 20% lower than the pre-treatment disease activity, or when the VECTRA DA Score is decreased to a lower disease activity level after the treatment (i.e., from high to moderate, or high to low, or moderate to low).

If the first selected treatment method (one method or a combination of methods) was determined to be ineffective in the patient, then a second treatment method (one method or a combination of methods) was selected based on the similar protocol as discussed before. A treatment method administered to a patient may be a combination of one or more treatment methods.

Table 3 shows the outcome of the treatment of 16 patients using treatment methods that were selected based on the algorithm. These patients are among the most difficult patients to manage in a typical rheumatology practice. For Table 3, biomarkers with at least 40% elevated serum level were numbered in reverse chronological order, with the biomarker with the highest % elevation numbered as "1." Biomarkers with same % elevation were given the same number and the biomarker with the % elevation lower than that elevation was given two number below that number.

TABLE 3

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| 1. | August 2012 Score: 68 (high) | | Based on preliminary VECTRA DA analysis, Methotrexate (MTX) and TNF were selected Patient declined ACTEMRA (TOCL) TNF and ACTEMRA not allowed by the FDA | Patient did not have additional joint damage in the right wrist as compared to April 2010 | |
|  | (1) SAA | 96% | | | |
|  | (2) CRP | 95% | | | |
|  | (3) IL-6 | 92% | | | |
|  | (4) YKL-40 | 71% | | | |
|  | (5) MMP-3 | 65% | | | |
|  | (6) Resistin | 58% | | | |
|  | October 2013 Score: 10 (low) | | Methotrexate (MTX) - 1, 4 TNF - 1, 2, 3, 4 Methotrexate dose reduced to 7.5 mg/week | | |
|  | (1) MMP-3 | 62% | | | |
|  | (2) Resistin | 53% | | | |
|  | (3) YKL-40 | 49% | | | |
|  | (4) CRP | 47% | | | |
|  | (5) Leptin | 43% | | | |
|  | April 2014 Score: 30 (moderate) | | Methotrexate (MTX) - 1, 3, 4 TNF - 1, 2, 3, 4 Methotrexate dose increased from 7.5 mg/week to 10 mg/week | VECTRA DA Score - 30; decreased by 38 since August 2012 | Effective, based on VECTRA DA Score |
|  | (1) MMP-3 | 61% | | | |
|  | (2) Resistin | 51% | | | |
|  | (3) CRP | 48% | | | |
|  | (4) SAA | 46% | | | |
| 2. | August 2012 Score: 65 (high) | | Based on preliminary VECTRA DA analysis, Methotrexate (MTX), Leflunomide (ARA), ACTEMRA were selected Treatment with 3 different TNFs | | |
|  | (1) IL-6 | >99% | | | |
|  | (2) MMP-3 | 96% | | | |
|  | (3) CRP | 96% | | | |
|  | (4) VEGF-A | 93% | | | |
|  | (5) SAA | 73% | | | |
|  | (6) VCAM-1 | 71% | | | |
|  | (7) MMP-1 | 71% | | | |
|  | (8) Resistin | 68% | | | |
|  | (9) Leptin | 54% | | | |

TABLE 3-continued

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| | (10) YKL-40 | 51% | was previously unsuccessful Treatment ORENCIA (ATAB) was previously unsuccessful | | |
| | (11) TNF-R1 | 42% | | | |
| | November 2012 Score: 73 (high) | | Methotrexate (MTX) - 1, 2, 3, 5, 8 | | |
| | (1) IL-6 | >99% | | | |
| | (2) MMP-3 | 97% | XELJANZ (TOFAC) - 1, 2 | | |
| | (3) CRP | 87% | TNF (CIMZIA) - 2, 3, 4, 5, 6, 8, 9 | | |
| | (4) Resistin | 85% | | | |
| | (5) VEGF-A | 79% | | | |
| | (6) YKL-40 | 78% | XELJANZ 5 mg twice a day; methotrexate 15 mg once a week; CIMZIA 200 mg subcutaneously every other week Leflunomide was ineffective and discontinued Patient was previously treated with ACTEMRA (ATAB) that caused a flare in arthritis XELJANZ selected as it is viewed to affect IL-6 by a different mechanism than ACTEMRA | | |
| | (7) Leptin | 66% | | | |
| | (8) SAA | 59% | | | |
| | (9) VCAM-1 | 55% | | | |
| | August 2013 Score: 43 (high moderate) | | Methotrexate (MTX) - 2, 3, 3, 4 XELJANZ (TOFAC) - 2, 4 TNF (CIMZIA) - 2, 3, 3, 5, 6 | | |
| | (1) Leptin | 84% | | | |
| | (2) MMP-3 | 75% | | | |
| | (3) VEGF-A | 74% | | | |
| | (3) CRP | 74% | | | |
| | (4) IL-6 | 57% | | | |
| | (5) YKL-40 | 46% | | | |
| | (6) Resistin | 45% | | | |
| | February 2014 Score: 37 (moderate) | | Methotrexate (MTX) - 1, 2, 3, 7 XELJANZ (TOFAC) - 3, 7, 8 TNF (CIMZIA) - 1, 2, 3, 4, 6, 8 | VECTRA DA Score - 37; decreased by 28 since August 2012 Prednisone dose could be reduced | Effective, based on VECTRA DA Score |
| | (1) VEGF-A | 89% | | | |
| | (2) CRP | 85% | | | |
| | (3) MMP-3 | 84% | | | |
| | (4) Resistin | 70% | | | |
| | (5) Leptin | 60% | | | |
| | (6) VCAM-1 | 51% | | | |
| | (7) IL-6 | 47% | | | |
| | (8) MMP-1 | 46% | | | |
| 3. | April 2012 Score: 45 (high) | | Patient was already on Methotrexate (MTX), PLAQUENIL (P), and Azathioprine (AZA) Patent recommended to increase Methotrexate (MTX); switch from AZA to | | |
| | (1) IL-6 | 95% | | | |
| | (2) MMP-3 | 77% | | | |
| | (3) VEGF-A | 59% | | | |
| | (4) VCAM-1 | 48% | | | |
| | (5) CRP | 44% | | | |
| | (6) Leptin | 40% | | | |

TABLE 3-continued

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| | | | Leflunomide (ARA); or keep MTX and AZA at the same dose and add ACTEMRA (TOCL) Patient decided to take ACTEMRA Patient declined TNF or ORENCIA (ATAB) | | |
| | March 2013 Score: 32 (moderate) | | Methotrexate (MTX) - 1, 2 ACTEMRA (TOCL) - 1, 2 Methotrexate increased 10 10 mg/ week | | |
| | (1) IL-6 | 69% | | | |
| | (2) VEFG-A | 40% | | | |
| | September 2013 Score: 26 (low) | | Methotrexate (MTX) - 1, 1 ACTEMRA (TOCL) - 1, 1 | VECTRA DA Score - 26; decreased by 19 since April 2012 | Effective, based on VECTRA DA Score |
| | (1) IL-6 | 46% | | | |
| | (1) MMP-3 | 46% | | | |
| 4. | November 2012 Score: 74 (high) | | Methotrexate (MTX) - 2, 2, 5, 5, 7 Leflunomide (ARA) - 2, 4, 5, 5, 8, 8 TNF (CIMZIA) - 2, 2, 4, 5, 7, 8, 8, 10 Methotrexate 15 mg/ week; Leflunomide 20 mg/ day; CIMZIA 200 mg every 14 days ORENCIA (ATAB) contraindicated because of patient's body weight above normal and long history of rheumatoid arthritis (ORENCIA known to be more effective in milder and earlier cases of rheumatoid arthritis. The patient has had rheumatoid arthritis for more than 20 years.) Methotrexate and ACTEMRA resulted in inflammation | | |
| | (1) Leptin | >99% | | | |
| | (2) SAA | 97% | | | |
| | (3) CRP | 97% | | | |
| | (4) VCAM1 | 95% | | | |
| | (5) IL-6 | 92% | | | |
| | (6) MMP-3 | 92% | | | |
| | (7) VEGF-A | 86% | | | |
| | (8) MMP-1 | 82% | | | |
| | (8) TNF-R1 | 81% | | | |
| | (10) YKL-40 | 71% | | | |
| | April 2013 Score: 50 (high) | | TNF (CIMZIA) - 2, 3, 4, 5, 6, 7, 9 Methotrexate (MTX) - 4, 5, 6, 7, 7 Leflunomide (ARA) - 2, 3, 4, 5, 7 ACTEMRA | | |
| | (1) Leptin | >99% | | | |
| | (2) VCAM-1 | 94% | | | |
| | (3) TNF-R1 | 78% | | | |
| | (4) SAA | 74% | | | |
| | (5) MMP-3 | 65% | | | |
| | (6) CRP | 63% | | | |
| | (7) VEGF-A | 54% | | | |

TABLE 3-continued

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| | (7) IL-6 | 54% | excluded due to bone marrow toxicity | | |
| | (9) YKL-40 | 50% | | | |
| | October 2013 Score: 42 (moderate) | | TNF (CIMZIA) - 2, 3, 4, 5, 7, 8 Methotrexate (MTX) - 5, 6, 8 Leflunomide (ARA) - 2, 3, 5, 6, 7 | VECTRA DA Score - 42; decreased by 32 since October 2012 Patient had at least 1 surgery a year in 1981-2012; no surgery since September 2012 | Effective, based on VECTRA DA Score |
| | (1) Leptin | >99% | | | |
| | (2) VCAM-1 | 95% | | | |
| | (3) TNF-R1 | 85% | | | |
| | (4) YKL-40 | 70% | | | |
| | (5) MMP-3 | 58% | | | |
| | (6) IL-6 | 52% | | | |
| | (7) MMP-1 | 49% | | | |
| | (8) VEGF-A | 42% | | | |
| 5. | March 2012 Score: 52 (high) | | Methotrexate (MTX), 10 mg/week, selected based on conventional thinking | | |
| | (1) Leptin | >99% | | | |
| | (2) YKL-40 | 98% | | | |
| | (3) MMP-3 | 97% | | | |
| | (4) VCAM-1 | 92% | | | |
| | (5) SAA | 89% | | | |
| | (6) Resistin | 84% | | | |
| | (7) IL-6 | 74% | | | |
| | (8) TNF-R1 | 69% | | | |
| | (9) MMP-1 | 55% | | | |
| | (10) VEGF-A | 53% | | | |
| | August 2012 Score: 59 (high) | | Methotrexate (MTX) and TNF (CIMZIA) selected in October 2012 based on the algorithm Methotrexate - 3, 5, 6, 10, 11 TNF (CIMZIA) - 1, 3, 5, 6, 7, 10, 11 Leflunomide (ARA) and ACTEMRA (TOCL) not selected because of hyperlipidemia ORENCIA (ATAB) and ACTEMRA were unattractive to the patient because they require intravenous administration Patient requested to switch from CIMZIA to Leflunomide in March 2013 on patient's request Leflunomide - 1, 3, 5, 7, 7, 7 | VECTRA DA Score - 59; increased by 7 since March 2012 (5 months treatment only) Patient did not followed the treatment as advised | VECTRA DA analysis was not performed after switching the treatment |
| | (1) VCAM-1 | 97% | | | |
| | (2) Leptin | 97% | | | |
| | (3) MMP-3 | 95% | | | |
| | (4) YKL-40 | 94% | | | |
| | (5) SAA | 92% | | | |
| | (6) Resistin | 82% | | | |
| | (7) IL-6 | 79% | | | |
| | (7) TNF-R1 | 79% | | | |
| | (7) MMP-1 | 79% | | | |
| | (10) CRP | 67% | | | |
| | (11) VEGF-A | 48% | | | |
| 6. | March 2012 Score: 74 (high) | | Patient already on Leflunomide (ARA) based on conventional thinking Based on preliminary VECTRA DA analysis, TNF (CIMZIA) added Patient declined | | |
| | (1) IL-6 | 98% | | | |
| | (2) SAA | 97% | | | |
| | (3) CRP | 93% | | | |
| | (4) MMP-3 | 91% | | | |
| | (5) Leptin | 90% | | | |
| | (6) VCAM-1 | 85% | | | |
| | (7) VEGF-A | 84% | | | |
| | (8) TNF-R1 | 73% | | | |
| | (9) Resistin | 63% | | | |

TABLE 3-continued

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| | (10) YKL-40 | 41% | Methotrexate (MTX) due to side effects in the past ORENCIA (ATAB) not selected because of intravenous administration and patient's high body fat ACTEMRA (TOCL) was not selected because of patient preference and expense | | |
| | (11) MMP-1 | 40% | | | |
| | July 2012 Score: 70 (high) | | Based on preliminary VECTRA DA analysis, Leflunomide (ARA) and ACTEMRA (TOCL) were selected Patient stopped taking Leflunomide TNF (CIMZIA) discontinued, patient switched to ACTEMRA based on preliminary VECTRA DA analysis, August 2012 | | |
| | (1) IL-6 | 97% | | | |
| | (2) SAA | 97% | | | |
| | (3) Leptin | 94% | | | |
| | (4) VCAM-1 | 91% | | | |
| | (5) MMP-3 | 91% | | | |
| | (6) CRP | 90% | | | |
| | (7) VEGF-A | 85% | | | |
| | (8) TNF-R1 | 66% | | | |
| | (9) Resistin | 57% | | | |
| | October 2012 Score: 54 (high) | | ACTEMRA (TOCL) - 1, 4 ACTEMRA (TOCL) dose increased from 4 mg/kg to 6 mg/kg | | |
| | (1) IL-6 | >99% | | | |
| | (2) VCAM-1 | 96% | | | |
| | (3) Leptin | 91% | | | |
| | (4) MMP-3 | 88% | | | |
| | (5) Resistin | 57% | | | |
| | (6) TNF-R1 | 45% | | | |
| | February 2013 Score: 50 (high) | | ACTEMRA (TOCL) - 1, 5 | VECTRA DA Score - 50; decreased by 24 since March 2012 While on ACTEMRA, conventional markers of inflammation - ESR and CRP level - were normalized | Effective, based on VECTRA DA Score |
| | (1) IL-6 | >99% | | | |
| | (2) VCAM-1 | 91% | | | |
| | (3) Leptin | 88% | | | |
| | (4) Resistin | 70% | | | |
| | (5) MMP-3 | 61% | | | |
| 7. | November 2012 Score: 44 (high moderate) | | Methotrexate (MTX) - 2, 4, 5 TNF (HUMIRA) - 2, 3, 5 ORENCIA (ATAB) not selected because of intravenous administration and patient's | | |
| | (1) Leptin | >99% | | | |
| | (2) CRP | 86% | | | |
| | (3) Resistin | 63% | | | |
| | (4) IL-6 | 62% | | | |
| | (5) VEGF-A | 42% | | | |
| | (6) TNF-R1 | 40% | | | |

TABLE 3-continued

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| | | | high body fat ACTEMRA (TOCL) not selected because of intravenous administration | | |
| | February 2013 Score: 33 (moderate) | | Methotrexate (MTX) - 3, 4 TNF - 2, 3 | | |
| | (1) Leptin | >99% | HUMIRA switched | | |
| | (2) Resistin | 79% | to Embrel, which | | |
| | (3) CRP | 70% | developed | | |
| | (4) IL-6 | 58% | allergic reaction, April 2013 TNF replaced with ORENCIA (ATAB), May 2013 ORENCIA (injection) - 1, 3, 4 ORENCIA replaced with TNF (CIMZIA) due to lack of efficacy, June 2013 | | |
| | August 2013 Score: 38 (moderate) | | Methotrexate (MTX) - 2, 4 TNF - 2, 3, 5 | VECTRA DA Score - 38; decreased by 6 since | VECTRA DA analysis was not performed |
| | (1) Leptin | >99% | Methotrexate | November 2012 | after switching |
| | (2) CRP | 90% | increased to 17.5 mg/ | On February 2014 visit, | the treatment |
| | (3) Resistin | 82% | week | the patient has | |
| | (4) IL-6 | 54% | | less than 15 | |
| | (5) TNF-R1 | 40% | | minutes morning stiffness | |
| 8. | August 2012 Score: 49 (high) | | Based on the preliminary | | |
| | (1) IL-6 | 92% | VECTRA DA | | |
| | (2) VCAM-1 | 75% | analysis | | |
| | (3) VEGF-A | 67% | Methotrexate | | |
| | (3) CRP | 67% | (MTX) and | | |
| | (5) MMP-1 | 55% | ORENCIA (ATAB) | | |
| | (6) Leptin | 51% | were selected | | |
| | (7) YKL-40 | 50% | Methotrexate | | |
| | (8) MMP-3 | 40% | and Prednisone started October 2012; ORENCIA added December 2012 Prednisone was not selected based on the algorithm ORENCIA selected based on negative rheumatoid factor TNF was not selected based on negative rheumatoid factor Patient did not prefer ACTEMRA (TOCL) because of intravenous administration | | |
| | March 2013 Score: 29 (low) | | Methotrexate (MTX) - 2, 3, 4 | Patient stated that she felt 80-85% | |
| | (1) Leptin | 94% | ORENCIA (ATAB) - | better and | |
| | (2) MMP-3 | 60% | 1, 2, 4 | was able to walk | |

TABLE 3-continued

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| | (3) VEGF-A | 48% | Prednisone (not based on the algorithm) | for 2 miles | |
| | (4) CRP | 40% | | | |
| | August 2013 Score: 33 (moderate) | | Methotrexate (MTX) - none ORENCIA (ATAB) - 1 Leflunomide (ARA) added based on March 2013 VECTRA DA profile - MMP-3 | | |
| | (1) Leptin | 47% | | | |
| | December 2013 Score: 46 (high) | | Methotrexate (MTX) - 2, 3, 4 ORENCIA (ATAB) - 1, 3, 4, 5 Leflunomide (ARA) - 3, 5 ORENCIA and Leflunomide discontinued and ACTEMRA (TOCL) begun, April 2014 ACTEMRA - 2, 3, 4 Sulfasalazine (S) added June 2014 due to oral cancers due to methotrexate based on 3 elevated biomarkers - VEFG-A, IL-6, CRP; Methotrexate discontinued Patient on ACTEMRA and Sulfasalazine | VECTRA DA Score - 46; decreased by 3 since August 2012 | VECTRA DA analysis was not performed after switching the treatment to include Sulfasalazine |
| | (1) Leptin | 89% | | | |
| | (2) VEGF-A | 74% | | | |
| | (3) IL-6 | 66% | | | |
| | (4) CRP | 65% | | | |
| | (5) VCAM-1 | 48% | | | |
| 9. | May 2012 Score: 73 (high) | | Based on preliminary VECTRA DA analysis, Methotrexate (MTX) and ACTEMRA (TOCL) were selected ACTEMRA 4 mg/kg started May 2012 and then increased to 8 mg/kg August 2012 Methotrexate added October 2012 ACTEMRA and Methotrexate discontinued January 2013 due to cranial palsies Methotrexate resumed February 2013 | Patient was able to wean off steroids and was able to transfer on his own for the first time in 25 years, by December 2012 | |
| | (1) IL-6 | 97% | | | |
| | (2) TNF-R1 | 96% | | | |
| | (3) CRP | 96% | | | |
| | (4) Leptin | 94% | | | |
| | (5) SAA | 89% | | | |
| | (6) VEGF-A | 83% | | | |
| | (6) Resistin | 83% | | | |
| | (8) YKL-40 | 81% | | | |
| | (9) MMP-3 | 78% | | | |
| | (10) VCAM-1 | 63% | | | |
| | March 2013 Score: 73 (high) | | Methotrexate (MTX) - 1, 3, 7, 8 ACTEMRA (TOCL) - 1, 3, 5, 7, 8 ACTEMRA restrated March 2013 | VECTRA DA Score - 73; no change | Patient expired due to cardiovascular disease, June 2013 |
| | (1) IL-6 | >99% | | | |
| | (2) TNF-R1 | 97% | | | |
| | (3) CRP | 96% | | | |
| | (4) VCAM-1 | 93% | | | |
| | (5) YKL-40 | 91% | | | |
| | (6) Resistin | 84% | | | |
| | (7) SAA | 72% | | | |
| | (8) MMP-3 | 64% | | | |

TABLE 3-continued

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| 10. | November 2011 Score: 39 (moderate) | | Methotrexate (MTX), 10 mg/week based on conventional thinking | | |
| | (1) SAA | 80% | | | |
| | (2) VEGF-A | 63% | | | |
| | (3) CRP | 45% | | | |
| | April 2012 Score: 33 (moderate) | | Methotrexate (MTX) increased to 15 mg/week; Ridaura added due to tenderness in joints Selection based on conventional thinking | | |
| | (1) YKL-40 | 72% | | | |
| | (2) SAA | 65% | | | |
| | (3) VEGF-A | 59% | | | |
| | August 2012 Score: 55 (high) | | Riduara stopped and ORENCIA (ATAB) started based on conventional thinking | | |
| | (1) SAA | 97% | | | |
| | (2) YKL-40 | 88% | | | |
| | (3) CRP | 85% | | | |
| | (4) VCAM-1 | 65% | | | |
| | (5) VEGF-A | 57% | | | |
| | (6) MMP-3 | 46% | | | |
| | (7) MMP-1 | 40% | | | |
| | December 2012 Score: 55 (high) | | Methotrexate (MTX) - 1, 3, 3, 5 TNF (HUMIRA) - 1, 2, 3, 5 ORENCIA (ATAB) discontinued ACTEMRA (TOCL) not selected due to intravenous administration and effect on plasma lipids | | |
| | (1) SAA | 91% | | | |
| | (2) YKL-40 | 83% | | | |
| | (3) IL-6 | 81% | | | |
| | (3) CRP | 81% | | | |
| | (5) VEGF-A | 64% | | | |
| | May 2013 Score: 23 (low) | | Methotrexate (MTX) - 1, 2 TNF (HUMIRA) - 1, 2 | Patient reported that his fatigue had improved and had little morning stiffness | |
| | (1) VEGF-A | 44% | | | |
| | (2) MMP-3 | 43% | | | |
| | December 2013 Score: 27 (low) | | Methotrexate (MTX) - 2 TNF - 1, 2, 3 | VECTRA DA Score - 27; decreased by 12 since November 2011 Patient able to rake leaves and snow, and diminished morning stiffness | Effective, based on based on VECTRA DA Score |
| | (1) YKL-40 | 81% | | | |
| | (2) VEGF-A | 53% | | | |
| | (3) MMP-1 | 41% | | | |
| 11. | October 2011 Score: 47 (high) | | Based on preliminary VECTRA DA analysis, Leflunomide (ARA) and ACTEMRA (TOCL) were selected Patient was receiving RITUXAN and oral Leflunomide based on conventional treatment Patient had previously been | | |
| | (1) MMP-3 | 94% | | | |
| | (2) SAA | 89% | | | |
| | (3) IL-6 | 74% | | | |
| | (4) TNF-R1 | 42% | | | |
| | (4) Leptin | 42% | | | |

TABLE 3-continued

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| | November 2012 Score: 45 (high) (1) SAA (2) MMP-3 (3) IL-6 (4) VCAM-1 (5) Leptin (6) VEGF-A (7) CRP | 89% 74% 62% 60% 59% 48% 40% | Methotrexate or TNF, which were not effective Patient was able to discontinue Prednisone and Leflunomide (ARA) But, flares in many joints in September 2012 and October 2012 Leflunomide - 1, 2, 3, 4 ACTEMRA (TOCL) - 1, 2, 3, 6, 7 Leflunomide discontinued by patient's other rheumatologist due to below normal WBC count Patient switched to XELJANZ (TOFAC) and Methotrexate March 2013 and May 2013, respectively Methotrexate (MTX) - 1, 2, 3, 6, 7 XELJANZ (TOFAC) - 2, 3 Other combinations previously tried - TNF, ACTEMRA, RITUXAN and other disease modifying drugs | | |
| | August 2013 Score: 35 (moderate) (1) MMP-3 (2) IL-6 (2) SAA (4) Leptin | 73% 65% 65% 46% | Methotrexate (MTX) - 1, 2, 2 XELJANZ (TOFAC) - 1, 2 Methotrexate increased from 12.5 to 15 mg/week Methotrexate reduced to 10 mg/week due to hair loss, April 2014 | VECTRA DA Score - 35; decreased by 12 since October 2011 Patient no longer had morning stiffness, December 2013 | Effective, based on VECTRA DA Score |
| 12. | September 2011 Score: 78 (high) (1) MMP-3 (2) CRP (2) IL-6 (4) SAA (5) MMP-1 (6) YKL-40 (7) TNF-R1 (8) VEGF-A (9) VCAM-1 (10) Resistin | >99% 98% 98% 97% 96% 87% 82% 56% 52% 48% | Based on preliminary VECTRA DA analysis, Methotrexate (MTX) and ACTEMRA (TOCL) were selected Patient had previously been TNF or ORENCIA (ATAB), which were not effective | | |

TABLE 3-continued

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| | | | Patient had allergic reaction to ACTEMRA (TOCL); switched to TNF (HUMIRA), October 2012 | | |
| | December 2012 Score: 34 (moderate) | | TNF (HUMIRA) - 1, 2, 4, 5, 6, 7, 8, 9, 10 Methotrexate (MTX) - 1, 3 Leflunomide (ARA) - 1, 2, 3, 4 TNF (HUMIRA) - 1, 2, 4 | | |
| | (1) MMP-3 | 64% | | | |
| | (2) MMP-1 | 58% | | | |
| | (3) IL-6 | 52% | | | |
| | (4) VCAM-1 | 49% | | | |
| | (5) YKL-40 | 40% | | | |
| | May 2014 Score: 31 (low moderate) | | Methotrexate (MTX) - 1 Leflunomide (ARA) - 1,3 TNF (HUMIRA) - 1, 3 | VECTRA DA Score - 31; decreased by 47 since September 2011 Patient no longer experienced morning stiffness and no longer had active synovitis or effusions of the previously affected joints | Effective, based on VECTRA DA Score |
| | (1) MMP-3 | 80% | | | |
| | (2) Leptin | 55% | | | |
| | (3) MMP-1 | 51% | | | |
| 13. | August 2011 Score: 57 (high) | | Patient was already on Prednisone 5 mg; Methotrexate (MTX) 7.5 mg/week; ACTEMRA (TOCL) Treatments were not selected based on the algorithm | | |
| | (1) IL-6 | >99% | | | |
| | (2) Leptin | 84% | | | |
| | (3) MMP-3 | 81% | | | |
| | (4) SAA | 77% | | | |
| | (5) VCAM-1 | 75% | | | |
| | (6) TNF-R1 | 71% | | | |
| | (7) YKL-40 | 58% | | | |
| | (8) Resistin | 53% | | | |
| | (9) VEGF-A | 40% | | | |
| | May 2012 Score: 53 (high) | | Based on preliminary VECTRA DA analysis, Methotrexate (MTX) and ACTEMRA (TOCL) were selected Methotrexate dose changed; ACTEMRA dose increased from 4 mg/kg to 6 mg/kg, May 2012 Patient had previously been TNF, Leflunomide (ARA), or ORENCIA (ATAB), which were not effective | | |
| | (1) IL-6 | >99% | | | |
| | (2) MMP-3 | 82% | | | |
| | (3) TNF-R1 | 64% | | | |
| | (4) VCAM-1 | 61% | | | |
| | (5) Resistin | 54% | | | |
| | (6) YKL-40 | 52% | | | |
| | July 2012 Score: 49 (high) | | Based on preliminary VECTRA DA analysis, Methotrexate | | |
| | (1) IL-6 | >99% | | | |
| | (2) VCAM-1 | 82% | | | |
| | (3) TNF-R1 | 77% | | | |

TABLE 3-continued

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| | (4) MMP-3 | 74% | (MTX) and | | |
| | (5) YKL-40 | 67% | ACTEMRA (TOCL) | | |
| | (6) VEGF-A | 46% | were selected | | |
| | November 2012 | | Methotrexate | | |
| | Score: 44 | | (MTX) - 1, 3, 7 | | |
| | (moderate) | | ACTEMRA (TOCL) - | | |
| | (1) IL-6 | >99% | 1, 3, 4, 7 | | |
| | (2) VCAM-1 | 84% | ACTEMRA | | |
| | (3) MMP-3 | 80% | discontinued and | | |
| | (4) TNF-R1 | 62% | replaced with | | |
| | (4) YKL-40 | 62% | TNF (CIMZIA), | | |
| | (6) Resistin | 58% | January 2013. CIMZIA | | |
| | (7) VEGF-A | 45% | is a better TNF | | |
| | | | than previously | | |
| | | | given TNF to the | | |
| | | | patient | | |
| | | | TNF (CIMZIA) - | | |
| | | | 2, 3, 4, 4, 6, 7 | | |
| | | | Patient could not | | |
| | | | tolerate | | |
| | | | Leflunomide | | |
| | | | (ARA) in the | | |
| | | | past | | |
| | March 2013 | | Methotrexate | | |
| | Score: 25 (low) | | (MTX) - 1 | | |
| | (1) MMP-3 | 77% | TNF (CIMZIA) - | | |
| | (2) YKL-40 | 71% | 1, 2, 3 | | |
| | (3) TNF-R1 | 62% | | | |
| | (4) Leptin | 53% | | | |
| | June 2013 | | Methotrexate | VECTRA DA Score - | Effective, based |
| | Score: 36 | | (MTX) - 2, 5 | 36; decreased | on VECTRA DA |
| | (moderate) | | TNF (CIMZIA) - | by 21 since | Score |
| | (1) YKL-40 | 79% | 1, 2, 3, 5, 6, 7 | August 2011 | |
| | (2) MMP-3 | 73% | Due to | | |
| | (3) TNF-R1 | 65% | interceding | | |
| | (4) Leptin | 61% | medical | | |
| | (5) SAA | 56% | problems, it was | | |
| | (6) VCAM-1 | 54% | difficult to | | |
| | (7) Resistin | 53% | maintain | | |
| | | | Methotrexate | | |
| | | | and CIMZIA on a | | |
| | | | regular basis | | |
| 14. | September 2012 | | The patient was | | |
| | Score: 59 (high) | | previously on | | |
| | (1) IL-6 | 91% | Leflunomide | | |
| | (1) SAA | 91% | (ARA) and | | |
| | (3) MMP-3 | 89% | Azathioprine | | |
| | (4) YKL-40 | 87% | Based on the | | |
| | (5) VCAM-1 | 67% | VECTRA DA | | |
| | (6) TNF-R1 | 61% | analysis, | | |
| | (6) CRP | 61% | Methtrexate | | |
| | | | (MTX) and | | |
| | | | Leflunomide | | |
| | | | started, October 2012 | | |
| | | | Methotrexate | | |
| | | | (MTX) - 1, 1, 3, 6 | | |
| | | | Leflunomide | | |
| | | | (ARA) - 1, 1, 3, | | |
| | | | 5, 6 | | |
| | | | TNF (CIMZIA) | | |
| | | | added, December 2013: | | |
| | | | TNF (CIMZIA) - | | |
| | | | 1, 3, 4, 5, 6 | | |
| | | | Prednisone | | |
| | | | added (not | | |
| | | | based on the | | |
| | | | algorithm) | | |

TABLE 3-continued

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| | March 2013 Score: 38 (moderate) | | Leflunomide discontinued due to bone marrow toxicity Methotrexate (MTX) - 1, 2, 4, 5 TNF (CIMZIA) - 1, 2, 3, 4, 6 Azathioprine (not based on the algorithm) | Patient feels "75% better," March 2013 | |
| | (1) MMP-3 | 91% | | | |
| | (2) TNF-R1 | 52% | | | |
| | (3) YKL-40 | 52% | | | |
| | (4) SAA | 52% | | | |
| | (5) IL-6 | 49% | | | |
| | (6) VCAM-1 | 43% | | | |
| | September 2013 Score: 31 (low moderate) | | Methotrexate (MTX) - 1, 4 TNF (CIMZIA) - 1, 3, 4, 5, 6, 7 Azathioprine | | |
| | (1) MMP-3 | 94% | | | |
| | (2) Leptin | 60% | | | |
| | (3) VCAM-1 | 54% | | | |
| | (4) SAA | 53% | | | |
| | (5) MMP-1 | 52% | | | |
| | (6) TNF-R1 | 47% | | | |
| | (7) YKL-40 | 47% | | | |
| | February 2014 Score: 33 (low moderate) | | Methotrexate (MTX) - 1 TNF (CIMZIA) - 1, 2, 3, 3 Azathioprine | VECTRA DA Score - 33; decreased by 26 since September 2012 | Effective, based on VECTRA DA Score |
| | (1) MMP-3 | 80% | | | |
| | (2) VCAM-1 | 60% | | | |
| | (3) TNF-R1 | 53% | | | |
| | (3) MMP-1 | 53% | | | |
| 15. | July 2012 Score: 54 (high) | | Patient already on treatments for lupus erythematous - Cell cept and Benlysta, and Methotrexate Benlysta discontinued and ACTEMRA TOCL) started based on Biomarker profiles Based on preliminary VECTRA DA analysis, ACTEMRA was selected Patient had previously been TNF, Leflunomide (ARA), or ORENCIA (ATAB), which were not effective So, patient on Methotrexate (MTX) and ACTEMRA (TOCL) | | |
| | (1) IL-6 | >99% | | | |
| | (1) Leptin | >99% | | | |
| | (3) VEGF-A | 88% | | | |
| | (4) YKL-40 | 72% | | | |
| | (5) CRP | 66% | | | |
| | (6) VCAM-1 | 54% | | | |
| | December 2012 Score: 55 (high) | | Methotrexate (MTX) - 1, 4, 7 ACTEMRA (TOCL) - 1, 4, 5, 6, 7 ACTEMRA discontinued and intravenous | | |
| | (1) IL-6 | >99% | | | |
| | (2) VCAM-1 | 95% | | | |
| | (3) Leptin | 94% | | | |
| | (4) VEGF-A | 85% | | | |
| | (5) YKL-40 | 82% | | | |

TABLE 3-continued

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| | (6) Resistin | 71% | steroids and | | |
| | (7) MMP-3 | 64% | XELJANZ (TOFAC) started, December 2012 XELJANZ - 1, 7 Developed pneumonia, April 2013 and Methotrexate and XELJANZ were stopped | | |
| | January 2014 Score: 52 (high) | | Patient started on RITUXAN based on | VECTRA DA Score - 52; decreased | VECTRA DA analysis was |
| | (1) Leptin | >99% | her past | by 2 since | not performed |
| | (2) IL-6 | 94% | experience with | July 2012 | after switching |
| | (3) VEGF-A | 76% | the drug, March 2014 | | the treatment |
| | (4) YKL-40 | 72% | Methotrexate 20 mg/ | | |
| | (4) CRP | 72% | week, April 2014 | | |
| | (6) VCAM-1 | 71% | Leflunomide | | |
| | (7) MMP-3 | 52% | (ARA) added May 2014 due to past failures with TNF, ORENCIA (ATAB), ACTEMRA (TOCL) Leflunomide (ARA) - 2, 6, 7 | | |
| 16. | February 2012 Score: 64 (high) | | Patient initially on Methotrexate | | |
| | (1) Leptin | >99% | (MTX) 15 mg/ | | |
| | (2) SAA | 97% | week, | | |
| | (3) IL-6 | 88% | PLAQUENIL (P) | | |
| | (4) CRP | 80% | 200 mg twice a | | |
| | (5) MMP-3 | 76% | day, and | | |
| | (5) Resistin | 76% | Prednisone 7 mg/ | | |
| | (7) YKL-40 | 72% | day. | | |
| | (8) MMP-1 | 71% | Started on | | |
| | (9) VEGF-A | 68% | Azathioprine 100 mg/ | | |
| | (10) TNF-R1 | 65% | day because | | |
| | (11) VCAM-1 | 43% | the patient was reluctant to start biologic response modifiers and had concerns about blood pressure and leflunomide PLAQUENIL stopped Azathioprine (Imuran) discontinued TNF (CIMZIA) started Treatment methods were not selected based on the algorithm | | |
| | March 2013 Score: 38 (moderate) | | TNF (CIMZIA) - 2, 3, 4, 6, 7 Methotrexate | | |
| | (1) Leptin | 98% | (MTX) - 4, 4 | | |
| | (2) Resistin | 72% | Azathioprine | | |
| | (3) YKL-40 | 60% | (Imuran) (not | | |
| | (4) VEGF-A | 57% | selected based | | |
| | (4) IL-6 | 57% | on the algorithm) | | |

TABLE 3-continued

Patient Data with Biomarker Analysis Details

| Patient No. | VECTRA ® DA Test-Score (Arthritis Activity) and Biomarkers Having At Least 40% Elevated Level | | Treatment Method Selection | Disease Activity Measurement (Change in Disease Activity Indices After Treatment) | Treatment Outcome |
|---|---|---|---|---|---|
| | (6) MMP-1 | 53% | ACTEMRA (TOCL) was not selected due to patient's preference | | |
| | (7) TNF-R1 | 50% | | | |
| | October 2013 Score: 46 (high) | | TNF (CIMZIA) - 3, 3, 5, 5, 7 | | |
| | (1) Leptin | >99% | Methotrexate | | |
| | (2) IL-6 | 82% | (MTX) - 2, 5, 5, 7 | | |
| | (3) MMP-1 | 59% | Azathioprine | | |
| | (3) YKL-40 | 59% | (Imuran) (not | | |
| | (5) MMP-3 | 45% | selected based | | |
| | (5) SAA | 45% | on the algorithm) | | |
| | (7) VEGF-A | 43% | TNF (CIMZIA) discontinued; intravenous ORENCIA started ORENCIA (ATAB) - 1, 2, 5 ORENCIA chosen over ACTEMRA for safety and toxicity reasons Patient declined Leflunomide (ARA) because of concerns about effect of Leflunomide on blood pressure and cholesterol | | |
| | January 2014 Score: 62 | | Methotrexate (MTX) - 2, 4, 5, 7, 9 | VECTRA DA Score - 62; decreased by 2 since February 2012 XELJANZ allowed tapering of oral steroid, Prednisone | VECTRA DA analysis was not performed after switching the treatment |
| | (1) Leptin | 98% | XELJANZ | | |
| | (2) SAA | 97% | (TOFAC) - 4, 5, 8 | | |
| | (3) Resistin | 86% | ORENCIA (ATAB) | | |
| | (4) IL-6 | 85% | and Azathioprine | | |
| | (5) MMP-3 | 81% | discontinued due | | |
| | (5) YKL-40 | 81% | to inefficacy | | |
| | (7) CRP | 73% | TNF (CIMZIA) | | |
| | (8) MMP-1 | 69% | and | | |
| | (9) VEGF-A | 68% | Methotrexate | | |
| | (10) TNF-R1 | 62% | previously tried | | |
| | (11) VCAM-1 | 41% | without success ACTEMRA (TOCL) not in formulary XELJANZ 5 mg twice a day added March 2014 | | |

Figure 8:
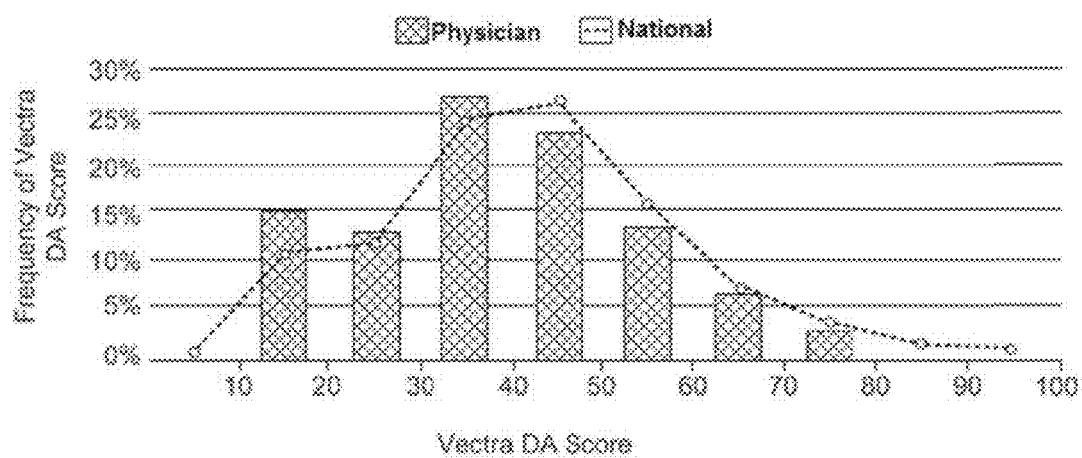
FIG. 8 shows a comparison of the distribution of post-treatment VECTRA DA Scores in the inventor's patient population of 575 total patients with 75% patients who were treated by the treatment methods that were selected based on the algorithm as described in Example 3 (shown as physician distribution by the bar graph) and the distribution of post-treatment VECTRA DA Scores in a random patient population available nationwide (shown as national distribution by the dotted curve) for the same duration of treatment.

A comparison of the distribution of the post-treatment VECTRA DA Scores in the inventor's patient population of 575 patients with 75% patients who were treated with treatment methods selected based on the algorithm (shown as physician distribution by the bar graph) with the distribution of post-treatment VECTRA DA Score of a control population (a random patient population available nationwide that was treated with treatment methods that were not selected based on the algorithm, shown by the dotted curve) is shown in FIG. 8. The comparison shows that the patients treated with methods that were selected based on the algorithm have more patients in low disease activity state and less patients in high disease activity states than the control population after treatment. Additionally, the patients treated with treatment methods selected based on the algorithm have lower disease activity than the control population.

Given the heterogeneous group of patients, it is difficult to demonstrate a single consistent feature. But a composite picture shows an improvement in both laboratory and clinical manifestations of the disease. A comparison of the distribution of VECTRA DA Scores in a collection of patients after treatment based on the algorithm and distribution of VECTRA DA Scores in a random patient population that were treated nationwide showed that there are more patients that have VECTRA DA Score corresponding to low disease activity and the patient population has lower disease activity than the nationwide population after treatment (in an objective blind comparison) (FIG. 8). Thus, the treatment methods selected based on the algorithm are more effective than treatment methods selected nationwide without the algorithm.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for treating a patient with rheumatoid arthritis with one or more treatments selected from the group consisting of PLAQUENIL (or Hydroxychloroquine), Sulfasalazine, Methotrexate, ARAVA (or Leflunomide), Tumor Necrosis Factor-α inhibitors, Atabacept (or ORENCIA), Tocilizumab (or ACTEMRA), RITUXAN (or Rituximab), and Tofacitinib (or XELJANZ), which comprises:
   i. Determining serum levels in the patient of a group of biomarkers comprising Vascular Cell Adhesion Molecule 1, Vascular Endothelial Growth Factor-A, Interleukin-6, Tumor Necrosis Factor Receptor Type 1, Matrix Metalloproteinase-1, Matrix Metalloproteinase-3, YKL-40, Leptin, Resistin, Serum Amyloid A, and C-Reactive Protein;
   ii. Identifying at least two biomarkers each one with at least 40% elevated serum level over control serum level, wherein if the at least two biomarkers with at least 40% elevated levels are:
   1) Vascular Cell Adhesion Molecule 1 and Vascular Endothelial Growth Factor-A, selecting treatment with Tumor Necrosis Factor-α inhibitors;
   2) Vascular Cell Adhesion Molecule 1 and Interleukin-6, selecting treatment with one or more of ARAVA (Leflunomide) and Atabacept (ORENCIA);
   3) Vascular Cell Adhesion Molecule 1 and Tumor Necrosis Factor Receptor Type 1, selecting treatment with one or more of ARAVA (Leflunomide) and Tumor Necrosis Factor-α inhibitors;
   4) Vascular Cell Adhesion Molecule 1 and Matrix Metalloproteinase-1, selecting treatment with one or more of ARAVA (Leflunomide) and Tumor Necrosis Factor-α inhibitors;
   5) Vascular Cell Adhesion Molecule 1 and Matrix Metalloproteinase-3, selecting treatment with one or more of ARAVA (or Leflunomide), Tumor Necrosis Factor-α inhibitors and Atabacept (or ORENCIA);
   6) Vascular Cell Adhesion Molecule 1 and YKL-40, selecting treatment with Tumor Necrosis Factor-α inhibitors;
   7) Vascular Cell Adhesion Molecule 1 and Resistin, selecting treatment with Tumor Necrosis Factor-α inhibitors;
   8) Vascular Cell Adhesion Molecule 1 and Serum Amyloid A, selecting treatment with one or more of ARAVA (or Leflunomide) and Tumor Necrosis Factor-α;
   9) Vascular Cell Adhesion Molecule 1 and C-Reactive Protein, selecting treatment with one or more of Tumor Necrosis Factor-α inhibitors and Atabacept (or ORENCIA);
   10) Vascular Endothelial Growth Factor-A and Interleukin-6, selecting treatment with one or more of Sulfasalazine, Methotrexate and Tocilizumab (or ACTEMRA);
   11) Vascular Endothelial Growth Factor-A and Tumor Necrosis Factor Receptor Type 1, selecting treatment with one or more of Sulfasalazine and Tumor Necrosis Factor-α inhibitors;
   12) Vascular Endothelial Growth Factor-A and Matrix Metalloproteinase-1, selecting treatment with one or more of Tumor Necrosis Factor-α inhibitors and Tocilizumab (or ACTEMRA);
   13) Vascular Endothelial Growth Factor-A and Matrix Metalloproteinase-3, selecting treatment with one or more of Sulfasalazine, Methotrexate, Tumor Necrosis Factor-α inhibitors and Tocilizumab (or ACTEMRA);
   14) Vascular Endothelial Growth Factor-A and YKL-40, selecting treatment with one or more of Tumor Necrosis Factor-α inhibitors and Tocilizumab (or ACTEMRA);
   15) Vascular Endothelial Growth Factor-A and Resistin, selecting treatment with Tumor Necrosis Factor-α inhibitors;
   16) Vascular Endothelial Growth Factor-A and Serum Amyloid A, selecting treatment with one or more of Sulfasalazine, Methotrexate, Tumor Necrosis Factor-α inhibitors and Tocilizumab (or ACTEMRA);
   17) Vascular Endothelial Growth Factor-A and C-Reactive Protein, selecting treatment with one or more of Sulfasalazine, Methotrexate, Tumor Necrosis Factor-α inhibitors and Tocilizumab (or ACTEMRA);
   18) Interleukin-6 and Tumor Necrosis Factor Receptor Type 1, selecting treatment with one or more of Sulfasalazine and ARAVA (or Leflunomide);
   19) Interleukin-6 and Matrix Metalloproteinase-1, selecting treatment with one or more of ARAVA (or Leflunomide), Tocilizumab (or ACTEMRA) and Tofacitinib (or XELJANZ);
   20) Interleukin-6 and Matrix Metalloproteinase-3, selecting treatment with one or more of Sulfasalazine, Methotrexate, ARAVA (or Leflunomide), Atabacept (or ORENCIA), Tocilizumab (or ACTEMRA) and Tofacitinib (or XELJANZ);
   21) Interleukin-6 and YKL-40, selecting treatment with one or more of Tocilizumab (or ACTEMRA);
   22) Interleukin-6 and Serum Amyloid A, selecting treatment with one or more of PLAQUENIL (or Hydroxychloroquine), Sulfasalazine, Methotrexate, ARAVA (or Leflunomide) and Tocilizumab (or ACTEMRA);
   23) Interleukin-6 and C-Reactive Protein, selecting treatment with one or more of PLAQUENIL (or Hydroxychloroquine), Sulfasalazine, Methotrexate, Atabacept (or ORENCIA), Tocilizumab (or ACTEMRA) and RITUXAN (or Rituximab);
   24) Tumor Necrosis Factor Receptor Type 1 and Matrix Metalloproteinase-1, selecting treatment with one or more of ARAVA (or Leflunomide) and Tumor Necrosis Factor-α inhibitors;
   25) Tumor Necrosis Factor Receptor Type 1 and Matrix Metalloproteinase-3, selecting treatment with one or more of Sulfasalazine, ARAVA (or Leflunomide) and Tumor Necrosis Factor-α inhibitors;
   26) Tumor Necrosis Factor Receptor Type 1 and YKL-40, selecting treatment with Tumor Necrosis Factor-α inhibitors;

27) Tumor Necrosis Factor Receptor Type 1 and Resistin selecting treatment with Tumor Necrosis Factor-α inhibitors;
28) Tumor Necrosis Factor Receptor Type 1 and Serum Amyloid A, selecting treatment with one or more of Sulfasalazine, ARAVA (or Leflunomide) and Tumor Necrosis Factor-α inhibitors;
29) Tumor Necrosis Factor Receptor Type 1 and C-Reactive Protein, selecting treatment with one or more of Sulfasalazine and Tumor Necrosis Factor-α inhibitors;
30) Matrix Metalloproteinase-1 and Matrix Metalloproteinase-3, selecting treatment with one or more of ARAVA (or Leflunomide), Tumor Necrosis Factor-α inhibitors, Tocilizumab (or ACTEMRA) and Tofacitinib (or XELJANZ);
31) Matrix Metalloproteinase-1 and YKL-40, selecting treatment with one or more of Tumor Necrosis Factor-α inhibitors and Tocilizumab (or ACTEMRA);
32) Matrix Metalloproteinase-1 and Resistin, selecting treatment with Tumor Necrosis Factor-α inhibitors;
33) Matrix Metalloproteinase-1 and Serum Amyloid A, selecting treatment with one or more of ARAVA (or Leflunomide), Tumor Necrosis Factor-α inhibitors and Tocilizumab (or ACTEMRA);
34) Matrix Metalloproteinase-1 and C-Reactive Protein, selecting treatment with one or more of Tumor Necrosis Factor-α inhibitors and Tocilizumab (or ACTEMRA);
35) Matrix Metalloproteinase-3 and YKL-40, selecting treatment with one or more of Tumor Necrosis Factor-α inhibitors and Tocilizumab (or ACTEMRA);
36) Matrix Metalloproteinase-3 and Resistin, selecting treatment with Tumor Necrosis Factor-α inhibitors;
37) Matrix Metalloproteinase-3 and Serum Amyloid A, selecting treatment with one or more of Sulfasalazine, Methotrexate, ARAVA (or Leflunomide), Tumor Necrosis Factor-α inhibitors and Tocilizumab (or ACTEMRA);
38) Matrix Metalloproteinase-3 and C-Reactive Protein, selecting treatment with one or more of Sulfasalazine, Methotrexate, Tumor Necrosis Factor-α inhibitors, Atabacept (or ORENCIA) and Tocilizumab (or ACTEMRA);
39) YKL-40 and Resistin, selecting treatment with Tumor Necrosis Factor-α inhibitors;
40) YKL-40 and Serum Amyloid A, selecting treatment with one or more of Tumor Necrosis Factor-α inhibitors and Tocilizumab (or ACTEMRA);
41) YKL-40 and C-Reactive Protein, selecting treatment with one or more of Tumor Necrosis Factor-α inhibitors and Tocilizumab (or ACTEMRA);
42) Resistin and Serum Amyloid A, selecting treatment with Tumor Necrosis Factor-α inhibitors;
43) Resistin and C-Reactive Protein, selecting treatment with Tumor Necrosis Factor-α inhibitors; and
44) Serum Amyloid A and C-Reactive Protein, selecting treatment with one or more of PLAQUENIL (or Hydroxychloroquine), Sulfasalazine, Methotrexate, Tumor Necrosis Factor-α inhibitors and Tocilizumab (or ACTEMRA); and iii. Administering the treatment selected in step (ii) to the patient.

2. The method of claim 1 wherein the selecting in (ii) further comprises identifying the maximum number of biomarkers each one with at least 40% elevated serum level.

3. The method of claim 1 wherein the selecting in (ii) further comprises identifying the maximum number of the highest elevated biomarkers each one with at least 40% elevated serum level.

4. The method of claim 1 wherein the selecting in (ii) further comprises avoiding a treatment method that is contraindicated or causes an allergic response in the patient.

5. The method of claim 4 wherein the selecting further comprises identifying the maximum number of biomarkers each one with at least 40% elevated serum level.

6. The method of claim 4 wherein the selecting further comprises identifying the maximum number of highest elevated biomarkers each one with at least 40% elevated serum level.

7. The method of claim 1 wherein the selecting further comprises selecting a treatment method that is administered via a route selected from the group consisting of intravenous, intraarterial, enteral (oral or rectal), intramuscular, subcutaneous, transdermal, intradermal, nasal, intramuscular, intraperitoneal, intracardiac, epidural, intrathecal, and transmucosal.

8. The method of claim 7 wherein the route is preferred by the patient.

9. The method of claim 1 wherein the selecting further comprises identifying the maximum number of biomarkers each one with at least 40% elevated serum level.

10. The method of claim 1 wherein the selecting further comprises identifying the maximum number of highest elevated biomarkers each one with at least 40% elevated serum level.

11. The method of claim 1 wherein the selecting comprises identifying at least three biomarkers each one with at least 40% elevated serum level.

12. The method of claim 1 wherein the selecting comprises identifying at least four biomarkers each one with at least 40% elevated serum level.

13. The method of claim 1 wherein the selecting comprises identifying at least five biomarkers each one with at least 40% elevated serum level.

14. The method of claim 1 wherein the selecting comprises identifying at least six biomarkers each one with at least 40% elevated serum level.

15. The method of claim 1 wherein the selecting comprises identifying at least two biomarkers each one with at least 50% elevated serum level.

16. The method of claim 1 wherein the selecting comprises identifying at least two biomarkers each one with at least 60% elevated serum level.

17. The method of claim 1 wherein the selecting comprises identifying at least two biomarkers each one with at least 70% elevated serum level.

18. The method of claim 1 wherein the selecting comprises identifying at least two biomarkers each one with at least 80% elevated serum level.

19. The method of claim 1 wherein the selecting comprises identifying at least two biomarkers each one with at least 90% elevated serum level.

20. The method of claim 1 wherein the selecting comprises identifying at least three biomarkers each one with at least 60% elevated serum level.

21. The method of claim 1 wherein the selecting comprises identifying at least four biomarkers each one with at least 60% elevated serum level.

22. The method of claim 1 wherein the selecting comprises identifying at least five biomarkers each one with at least 60% elevated serum level.

23. A method for treating a patient with rheumatoid arthritis with a first treatment method selected from the group consisting of PLAQUENIL (or Hydroxychloroquine), Sulfasalazine, Methotrexate, ARAVA (or Leflunomide), Tumor Necrosis Factor-α inhibitors, Atabacept (or ORENCIA), Tocilizumab (or ACTEMRA), RITUXAN (or Rituximab), and Tofacitinib (or XELJANZ), which comprises:
  i. Determining serum levels in the patient of a group of biomarkers comprising Vascular Cell Adhesion Molecule 1, Vascular Endothelial Growth Factor-A, Interleukin-6, Tumor Necrosis Factor Receptor Type 1, Matrix Metalloproteinase-1, Matrix Metalloproteinase-3, YKL-40, Leptin, Resistin, Serum Amyloid A, and C-Reactive Protein;
  ii. Identifying at least two biomarkers each one with at least 40% elevated serum level over control serum level, wherein if the at least two biomarkers with at least 40% elevated levels are:
   1) Vascular Cell Adhesion Molecule 1 and Vascular Endothelial Growth Factor-A, selecting treatment with Tumor Necrosis Factor-α inhibitors;
   2) Vascular Cell Adhesion Molecule 1 and Interleukin-6, selecting treatment with one or more of ARAVA (Leflunomide) and Atabacept (ORENCIA);
   3) Vascular Cell Adhesion Molecule 1 and Tumor Necrosis Factor Receptor Type 1, selecting treatment with one or more of ARAVA (Leflunomide) and Tumor Necrosis Factor-α inhibitors;
   4) Vascular Cell Adhesion Molecule 1 and Matrix Metalloproteinase-1, selecting treatment with one or more of ARAVA (Leflunomide) and Tumor Necrosis Factor-α inhibitors;
   5) Vascular Cell Adhesion Molecule 1 and Matrix Metalloproteinase-3, selecting treatment with one or more of ARAVA (or Leflunomide), Tumor Necrosis Factor-α inhibitors and Atabacept (or ORENCIA);
   6) Vascular Cell Adhesion Molecule 1 and YKL-40, selecting treatment with Tumor Necrosis Factor-α inhibitors;
   7) Vascular Cell Adhesion Molecule 1 and Resistin, selecting treatment with Tumor Necrosis Factor-α inhibitors;
   8) Vascular Cell Adhesion Molecule 1 and Serum Amyloid A, selecting treatment with one or more of ARAVA (or Leflunomide) and Tumor Necrosis Factor-α;
   9) Vascular Cell Adhesion Molecule 1 and C-Reactive Protein, selecting treatment with one or more of Tumor Necrosis Factor-α inhibitors and Atabacept (or ORENCIA);
   10) Vascular Endothelial Growth Factor-A and Interleukin-6, selecting treatment with one or more of Sulfasalazine, Methotrexate and Tocilizumab (or ACTEMRA);
   11) Vascular Endothelial Growth Factor-A and Tumor Necrosis Factor Receptor Type 1, selecting treatment with one or more of Sulfasalazine and Tumor Necrosis Factor-α inhibitors;
   12) Vascular Endothelial Growth Factor-A and Matrix Metalloproteinase-1, selecting treatment with one or more of Tumor Necrosis Factor-α inhibitors and Tocilizumab (or ACTEMRA);
   13) Vascular Endothelial Growth Factor-A and Matrix Metalloproteinase-3, selecting treatment with one or more of Sulfasalazine, Methotrexate, Tumor Necrosis Factor-α inhibitors and Tocilizumab (or ACTEMRA);
   14) Vascular Endothelial Growth Factor-A and YKL-40, selecting treatment with one or more of Tumor Necrosis Factor-α inhibitors and Tocilizumab (or ACTEMRA);
   15) Vascular Endothelial Growth Factor-A and Resistin, selecting treatment with Tumor Necrosis Factor-α inhibitors;
   16) Vascular Endothelial Growth Factor-A and Serum Amyloid A, selecting treatment with one or more of Sulfasalazine, Methotrexate, Tumor Necrosis Factor-α inhibitors and Tocilizumab (or ACTEMRA);
   17) Vascular Endothelial Growth Factor-A and C-Reactive Protein, selecting treatment with one or more of Sulfasalazine, Methotrexate, Tumor Necrosis Factor-α inhibitors and Tocilizumab (or ACTEMRA);
   18) Interleukin-6 and Tumor Necrosis Factor Receptor Type 1, selecting treatment with one or more of Sulfasalazine and ARAVA (or Leflunomide);
   19) Interleukin-6 and Matrix Metalloproteinase-1, selecting treatment with one or more of ARAVA (or Leflunomide), Tocilizumab (or ACTEMRA) and Tofacitinib (or XELJANZ);
   20) Interleukin-6 and Matrix Metalloproteinase-3, selecting treatment with one or more of Sulfasalazine, Methotrexate, ARAVA (or Leflunomide), Atabacept (or ORENCIA), Tocilizumab (or ACTEMRA) and Tofacitinib (or XELJANZ);
   21) Interleukin-6 and YKL-40, selecting treatment with one or more of Tocilizumab (or ACTEMRA);
   22) Interleukin-6 and Serum Amyloid A, selecting treatment with one or more of PLAQUENIL (or Hydroxychloroquine), Sulfasalazine, Methotrexate, ARAVA (or Leflunomide) and Tocilizumab (or ACTEMRA);
   23) Interleukin-6 and C-Reactive Protein, selecting treatment with one or more of PLAQUENIL (or Hydroxychloroquine), Sulfasalazine, Methotrexate, Atabacept (or ORENCIA), Tocilizumab (or ACTEMRA) and RITUXAN (or Rituximab);
   24) Tumor Necrosis Factor Receptor Type 1 and Matrix Metalloproteinase-1, selecting treatment with one or more of ARAVA (or Leflunomide) and Tumor Necrosis Factor-α inhibitors;
   25) Tumor Necrosis Factor Receptor Type 1 and Matrix Metalloproteinase-3, selecting treatment with one or more of Sulfasalazine, ARAVA (or Leflunomide) and Tumor Necrosis Factor-α inhibitors;
   26) Tumor Necrosis Factor Receptor Type 1 and YKL-40, selecting treatment with Tumor Necrosis Factor-α inhibitors;
   27) Tumor Necrosis Factor Receptor Type 1 and Resistin, selecting treatment with Tumor Necrosis Factor-α inhibitors;
   28) Tumor Necrosis Factor Receptor Type 1 and Serum Amyloid A, selecting treatment with one or more of Sulfasalazine, ARAVA (or Leflunomide) and Tumor Necrosis Factor-α inhibitors;
   29) Tumor Necrosis Factor Receptor Type 1 and C-Reactive Protein, selecting treatment with one or more of Sulfasalazine and Tumor Necrosis Factor-α inhibitors;
   30) Matrix Metalloproteinase-1 and Matrix Metalloproteinase-3, selecting treatment with one or more of ARAVA (or Leflunomide), Tumor Necrosis Factor-α inhibitors, Tocilizumab (or ACTEMRA) and Tofacitinib (or XELJANZ);

31) Matrix Metalloproteinase-1 and YKL-40, selecting treatment with one or more of Tumor Necrosis Factor-α inhibitors and Tocilizumab (or ACTEMRA);
32) Matrix Metalloproteinase-1 and Resistin, selecting treatment with Tumor Necrosis Factor-α inhibitors;
33) Matrix Metalloproteinase-1 and Serum Amyloid A, selecting treatment with one or more of ARAVA (or Leflunomide), Tumor Necrosis Factor-α inhibitors and Tocilizumab (or ACTEMRA);
34) Matrix Metalloproteinase-1 and C-Reactive Protein, selecting treatment with one or more of Tumor Necrosis Factor-α inhibitors and Tocilizumab (or ACTEMRA);
35) Matrix Metalloproteinase-3 and YKL-40, selecting treatment with one or more of Tumor Necrosis Factor-α inhibitors and Tocilizumab (or ACTEMRA);
36) Matrix Metalloproteinase-3 and Resistin, selecting treatment with Tumor Necrosis Factor-α inhibitors;
37) Matrix Metalloproteinase-3 and Serum Amyloid A, selecting treatment with one or more of Sulfasalazine, Methotrexate, ARAVA (or Leflunomide), Tumor Necrosis Factor-α inhibitors and Tocilizumab (or ACTEMRA);
38) Matrix Metalloproteinase-3 and C-Reactive Protein, selecting treatment with one or more of Sulfasalazine, Methotrexate, Tumor Necrosis Factor-α inhibitors, Atabacept (or ORENCIA) and Tocilizumab (or ACTEMRA);
39) YKL-40 and Resistin, selecting treatment with Tumor Necrosis Factor-α inhibitors;
40) YKL-40 and Serum Amyloid A, selecting treatment with one or more of Tumor Necrosis Factor-α inhibitors and Tocilizumab (or ACTEMRA);
41) YKL-40 and C-Reactive Protein, selecting treatment with one or more of Tumor Necrosis Factor-α inhibitors and Tocilizumab (or ACTEMRA);
42) Resistin and Serum Amyloid A, selecting treatment with Tumor Necrosis Factor-α inhibitors;
43) Resistin and C-Reactive Protein, selecting treatment with Tumor Necrosis Factor-α inhibitors; and
44) Serum Amyloid A and C-Reactive Protein, selecting treatment with one or more of PLAQUENIL (or Hydroxychloroquine), Sulfasalazine, Methotrexate, Tumor Necrosis Factor-α inhibitors and Tocilizumab (or ACTEMRA);

iii. Administering the first treatment method selected in step (ii) to the patient; and
iv. Determining effectiveness or ineffectiveness of the first treatment method administered in step (iii) to the patient.

24. The method of claim 23 which further comprises
v. Selecting a second treatment method, and
vi. Administering the second treatment method selected in step (v) to the patient.

25. The method of claim 24 wherein the selecting for the second treatment method in (v) comprises:
i. Identifying at least two biomarkers selected from the group consisting of Vascular Cell Adhesion Molecule 1, Vascular Endothelial Growth Factor-A, Interleukin-6, Tumor Necrosis Factor Receptor Type 1, Matrix Metalloproteinase-1, Matrix Metalloproteinase-3, YKL-40, Leptin, Resistin, Serum Amyloid A, and C-Reactive Protein, each one with at least 40% elevated serum level over control serum level, wherein if the at least two biomarkers with at least 40% elevated levels are:
1) Vascular Cell Adhesion Molecule 1 and Vascular Endothelial Growth Factor-A, selecting treatment with Tumor Necrosis Factor-α inhibitors;
2) Vascular Cell Adhesion Molecule 1 and Interleukin-6, selecting treatment with one or more of ARAVA (Leflunomide) and Atabacept (ORENCIA);
3) Vascular Cell Adhesion Molecule 1 and Tumor Necrosis Factor Receptor Type 1, selecting treatment with one or more of ARAVA (Leflunomide) and Tumor Necrosis Factor-α inhibitors;
4) Vascular Cell Adhesion Molecule 1 and Matrix Metalloproteinase-1, selecting treatment with one or more of ARAVA (Leflunomide) and Tumor Necrosis Factor-α inhibitors;
5) Vascular Cell Adhesion Molecule 1 and Matrix Metalloproteinase-3, selecting treatment with one or more of ARAVA (or Leflunomide), Tumor Necrosis Factor-α inhibitors and Atabacept (or ORENCIA);
6) Vascular Cell Adhesion Molecule 1 and YKL-40, selecting treatment with Tumor Necrosis Factor-α inhibitors;
7) Vascular Cell Adhesion Molecule 1 and Resistin, selecting treatment with Tumor Necrosis Factor-α inhibitors;
8) Vascular Cell Adhesion Molecule 1 and Serum Amyloid A, selecting treatment with one or more of ARAVA (or Leflunomide) and Tumor Necrosis Factor-α;
9) Vascular Cell Adhesion Molecule 1 and C-Reactive Protein, selecting treatment with one or more of Tumor Necrosis Factor-α inhibitors and Atabacept (or ORENCIA);
10) Vascular Endothelial Growth Factor-A and Interleukin-6, selecting treatment with one or more of Sulfasalazine, Methotrexate and Tocilizumab (or ACTEMRA);
11) Vascular Endothelial Growth Factor-A and Tumor Necrosis Factor Receptor Type 1, selecting treatment with one or more of Sulfasalazine and Tumor Necrosis Factor-α inhibitors;
12) Vascular Endothelial Growth Factor-A and Matrix Metalloproteinase-1, selecting treatment with one or more of Tumor Necrosis Factor-α inhibitors and Tocilizumab (or ACTEMRA);
13) Vascular Endothelial Growth Factor-A and Matrix Metalloproteinase-3, selecting treatment with one or more of Sulfasalazine, Methotrexate, Tumor Necrosis Factor-α inhibitors and Tocilizumab (or ACTEMRA);
14) Vascular Endothelial Growth Factor-A and YKL-40, selecting treatment with one or more of Tumor Necrosis Factor-α inhibitors and Tocilizumab (or ACTEMRA);
15) Vascular Endothelial Growth Factor-A and Resistin, selecting treatment with Tumor Necrosis Factor-α inhibitors;
16) Vascular Endothelial Growth Factor-A and Serum Amyloid A, selecting treatment with one or more of Sulfasalazine, Methotrexate, Tumor Necrosis Factor-α inhibitors and Tocilizumab (or ACTEMRA);
17) Vascular Endothelial Growth Factor-A and C-Reactive Protein, selecting treatment with one or more of Sulfasalazine, Methotrexate, Tumor Necrosis Factor-α inhibitors and Tocilizumab (or ACTEMRA);
18) Interleukin-6 and Tumor Necrosis Factor Receptor Type 1, selecting treatment with one or more of Sulfasalazine and ARAVA (or Leflunomide);
19) Interleukin-6 and Matrix Metalloproteinase-1, selecting treatment with one or more of ARAVA (or Leflunomide), Tocilizumab (or ACTEMRA) and Tofacitinib (or XELJANZ);
20) Interleukin-6 and Matrix Metalloproteinase-3, selecting treatment with one or more of Sulfasalazine, Methotrexate, ARAVA (or Leflunomide), Atabacept (or ORENCIA), Tocilizumab (or ACTEMRA) and Tofacitinib (or XELJANZ);
21) Interleukin-6 and YKL-40, selecting treatment with one or more of Tocilizumab (or ACTEMRA);
22) Interleukin-6 and Serum Amyloid A, selecting treatment with one or more of PLAQUENIL (or Hydroxychloroquine), Sulfasalazine, Methotrexate, ARAVA (or Leflunomide) and Tocilizumab (or ACTEMRA);
23) Interleukin-6 and C-Reactive Protein, selecting treatment with one or more of PLAQUENIL (or Hydroxychloroquine), Sulfasalazine, Methotrexate, Atabacept (or ORENCIA), Tocilizumab (or ACTEMRA) and RITUXAN (or Rituximab);
24) Tumor Necrosis Factor Receptor Type 1 and Matrix Metalloproteinase-1, selecting treatment with one or more of ARAVA (or Leflunomide) and Tumor Necrosis Factor-α inhibitors;
25) Tumor Necrosis Factor Receptor Type 1 and Matrix Metalloproteinase-3, selecting treatment with one or more of Sulfasalazine, ARAVA (or Leflunomide) and Tumor Necrosis Factor-α inhibitors;
26) Tumor Necrosis Factor Receptor Type 1 and YKL-40, selecting treatment with Tumor Necrosis Factor-α inhibitors;
27) Tumor Necrosis Factor Receptor Type 1 and Resistin, selecting treatment with Tumor Necrosis Factor-α inhibitors;
28) Tumor Necrosis Factor Receptor Type 1 and Serum Amyloid A, selecting treatment with one or more of Sulfasalazine, ARAVA (or Leflunomide) and Tumor Necrosis Factor-α inhibitors;
29) Tumor Necrosis Factor Receptor Type 1 and C-Reactive Protein, selecting treatment with one or more of Sulfasalazine and Tumor Necrosis Factor-α inhibitors;
30) Matrix Metalloproteinase-1 and Matrix Metalloproteinase-3, selecting treatment with one or more of ARAVA (or Leflunomide), Tumor Necrosis Factor-α inhibitors, Tocilizumab (or ACTEMRA) and Tofacitinib (or XELJANZ);
31) Matrix Metalloproteinase-1 and YKL-40, selecting treatment with one or more of Tumor Necrosis Factor-α inhibitors and Tocilizumab (or ACTEMRA);
32) Matrix Metalloproteinase-1 and Resistin, selecting treatment with Tumor Necrosis Factor-α inhibitors;
33) Matrix Metalloproteinase-1 and Serum Amyloid A, selecting treatment with one or more of ARAVA (or Leflunomide), Tumor Necrosis Factor-α inhibitors and Tocilizumab (or ACTEMRA);
34) Matrix Metalloproteinase-1 and C-Reactive Protein, selecting treatment with one or more of Tumor Necrosis Factor-α inhibitors and Tocilizumab (or ACTEMRA);
35) Matrix Metalloproteinase-3 and YKL-40, selecting treatment with one or more of Tumor Necrosis Factor-α inhibitors and Tocilizumab (or ACTEMRA);
36) Matrix Metalloproteinase-3 and Resistin, selecting treatment with Tumor Necrosis Factor-α inhibitors;
37) Matrix Metalloproteinase-3 and Serum Amyloid A, selecting treatment with one or more of Sulfasalazine, Methotrexate, ARAVA (or Leflunomide), Tumor Necrosis Factor-α inhibitors and Tocilizumab (or ACTEMRA);
38) Matrix Metalloproteinase-3 and C-Reactive Protein, selecting treatment with one or more of Sulfasalazine, Methotrexate, Tumor Necrosis Factor-α inhibitors, Atabacept (or ORENCIA) and Tocilizumab (or ACTEMRA);
39) YKL-40 and Resistin, selecting treatment with Tumor Necrosis Factor-α inhibitors;
40) YKL-40 and Serum Amyloid A, selecting treatment with one or more of Tumor Necrosis Factor-α inhibitors and Tocilizumab (or ACTEMRA);
41) YKL-40 and C-Reactive Protein, selecting treatment with one or more of Tumor Necrosis Factor-α inhibitors and Tocilizumab (or ACTEMRA);
42) Resistin and Serum Amyloid A, selecting treatment with Tumor Necrosis Factor-α inhibitors;
43) Resistin and C-Reactive Protein, selecting treatment with Tumor Necrosis Factor-α inhibitors; and
44) Serum Amyloid A and C-Reactive Protein, selecting treatment with one or more of PLAQUENIL (or Hydroxychloroquine), Sulfasalazine, Methotrexate, Tumor Necrosis Factor-α inhibitors and Tocilizumab (or ACTEMRA).

26. The method of claim 23 wherein the determining in (iv) comprises:
   i. Determining one or more selected from the group consisting of Vectra DA Score, hemoglobin count, platelet count, CRP level, and Erythrocyte Sedimentation Rate in the patient before and after the first treatment method; and
   ii. Comparing the one or more selected from the group consisting of Vectra DA Score, hemoglobin count, platelet count, CRP level, and Erythrocyte Sedimentation Rate in the patient before and after the first treatment method.

27. The method of claim 23 wherein the determining in (iv) comprises:
   i. Determining Vectra DA Score, hemoglobin count, platelet count, CRP level, and Erythrocyte Sedimentation Rate in the patient before and after the first treatment method; and
   ii. Comparing the Vectra DA Score, hemoglobin count, platelet count, CRP level, and Erythrocyte Sedimentation Rate in the patient before and after the first treatment method.

28. A method for treating a patient with rheumatoid arthritis, with one or more treatments selected from the group consisting of PLAQUENIL (or Hydroxychloroquine), Sulfasalazine, Methotrexate, ARAVA (or Leflunomide), Tumor Necrosis Factor-α inhibitors, Atabacept (or ORENCIA), Tocilizumab (or ACTEMRA), RITUXAN (or Rituximab), and Tofacitinib (or XELJANZ), which comprises: administering to a patient, determined to have at least 40% elevated serum levels over control serum levels of at least two biomarkers selected from the group consisting of Vascular Cell Adhesion Molecule 1, Vascular Endothelial Growth Factor-A, Interleukin-6, Tumor Necrosis Factor Receptor Type 1, Matrix Metalloproteinase-1, Matrix Metalloproteinase-3, YKL-40, Leptin, Resistin, Serum Amyloid A, and C-Reactive Protein, a treatment method, wherein if the at least two biomarkers with at least 40% elevated levels are:
   1) Vascular Cell Adhesion Molecule 1 and Vascular Endothelial Growth Factor-A, selecting treatment with Tumor Necrosis Factor-α inhibitors;

2) Vascular Cell Adhesion Molecule 1 and Interleukin-6, selecting treatment with one or more of ARAVA (Leflunomide) and Atabacept (ORENCIA);
3) Vascular Cell Adhesion Molecule 1 and Tumor Necrosis Factor Receptor Type 1, selecting treatment with one or more of ARAVA (Leflunomide) and Tumor Necrosis Factor-α inhibitors;
4) Vascular Cell Adhesion Molecule 1 and Matrix Metalloproteinase-1, selecting treatment with one or more of ARAVA (Leflunomide) and Tumor Necrosis Factor-α inhibitors;
5) Vascular Cell Adhesion Molecule 1 and Matrix Metalloproteinase-3, selecting treatment with one or more of ARAVA (or Leflunomide), Tumor Necrosis Factor-α inhibitors and Atabacept (or ORENCIA);
6) Vascular Cell Adhesion Molecule 1 and YKL-40, selecting treatment with Tumor Necrosis Factor-α inhibitors;
7) Vascular Cell Adhesion Molecule 1 and Resistin, selecting treatment with Tumor Necrosis Factor-α inhibitors;
8) Vascular Cell Adhesion Molecule 1 and Serum Amyloid A, selecting treatment with one or more of ARAVA (or Leflunomide) and Tumor Necrosis Factor-α;
9) Vascular Cell Adhesion Molecule 1 and C-Reactive Protein, selecting treatment with one or more of Tumor Necrosis Factor-α inhibitors and Atabacept (or ORENCIA);
10) Vascular Endothelial Growth Factor-A and Interleukin-6, selecting treatment with one or more of Sulfasalazine, Methotrexate and Tocilizumab (or ACTEMRA);
11) Vascular Endothelial Growth Factor-A and Tumor Necrosis Factor Receptor Type 1, selecting treatment with one or more of Sulfasalazine and Tumor Necrosis Factor-α inhibitors;
12) Vascular Endothelial Growth Factor-A and Matrix Metalloproteinase-1, selecting treatment with one or more of Tumor Necrosis Factor-α inhibitors and Tocilizumab (or ACTEMRA);
13) Vascular Endothelial Growth Factor-A and Matrix Metalloproteinase-3, selecting treatment with one or more of Sulfasalazine, Methotrexate, Tumor Necrosis Factor-α inhibitors and Tocilizumab (or ACTEMRA);
14) Vascular Endothelial Growth Factor-A and YKL-40, selecting treatment with one or more of Tumor Necrosis Factor-α inhibitors and Tocilizumab (or ACTEMRA);
15) Vascular Endothelial Growth Factor-A and Resistin, selecting treatment with Tumor Necrosis Factor-α inhibitors;
16) Vascular Endothelial Growth Factor-A and Serum Amyloid A, selecting treatment with one or more of Sulfasalazine, Methotrexate, Tumor Necrosis Factor-α inhibitors and Tocilizumab (or ACTEMRA);
17) Vascular Endothelial Growth Factor-A and C-Reactive Protein, selecting treatment with one or more of Sulfasalazine, Methotrexate, Tumor Necrosis Factor-α inhibitors and Tocilizumab (or ACTEMRA);
18) Interleukin-6 and Tumor Necrosis Factor Receptor Type 1, selecting treatment with one or more of Sulfasalazine and ARAVA (or Leflunomide);
19) Interleukin-6 and Matrix Metalloproteinase-1, selecting treatment with one or more of ARAVA (or Leflunomide), Tocilizumab (or ACTEMRA) and Tofacitinib (or XELJANZ);
20) Interleukin-6 and Matrix Metalloproteinase-3 selectins treatment with one or more of Sulfasalazine, Methotrexate, ARAVA (or Leflunomide), Atabacept (or ORENCIA), Tocilizumab (or ACTEMRA) and Tofacitinib (or XELJANZ);
21) Interleukin-6 and YKL-40, selecting treatment with one or more of Tocilizumab (or ACTEMRA);
22) Interleukin-6 and Serum Amyloid A, selecting treatment with one or more of PLAQUENIL (or Hydroxychloroquine), Sulfasalazine, Methotrexate, ARAVA (or Leflunomide) and Tocilizumab (or ACTEMRA);
23) Interleukin-6 and C-Reactive Protein, selecting treatment with one or more of PLAQUENIL (or Hydroxychloroquine), Sulfasalazine, Methotrexate, Atabacept (or ORENCIA), Tocilizumab (or ACTEMRA) and RITUXAN (or Rituximab);
24) Tumor Necrosis Factor Receptor Type 1 and Matrix Metalloproteinase-1, selecting treatment with one or more of ARAVA (or Leflunomide) and Tumor Necrosis Factor-α inhibitors;
25) Tumor Necrosis Factor Receptor Type 1 and Matrix Metalloproteinase-3, selecting treatment with one or more of Sulfasalazine, ARAVA (or Leflunomide) and Tumor Necrosis Factor-α inhibitors;
26) Tumor Necrosis Factor Receptor Type 1 and YKL-40, selecting treatment with Tumor Necrosis Factor-α inhibitors;
27) Tumor Necrosis Factor Receptor Type 1 and Resistin, selecting treatment with Tumor Necrosis Factor-α inhibitors;
28) Tumor Necrosis Factor Receptor Type 1 and Serum Amyloid A, selecting treatment with one or more of Sulfasalazine, ARAVA (or Leflunomide) and Tumor Necrosis Factor-α inhibitors;
29) Tumor Necrosis Factor Receptor Type 1 and C-Reactive Protein, selecting treatment with one or more of Sulfasalazine and Tumor Necrosis Factor-α inhibitors;
30) Matrix Metalloproteinase-1 and Matrix Metalloproteinase-3, selecting treatment with one or more of ARAVA (or Leflunomide), Tumor Necrosis Factor-α inhibitors, Tocilizumab (or ACTEMRA) and Tofacitinib (or XELJANZ);
31) Matrix Metalloproteinase-1 and YKL-40, selecting treatment with one or more of Tumor Necrosis Factor-α inhibitors and Tocilizumab (or ACTEMRA);
32) Matrix Metalloproteinase-1 and Resistin, selecting treatment with Tumor Necrosis Factor-α inhibitors;
33) Matrix Metalloproteinase-1 and Serum Amyloid A, selecting treatment with one or more of ARAVA (or Leflunomide), Tumor Necrosis Factor-α inhibitors and Tocilizumab (or ACTEMRA);
34) Matrix Metalloproteinase-1 and C-Reactive Protein, selecting treatment with one or more of Tumor Necrosis Factor-α inhibitors and Tocilizumab (or ACTEMRA);
35) Matrix Metalloproteinase-3 and YKL-40, selecting treatment with one or more of Tumor Necrosis Factor-α inhibitors and Tocilizumab (or ACTEMRA);
36) Matrix Metalloproteinase-3 and Resistin, selecting treatment with Tumor Necrosis Factor-α inhibitors;
37) Matrix Metalloproteinase-3 and Serum Amyloid A, selecting treatment with one or more of Sulfasalazine, Methotrexate, ARAVA (or Leflunomide), Tumor Necrosis Factor-α inhibitors and Tocilizumab (or ACTEMRA);
38) Matrix Metalloproteinase-3 and C-Reactive Protein, selecting treatment with one or more of Sulfasalazine, Methotrexate, Tumor Necrosis Factor-α inhibitors, Atabacept (or ORENCIA) and Tocilizumab (or ACTEMRA);
39) YKL-40 and Resistin, selecting treatment with Tumor Necrosis Factor-α inhibitors;

40) YKL-40 and Serum Amyloid A, selecting treatment with one or more of Tumor Necrosis Factor-α inhibitors and Tocilizumab (or ACTEMRA);
41) YKL-40 and C-Reactive Protein, selecting treatment with one or more of Tumor Necrosis Factor-α inhibitors and Tocilizumab (or ACTEMRA);
42) Resistin and Serum Amyloid A, selecting treatment with Tumor Necrosis Factor-α inhibitors;
43) Resistin and C-Reactive Protein, selecting treatment with Tumor Necrosis Factor-α inhibitors; and
44) Serum Amyloid A and C-Reactive Protein, selecting treatment with one or more of PLAQUENIL (or Hydroxychloroquine), Sulfasalazine, Methotrexate, Tumor Necrosis Factor-α inhibitors and Tocilizumab (or ACTEMRA).

* * * * *

Disclaimer

9,387,246 B2 - L. Douglas Graham, Chicago, IL (US). TREATMENT METHODS FOR RHEUMATOID ARTHRITIS. Patent dated July 12, 2016. Disclaimer filed July 24, 2017, by the inventor.

I hereby disclaim the following complete claims 1-28 of said patent.

*(Official Gazette, July 19, 2022)*